United States Patent
Barlaam et al.

(10) Patent No.: US 11,613,539 B2
(45) Date of Patent: *Mar. 28, 2023

(54) IMIDAZO[4,5-C]QUINOLIN-2-ONE COMPOUNDS AND THEIR USE IN TREATING CANCER

(71) Applicant: AstraZeneca AB, Sodertalje (SE)

(72) Inventors: Bernard Christophe Barlaam, Cambridge (GB); Kurt Gordon Pike, Cambridge (GB); Andrew John Eatherton, Cambridge (GB); Thomas Anthony Hunt, Cambridge (GB)

(73) Assignee: ASTRAZENECA AB, Sodertalje (SE)

(*) Notice: Subject to any disclaimer, the term of this patent is extended or adjusted under 35 U.S.C. 154(b) by 177 days.

This patent is subject to a terminal disclaimer.

(21) Appl. No.: 17/108,117

(22) Filed: Dec. 1, 2020

(65) Prior Publication Data

US 2021/0147416 A1 May 20, 2021

Related U.S. Application Data

(63) Continuation of application No. 16/584,996, filed on Sep. 27, 2019, now Pat. No. 10,882,858, which is a continuation of application No. 15/822,617, filed on Nov. 27, 2017, now Pat. No. 10,457,679, which is a continuation of application No. 15/267,398, filed on Sep. 16, 2016, now Pat. No. 9,856,255.

(30) Foreign Application Priority Data

Sep. 17, 2015 (GB) .................................. 1516504

(51) Int. Cl.
| | |
|---|---|
| *C07D 471/04* | (2006.01) |
| *A61P 35/00* | (2006.01) |
| *A61K 31/4745* | (2006.01) |
| *A61K 45/06* | (2006.01) |

(52) U.S. Cl.
CPC ........ *C07D 471/04* (2013.01); *A61K 31/4745* (2013.01); *A61K 45/06* (2013.01); *A61P 35/00* (2018.01)

(58) Field of Classification Search
CPC .. C07D 471/04; A61K 31/4745; A61K 45/06; A61P 35/00; A61P 25/28
See application file for complete search history.

(56) References Cited

U.S. PATENT DOCUMENTS

| | | | |
|---|---|---|---|
| 7,667,039 B2 | 2/2010 | Garcia-Echeverria et al. | |
| 8,557,984 B2 | 10/2013 | Bouillot et al. | |
| 9,000,153 B2 | 4/2015 | Fuchss et al. | |
| 9,856,255 B2* | 1/2018 | Barlaam | C07D 471/04 |
| 10,457,677 B2* | 10/2019 | Fuchss | A61K 31/4375 |
| 2002/0151712 A1 | 10/2002 | Lin et al. | |
| 2005/0245562 A1 | 11/2005 | Garcia-Echeverria et al. | |
| 2008/0293739 A1 | 11/2008 | Trede et al. | |
| 2013/0172337 A1 | 7/2013 | Fuchss et al. | |
| 2018/0072715 A1 | 3/2018 | Fuchss et al. | |

FOREIGN PATENT DOCUMENTS

| | | |
|---|---|---|
| CN | 102199152 A | 9/2011 |
| CN | 102372711 A | 3/2012 |
| CN | 102399218 A | 4/2012 |
| CN | 104876912 A | 9/2015 |
| EP | 0614664 A1 | 9/1994 |
| EP | 1270535 A2 | 1/2003 |
| JP | 2002293745 A | 10/2002 |
| JP | 2003128641 A | 5/2003 |
| JP | 2003300940 A | 10/2003 |

(Continued)

OTHER PUBLICATIONS

Lu, X.-H., "Targeting ATM ameliorates mutant Huntingtin toxicity in cell and animal models of Huntington's disease." Science translational medicine 6.268 (2014):1-12.*
Huntington Dis Symptoms and causes—1998-2022 Mayo Clinic. pdf.*
Lavin, M.F.; 'Ataxi-telangiectasia: from a rare disorder to a paradigm for cell signaling and cancer', Nature Rev. Mol. Cell Biol. 2008, vol. 9; 759-769.
Cremona et al., 'ATM Signalling and cancer', Oncogene 2014; vol. 33; 3351-3360.
Matsuoka et al., 'ATM and ATR Substrate Analysis Reveals Extensive Protein Networks Responsive to DNA Damage' Science 2007, vol. 316; pp. 1160-1166.
Kurz and Lees Miller, 'DNA damage-induced activation of ATM and ATM-dependent signaling pathways', DNA Repair, 2004; vol. 3; pp. 889-900.

(Continued)

*Primary Examiner* — John M Mauro

(57) ABSTRACT

The specification generally relates to compounds of Formula (I):

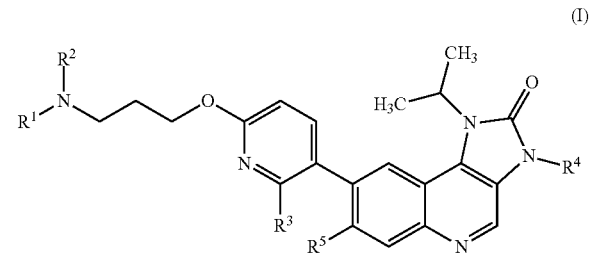

and pharmaceutically acceptable salts thereof, where $R^1$, $R^2$, $R^3$, $R^4$ and $R^5$ have any of the meanings defined herein. The specification also relates to the use of compounds of Formula (I) and salts thereof to treat or prevent ATM mediated disease, including cancer. The specification further relates to pharmaceutical compositions comprising substituted imidazo[4,5-c]quinolin-2-one compounds and pharmaceutically acceptable salts thereof; kits comprising such compounds and salts; methods of manufacture of such compounds and salts; and intermediates useful in such manufacture.

9 Claims, 4 Drawing Sheets

(56) References Cited

FOREIGN PATENT DOCUMENTS

| | | |
|---|---|---|
| JP | 2005170939 A | 6/2005 |
| JP | 2009023986 A | 2/2009 |
| JP | 201367595 A | 4/2013 |
| WO | 1992006683 A1 | 4/1992 |
| WO | 199722596 A1 | 6/1997 |
| WO | 199730035 A1 | 8/1997 |
| WO | 199732856 A1 | 9/1997 |
| WO | 199813354 A1 | 4/1998 |
| WO | 1999032117 A1 | 7/1999 |
| WO | 2000007595 A1 | 2/2000 |
| WO | 2000046203 A2 | 8/2000 |
| WO | 2002030357 A2 | 4/2002 |
| WO | 2002030358 A2 | 4/2002 |
| WO | 2002051831 A1 | 7/2002 |
| WO | 2002076177 A2 | 10/2002 |
| WO | 2002087618 A1 | 11/2002 |
| WO | 2002094264 A1 | 11/2002 |
| WO | 2003062392 A2 | 7/2003 |
| WO | 2003084997 A1 | 10/2003 |
| WO | 2003097641 A2 | 11/2003 |
| WO | 2004007472 A1 | 1/2004 |
| WO | 2004017920 A2 | 3/2004 |
| WO | 2004017922 A2 | 3/2004 |
| WO | 2004078756 A2 | 9/2004 |
| WO | 2004078756 A3 | 9/2004 |
| WO | 2004080943 A1 | 9/2004 |
| WO | 2004113258 A1 | 12/2004 |
| WO | 2005023771 A1 | 3/2005 |
| WO | 2005054237 A1 | 6/2005 |
| WO | 2006038594 A1 | 4/2006 |
| WO | 2006064757 A1 | 6/2006 |
| WO | 2006122806 A2 | 11/2006 |
| WO | 2007005779 A2 | 1/2007 |
| WO | 2007025187 A1 | 3/2007 |
| WO | 2008063300 A2 | 5/2008 |
| WO | 2008090353 A1 | 7/2008 |
| WO | 2008103636 A1 | 8/2008 |
| WO | 2008109177 A2 | 9/2008 |
| WO | 2008109178 A1 | 9/2008 |
| WO | 2008109179 A1 | 9/2008 |
| WO | 2008109180 A2 | 9/2008 |
| WO | 2008109181 A2 | 9/2008 |
| WO | 2008144463 A1 | 11/2008 |
| WO | 2008144464 A1 | 11/2008 |
| WO | 2008154221 A2 | 12/2008 |
| WO | 2009024095 A1 | 2/2009 |
| WO | 2009118324 A1 | 10/2009 |
| WO | 2010003025 A1 | 1/2010 |
| WO | 2010007756 A1 | 1/2010 |
| WO | 2010038165 A1 | 4/2010 |
| WO | 2010077680 A2 | 7/2010 |
| WO | 2010114919 A2 | 10/2010 |
| WO | 2010129567 A1 | 11/2010 |
| WO | 2010129570 A1 | 11/2010 |
| WO | 2010139731 A1 | 12/2010 |
| WO | 2010139747 A1 | 12/2010 |
| WO | 2011036284 A1 | 3/2011 |
| WO | 2011054846 A1 | 5/2011 |
| WO | 2012025213 A2 | 3/2012 |
| WO | 2012028233 A1 | 3/2012 |
| WO | 2012047775 A1 | 4/2012 |
| WO | 2012075253 A2 | 6/2012 |
| WO | 2012077031 A1 | 6/2012 |
| WO | 2012083866 A1 | 6/2012 |
| WO | 2012092471 A2 | 7/2012 |
| WO | 2012138789 A2 | 10/2012 |
| WO | 2012162254 A1 | 11/2012 |
| WO | 2012162635 A1 | 11/2012 |
| WO | 2013022740 A2 | 2/2013 |
| WO | 2013070659 A1 | 5/2013 |
| WO | 2013074965 A1 | 5/2013 |
| WO | 2013157018 A1 | 10/2013 |
| WO | 2013184621 A1 | 12/2013 |
| WO | 2013184755 A2 | 12/2013 |
| WO | 2013192367 A1 | 12/2013 |
| WO | 2014028566 A1 | 2/2014 |
| WO | 2014031872 A2 | 2/2014 |
| WO | 2014165232 A1 | 10/2014 |
| WO | 2014188193 A1 | 11/2014 |
| WO | 2015073804 A2 | 5/2015 |
| WO | 2015084384 A1 | 6/2015 |
| WO | 2015170081 A1 | 11/2015 |
| WO | 2015189560 A1 | 12/2015 |
| WO | 2016155884 A1 | 10/2016 |
| WO | 2017011323 A1 | 1/2017 |
| WO | 2017161028 A1 | 9/2017 |

OTHER PUBLICATIONS

Bakkenist et al., 'DNA damage activates ATM through intermolecular autophosphorylation and dimer dissociation', Nature 2003; vol. 421; pp. 499-506.

Cheng et al 'Discovery of the highly potent PI3/Mtor Dual Inhibitor PF-04979064 through structure-based drug design' ACS Medicinal Chemistry Letters (2013); vol. 4; pp. 91-97.

International Search Report for PCT/GB2015/051312; dated Jul. 24, 2015.

Written Opinion for PCT/GB2015/051312; dated Jul. 24, 2015.

Calabresi and Chabner, Section IX "Chemotherapy of neoplastic Diseases—Introduction" Goodman & Gilman's The Pharmocological Basis of Therapeutics $10^{th}$ ed., 2001, table IX-1.

Batey, M.A., "Preclinical evaluation of a novel ATM inhibitor, KU59403, in vitro and in vivo in p53 functional and dysfunctional models of human cancer", Molecular Cancer Therapeutics, 12.6 (2013), p. 959-967.

Stagni, V, "Tug of war between survival and death: exploring ATM function in cancer", International Journal of Molecular Sciences, 15.4 (2014), p. 5388-5409.

Choi et al., "ATM Mutations in Cancer: Therapeutic Implications", Molecular Cancer Therapeutics 15.8 (2016), p. 1781-1791.

\* cited by examiner

Figure 1: X-Ray Powder Diffraction Pattern of Form A of 7-Fluoro-1-isopropyl-3-methyl-8-[6-[3-(1-piperidyl)propoxy]-3-pyridyl]imidazo[4,5-c]quinolin-2-one
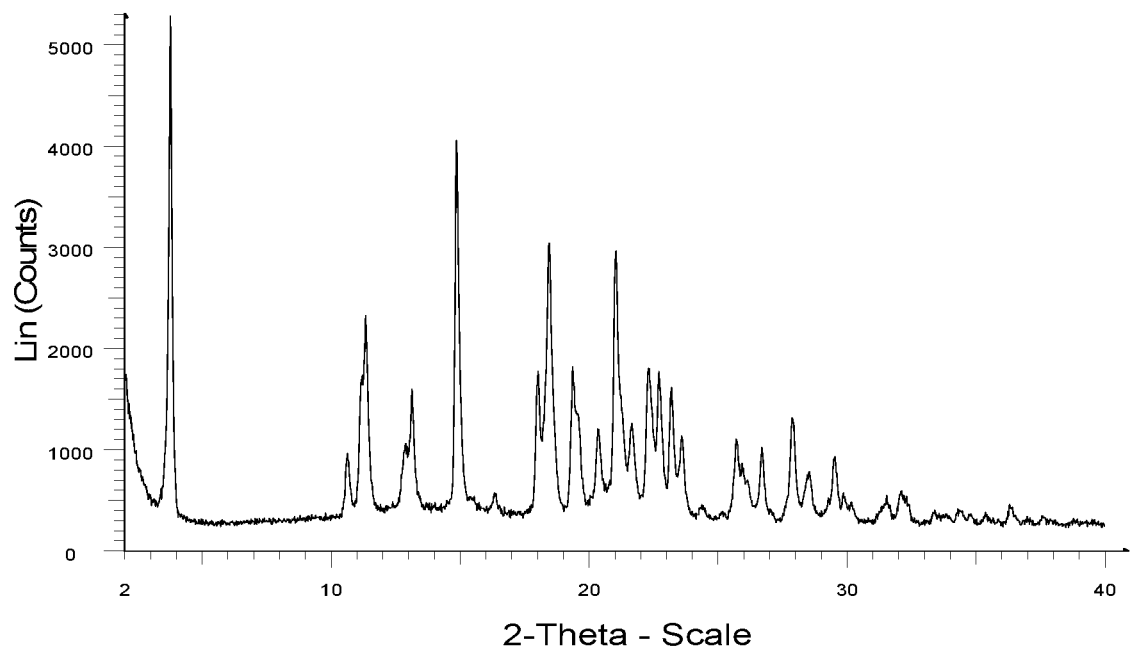

Figure 2: DSC Thermogram of Form A of 7-Fluoro-1-isopropyl-3-methyl-8-[6-[3-(1-piperidyl)propoxy]-3-pyridyl]imidazo[4,5-c]quinolin-2-one
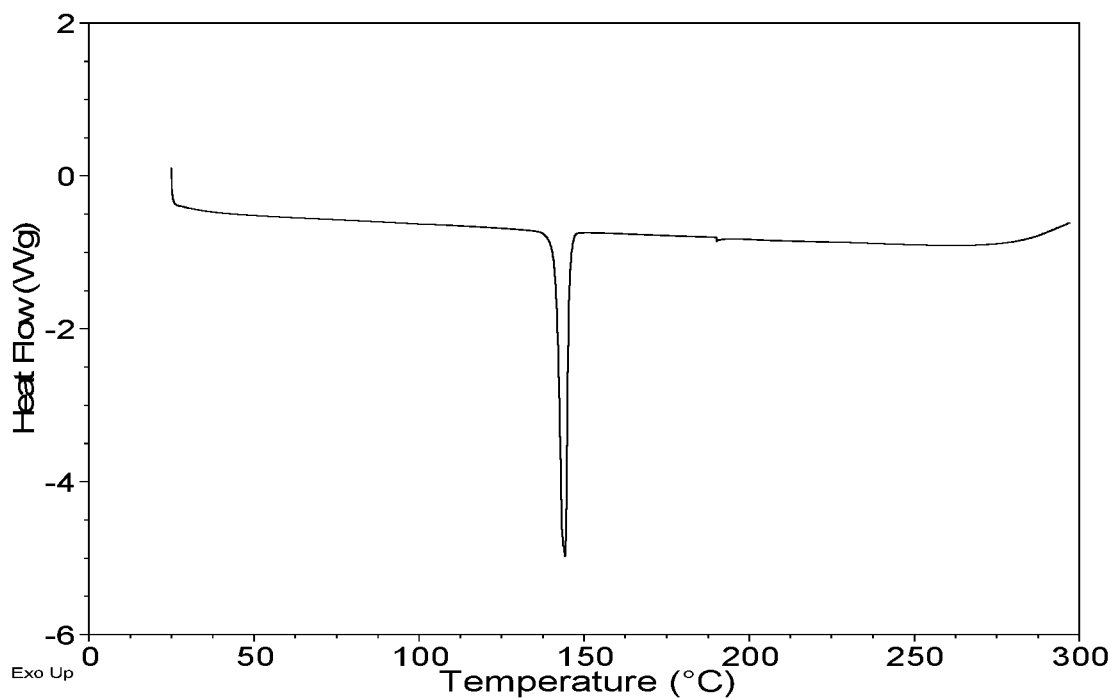

Figure 3: X-Ray Powder Diffraction Pattern of Form B of 7-Fluoro-1-isopropyl-3-methyl-8-[6-[3-(1-piperidyl)propoxy]-3-pyridyl]imidazo[4,5-c]quinolin-2-one
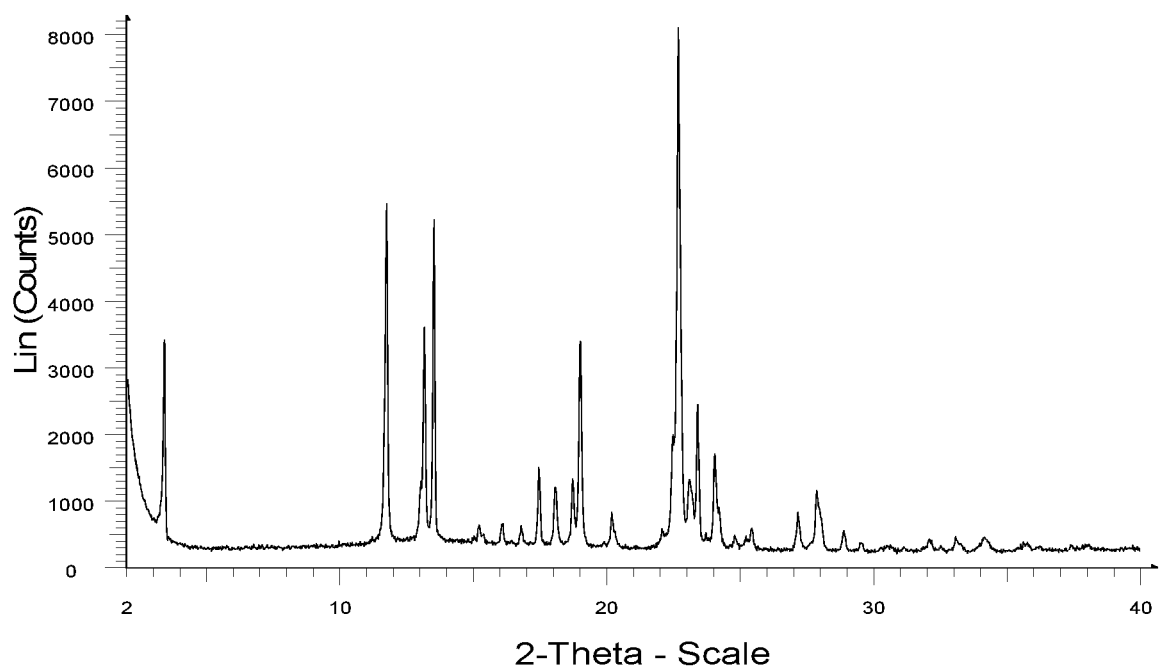

Figure 4: DSC Thermogram of Form B of 7-Fluoro-1-isopropyl-3-methyl-8-[6-[3-(1-piperidyl)propoxy]-3-pyridyl]imidazo[4,5-c]quinolin-2-one
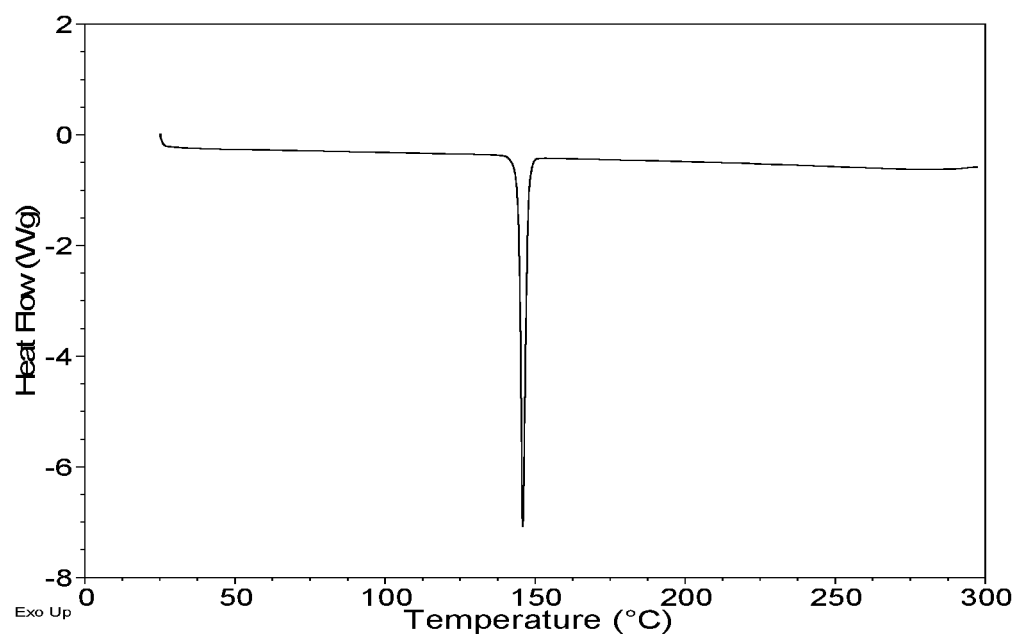

IMIDAZO[4,5-C]QUINOLIN-2-ONE COMPOUNDS AND THEIR USE IN TREATING CANCER

FIELD OF INVENTION

In accordance with 35 U.S.C. 119(a)-(d) and (f), 172, 365(a) and (b), 386(a) and (b), and 37 CFR 1.55 this application claims the benefit of GB Application No. 1516504.6 filed on 17 Sep. 2015.

This specification relates to substituted imidazo[4,5-c] quinolin-2-one compounds and pharmaceutically acceptable salts thereof. These compounds and salts selectively modulate ataxia telangiectasia mutated ("ATM") kinase, and the specification therefore also relates to the use of substituted imidazo[4,5-c]quinolin-2-one compounds and salts thereof to treat or prevent ATM mediated disease, including cancer. The specification further relates to pharmaceutical compositions comprising substituted imidazo[4,5-c]quinolin-2-one compounds and pharmaceutically acceptable salts thereof; kits comprising such compounds and salts; methods of manufacture of such compounds and salts; and intermediates useful in such manufacture.

BACKGROUND

ATM kinase is a serine threonine kinase originally identified as the product of the gene mutated in ataxia telangiectasia. Ataxia telangiectasia is located on human chromosome 11q22-23 and codes for a large protein of about 350 kDa, which is characterized by the presence of a phosphatidylinositol ("PI") 3-kinase-like serine/threonine kinase domain flanked by FRAP-ATM-TRRAP and FATC domains which modulate ATM kinase activity and function. ATM kinase has been identified as a major player of the DNA damage response elicited by double strand breaks. It primarily functions in S/G2/M cell cycle transitions and at collapsed replication forks to initiate cell cycle checkpoints, chromatin modification, HR repair and pro-survival signalling cascades in order to maintain cell integrity after DNA damage (Lavin, M. F.; Rev. Mol. Cell Biol. 200, 759-769).

ATM kinase signalling can be broadly divided into two categories: a canonical pathway, which signals together with the Mre11-Rad50-NBS1 complex from double strand breaks and activates the DNA damage checkpoint, and several non-canonical modes of activation, which are activated by other forms of cellular stress (Cremona et al., Oncogene 2013, 3351-3360).

ATM kinase is rapidly and robustly activated in response to double strand breaks and is reportedly able to phosphorylate in excess of 800 substrates (Matsuoka et al., Science 2007, 1160-1166), coordinating multiple stress response pathways (Kurz and Lees Miller, DNA Repair 2004, 889-900). ATM kinase is present predominantly in the nucleus of the cell in an inactive homodimeric form but autophosphorylates itself on Ser1981 upon sensing a DNA double strand break (canonical pathway), leading to dissociation to a monomer with full kinase activity (Bakkenist et al., Nature 2003, 499-506). This is a critical activation event, and ATM phospho-Ser1981 is therefore both a direct pharmacodynamic and patient selection biomarker for tumour pathway dependency.

ATM kinase responds to direct double strand breaks caused by common anti-cancer treatments such as ionising radiation and topoisomerase-II inhibitors (doxorubicin, etoposide) but also to topoisomerase-I inhibitors (for example irinotecan and topotecan) via single strand break to double strand break conversion during replication. ATM kinase inhibition can potentiate the activity of any these agents, and as a result ATM kinase inhibitors are expected to be of use in the treatment of cancer.

CN102372711A reports certain imidazo[4,5-c]quinolin-2-one compounds which are mentioned to be dual inhibitors of PI 3-kinase α and mammalian target of rapamycin ("mTOR") kinase. Among the compounds reported in CN102372711A are the following:

Certain compounds reported in CN102372711A

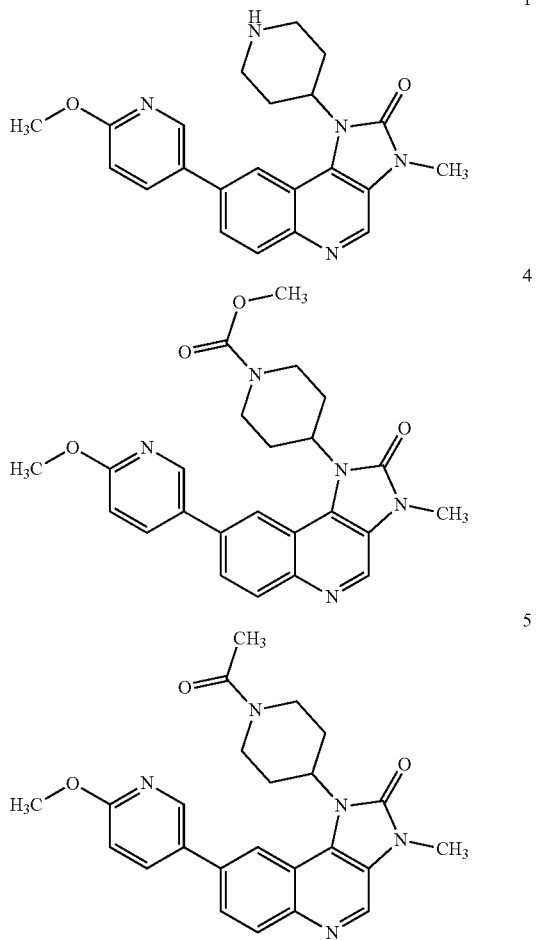

CN102399218A reports certain imidazo[4,5-c]quinolin-2-one compounds which are mentioned to be PI 3-kinase α inhibitors. Among the compounds reported in CN102399218A are the following:

Certain compounds reported in CN102399218A

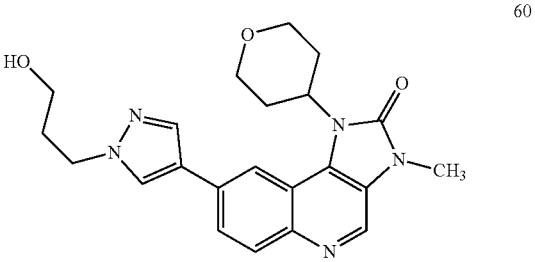

-continued

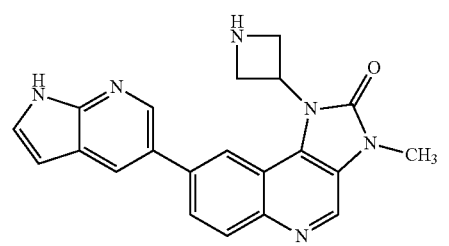

61

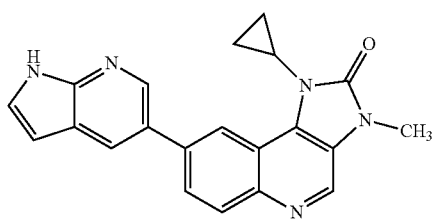

62

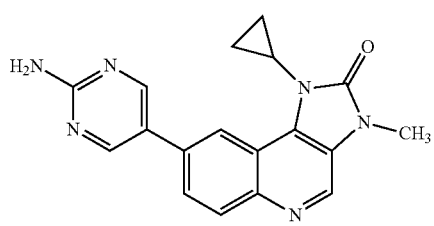

64

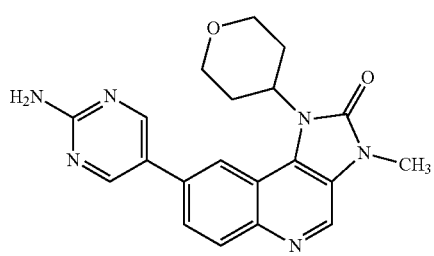

94

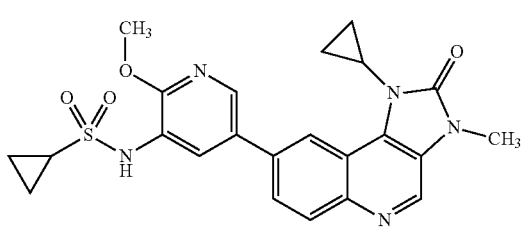

114

While the compounds or CN102372711A and CN 102399218A are reported to possess activity against PI 3-kinase α and in some cases mTOR kinase, there remains a need to develop new compounds that are more effective against different kinase enzymes, such as ATM kinase. There further exists a need for new compounds which act against certain kinase enzymes, like ATM kinase, in a highly selective fashion (i.e. by modulating ATM more effectively than other biological targets).

As demonstrated elsewhere in the specification (for example in the cell based assays described in the experimental section), the compounds of the present specification generally possess very potent ATM kinase inhibitory activity, but much less potent activity against other tyrosine kinase enzymes, such as PI 3-kinase α, mTOR kinase and ataxia telangiectasia and Rad3-related protein ("ATR") kinase. As such, the compounds of the present specification not only inhibit ATM kinase, but can be considered to be highly selective inhibitors of ATM kinase.

As a result of their highly selective nature, the compounds of the present specification are expected to be particularly useful in the treatment of diseases in which ATM kinase is implicated (for example, in the treatment of cancer), but where it is desirable to minimise off-target effects or toxicity that might arise due to the inhibition of other tyrosine kinase enzymes, such as class PI 3-kinase α, mTOR kinase and ATR kinase.

SUMMARY OF INVENTION

Briefly, this specification describes, in part, a compound of Formula (I):

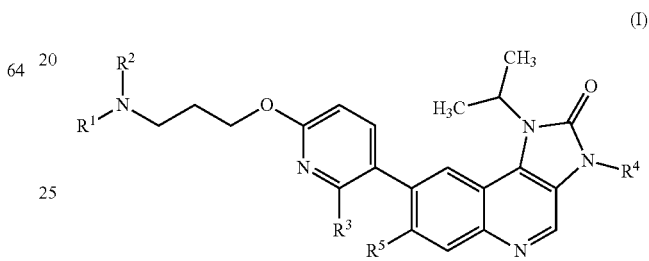

(I)

or a pharmaceutically acceptable salt thereof, where:
$R^1$ is methyl;
$R^2$ is hydro or methyl; or $R^1$ and $R^2$ together with the nitrogen atom to which they are bonded form an azetidinyl, pyrrolidinyl or piperidinyl ring;
$R^3$ is hydro or fluoro;
$R^4$ is hydro or methyl; and
$R^5$ is hydro or fluoro.

This specification also describes, in part, a pharmaceutical composition which comprises a compound of Formula (I), or a pharmaceutically acceptable salt thereof, and at least one pharmaceutically acceptable excipient.

This specification also describes, in part, a compound of Formula (I), or a pharmaceutically acceptable salt thereof, for use in therapy.

This specification also describes, in part, a compound of Formula (I), or a pharmaceutically acceptable salt thereof, for use in the treatment of cancer.

This specification also describes, in part, the use of a compound of Formula (I), or a pharmaceutically acceptable salt thereof, in the manufacture of a medicament for the treatment of cancer.

This specification also describes, in part, a method for treating cancer in a warm blooded animal in need of such treatment, which comprises administering to said warm-blooded animal a therapeutically effective amount of a compound of Formula (I), or a pharmaceutically acceptable salt thereof.

FIGURES

FIG. 1: X-Ray Powder Diffraction Pattern of Form A of 7-Fluoro-1-isopropyl-3-methyl-8-[6-[3-(1-piperidyl)propoxy]-3-pyridyl]imidazo[4,5-c]quinolin-2-one.

FIG. 2: DSC Thermogram of Form A of 7-Fluoro-1-isopropyl-3-methyl-8-[6-[3-(1-piperidyl)propoxy]-3-pyridyl]imidazo[4,5-c]quinolin-2-one.

FIG. 3: X-Ray Powder Diffraction Pattern of Form B of 7-Fluoro-1-isopropyl-3-methyl-8-[6-[3-(1-piperidyl)propoxy]-3-pyridyl]imidazo[4,5-c]quinolin-2-one.

FIG. 4: DSC Thermogram of Form B of 7-Fluoro-1-isopropyl-3-methyl-8-[6-[3-(1-piperidyl)propoxy]-3-pyridyl]imidazo[4,5-c]quinolin-2-one.

DESCRIPTION OF ILLUSTRATIVE EMBODIMENTS

Many embodiments of the invention are detailed throughout the specification and will be apparent to a reader skilled in the art. The invention is not to be interpreted as being limited to any particular embodiment(s) thereof.

In the first embodiment there is provided a compound of Formula (I):

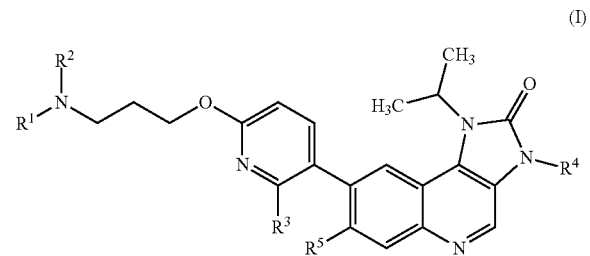

(I)

or a pharmaceutically acceptable salt thereof, where:
$R^1$ is methyl;
$R^2$ is hydro or methyl; or $R^1$ and $R^2$ together with the nitrogen atom to which they are bonded form an azetidinyl, pyrrolidinyl or piperidinyl ring;
$R^3$ is hydro or fluoro;
$R^4$ is hydro or methyl; and
$R^5$ is hydro or fluoro.

A "hydro" group is equivalent to a hydrogen atom. Atoms with a hydro group attached to them can be regarded as unsubstituted.

Where it is mentioned that "$R^1$ and $R^2$ together with the nitrogen atom to which they are bonded form an azetidinyl, pyrrolidinyl or piperidinyl ring", this means the $R^1$ and $R^2$ groups are joined via a carbon-carbon covalent bond to form an unsubstituted alkylene chain of the appropriate length to form the corresponding ring. For example, when $R^1$ and $R^2$ together with the nitrogen atom to which they are bonded form a pyrrolidinyl ring, $R^1$ and $R^2$ together represent an unsubstituted butylene chain which is attached to the relevant nitrogen atom in Formula (I) at both terminal carbons.

The term "pharmaceutically acceptable" is used to specify that an object (for example a salt, dosage form or excipient) is suitable for use in patients. An example list of pharmaceutically acceptable salts can be found in the *Handbook of Pharmaceutical Salts: Properties, Selection and Use*, P. H. Stahl and C. G. Wermuth, editors, Weinheim/Zürich:Wiley-VCH/VHCA, 2002. A suitable pharmaceutically acceptable salt of a compound of Formula (I) is, for example, an acid-addition salt. An acid addition salt of a compound of Formula (I) may be formed by bringing the compound into contact with a suitable inorganic or organic acid under conditions known to the skilled person. An acid addition salt may for example be formed using an inorganic acid selected from the group consisting of hydrochloric acid, hydrobromic acid, sulphuric acid and phosphoric acid. An acid addition salt may also be formed using an organic acid selected from the group consisting of trifluoroacetic acid, citric acid, maleic acid, oxalic acid, acetic acid, formic acid, benzoic acid, fumaric acid, succinic acid, tartaric acid, lactic acid, pyruvic acid, methanesulfonic acid, benzenesulfonic acid and para-toluenesulfonic acid.

Therefore, in one embodiment there is provided a compound of Formula (I) or a pharmaceutically acceptable salt thereof, where the pharmaceutically acceptable salt is a hydrochloric acid, hydrobromic acid, sulphuric acid, phosphoric acid, trifluoroacetic acid, citric acid, maleic acid, oxalic acid, acetic acid, formic acid, benzoic acid, fumaric acid, succinic acid, tartaric acid, lactic acid, pyruvic acid, methanesulfonic acid, benzenesulfonic acid or para-toluenesulfonic acid salt. In one embodiment there is provided a compound of Formula (I) or a pharmaceutically acceptable salt thereof, where the pharmaceutically acceptable salt is a methanesulfonic acid salt. In one embodiment there is provided a compound of Formula (I) or a pharmaceutically acceptable salt thereof, where the pharmaceutically acceptable salt is a mono-methanesulfonic acid salt, i.e. the stoichiometry of the compound of the compound of Formula (I) to methanesulfonic acid is 1:1.

A further embodiment provides any of the embodiments defined herein (for example the embodiment of claim 1) with the proviso that one or more specific Examples (for instance one, two or three specific Examples) selected from the group consisting of Examples 1, 2, 3, 4, 5, 6, 7, 8, 9, 10, 11, 12, 13, 14, 15, 16, 17 and 18 is individually disclaimed.

Some values of variable groups in Formula (I) are as follows. Such values may be used in combination with any of the definitions, claims (for example claim 1), or embodiments defined herein to provide further embodiments.

a) $R^1$ is methyl.
b) $R^2$ is methyl.
c) $R^2$ is hydro.
d) $R^1$ is methyl and $R^2$ is hydro or methyl.
e) $R^1$ and $R^2$ are both methyl.
f) $R^1$ and $R^2$ are both methyl; or $R^1$ and $R^2$ together with the nitrogen atom to which they are bonded form an azetidinyl, pyrrolidinyl or piperidinyl ring.
g) $R^1$ and $R^2$ are both methyl; or $R^1$ and $R^2$ together with the nitrogen atom to which they are bonded form an azetidinyl ring.
h) $R^1$ and $R^2$ are both methyl; or $R^1$ and $R^2$ together with the nitrogen atom to which they are bonded form a pyrrolidinyl ring.
i) $R^1$ and $R^2$ are both methyl; or $R^1$ and $R^2$ together with the nitrogen atom to which they are bonded form a piperidinyl ring.
j) $R^1$ and $R^2$ are both methyl.
k) $R^1$ and $R^2$ together with the nitrogen atom to which they are bonded form an azetidinyl, pyrrolidinyl or piperidinyl ring.
l) $R^1$ and $R^2$ together with the nitrogen atom to which they are bonded form an azetidinyl ring.
m) $R^1$ and $R^2$ together with the nitrogen atom to which they are bonded form a pyrrolidinyl ring.
n) $R^1$ and $R^2$ together with the nitrogen atom to which they are bonded form a piperidinyl ring.
o) $R^3$ and $R^5$ are both hydro.
p) $R^3$ and $R^5$ are both fluoro.
q) $R^3$ is hydro.
r) $R^3$ is fluoro.
s) $R^4$ is hydro.
t) $R^4$ is methyl.
u) $R^5$ is hydro.
v) $R^5$ is fluoro.

In one embodiment there is provided a compound of Formula (I), or a pharmaceutically acceptable salt thereof, where:
R¹ is methyl;
R² is hydro or methyl; or R¹ and R² together with the nitrogen atom to which they are bonded form an azetidinyl, pyrrolidinyl or piperidinyl ring;
R³ is hydro or fluoro;
R⁴ is hydro or methyl; and
R⁵ is hydro or fluoro.

In one embodiment there is provided a compound of Formula (I), or a pharmaceutically acceptable salt thereof, where:
R¹ is methyl;
R² is hydro or methyl;
R³ is hydro;
R⁴ is hydro or methyl; and
R⁵ is hydro.

In one embodiment there is provided a compound of Formula (I), or a pharmaceutically acceptable salt thereof, where the compound is selected from the group consisting of:
8-[6-[3-(Dimethylamino)propoxy]-3-pyridyl]-7-fluoro-1-isopropyl-3-methyl-imidazo[4,5-c]quinolin-2-one;
7-Fluoro-1-isopropyl-3-methyl-8-[6-[3-(1-piperidyl)propoxy]-3-pyridyl]imidazo[4,5-c]quinolin-2-one;
7-Fluoro-1-isopropyl-3-methyl-8-[6-(3-pyrrolidin-1-ylpropoxy)-3-pyridyl]imidazo[4,5-c]quinolin-2-one;
8-[6-[3-(azetidin-1-yl)propoxy]-3-pyridyl]-7-fluoro-1-isopropyl-3-methyl-imidazo[4,5-c]quinolin-2-one;
1-Isopropyl-3-methyl-8-[6-[3-(1-piperidyl)propoxy]-3-pyridyl]imidazo[4,5-c]quinolin-2-one;
8-[6-[3-(dimethylamino)propoxy]-3-pyridyl]-1-isopropyl-3-methyl-imidazo[4,5-c]quinolin-2-one;
1-isopropyl-3-methyl-8-[6-(3-pyrrolidin-1-ylpropoxy)-3-pyridyl]imidazo[4,5-c]quinolin-2-one;
8-[6-[3-(Azetidin-1-yl)propoxy]-3-pyridyl]-1-isopropyl-3-methyl-imidazo[4,5-c]quinolin-2-one;
8-[2-Fluoro-6-[3-(1-piperidyl)propoxy]-3-pyridyl]-1-isopropyl-3-methyl-imidazo[4,5-c]quinolin-2-one;
8-[6-[3-(dimethylamino)propoxy]-2-fluoro-3-pyridyl]-1-isopropyl-3-methyl-imidazo[4,5-c]quinolin-2-one;
8-[6-[3-(dimethylamino)propoxy]-2-fluoro-3-pyridyl]-7-fluoro-1-isopropyl-3-methyl-imidazo[4,5-c]quinolin-2-one;
8-[2-fluoro-6-(3-pyrrolidin-1-ylpropoxy)-3-pyridyl]-1-isopropyl-3-methyl-imidazo[4,5-c]quinolin-2-one;
7-fluoro-8-[2-fluoro-6-(3-pyrrolidin-1-ylpropoxy)-3-pyridyl]-1-isopropyl-3-methyl-imidazo[4,5-c]quinolin-2-one;
7-fluoro-8-[2-fluoro-6-[3-(1-piperidyl)propoxy]-3-pyridyl]-1-isopropyl-3-methyl-imidazo[4,5-c]quinolin-2-one;
8-[6-[3-(azetidin-1-yl)propoxy]-2-fluoro-3-pyridyl]-1-isopropyl-3-methyl-imidazo[4,5-c]quinolin-2-one;
8-[6-[3-(azetidin-1-yl)propoxy]-2-fluoro-3-pyridyl]-7-fluoro-1-isopropyl-3-methyl-imidazo[4,5-c]quinolin-2-one;
8-[6-[3-(Dimethylamino)propoxy]-3-pyridyl]-7-fluoro-1-isopropyl-3H-imidazo[4,5-c]quinolin-2-one; and
7-Fluoro-1-isopropyl-8-[6-[3-(1-piperidyl)propoxy]-3-pyridyl]-3H-imidazo[4,5-c]quinolin-2-one.

In one embodiment there is provided 7-fluoro-1-isopropyl-3-methyl-8-[6-[3-(1-piperidyl)propoxy]-3-pyridyl]imidazo[4,5-c]quinolin-2-one, or a pharmaceutically acceptable salt thereof.

In one embodiment there is provided 7-fluoro-1-isopropyl-3-methyl-8-[6-[3-(1-piperidyl)propoxy]-3-pyridyl]imidazo[4,5-c]quinolin-2-one.

In one embodiment there is provided a pharmaceutically acceptable salt of 7-fluoro-1-isopropyl-3-methyl-8-[6-[3-(1-piperidyl)propoxy]-3-pyridyl]imidazo[4,5-c]quinolin-2-one.

In one embodiment there is provided 8-[6-[3-(azetidin-1-yl)propoxy]-3-pyridyl]-1-isopropyl-3-methyl-imidazo[4,5-c]quinolin-2-one, or a pharmaceutically acceptable salt thereof.

In one embodiment there is provided 8-[6-[3-(azetidin-1-yl)propoxy]-3-pyridyl]-1-isopropyl-3-methyl-imidazo[4,5-c]quinolin-2-one.

In one embodiment there is provided a pharmaceutically acceptable salt of 8-[6-[3-(azetidin-1-yl)propoxy]-3-pyridyl]-1-isopropyl-3-methyl-imidazo[4,5-c]quinolin-2-one.

In one embodiment there is provided 8-[6-[3-(dimethylamino)propoxy]-3-pyridyl]-7-fluoro-1-isopropyl-3-methyl-imidazo[4,5-c]quinolin-2-one, or a pharmaceutically acceptable salt thereof.

In one embodiment there is provided 8-[6-[3-(dimethylamino)propoxy]-3-pyridyl]-7-fluoro-1-isopropyl-3-methyl-imidazo[4,5-c]quinolin-2-one.

In one embodiment there is provided a pharmaceutically acceptable salt of 8-[6-[3-(dimethylamino)propoxy]-3-pyridyl]-7-fluoro-1-isopropyl-3-methyl-imidazo[4,5-c]quinolin-2-one.

In one embodiment there is provided 7-fluoro-1-isopropyl-3-methyl-8-[6-[3-(1-oxidopiperidin-1-ium-1-yl)propoxy]-3-pyridyl]imidazo[4,5-c]quinolin-2-one, or a pharmaceutically acceptable salt thereof.

In one embodiment there is provided 7-fluoro-1-isopropyl-3-methyl-8-[6-[3-(1-oxidopiperidin-1-ium-1-yl)propoxy]-3-pyridyl]imidazo[4,5-c]quinolin-2-one.

In one embodiment there is provided a pharmaceutically acceptable salt of 7-fluoro-1-isopropyl-3-methyl-8-[6-[3-(1-oxidopiperidin-1-ium-1-yl)propoxy]-3-pyridyl]imidazo[4,5-c]quinolin-2-one.

Compounds and salts described in this specification may exist in solvated forms and unsolvated forms. For example, a solvated form may be a hydrated form, such as a hemi-hydrate, a mono-hydrate, a di-hydrate, a tri-hydrate or an alternative quantity thereof. The invention encompasses all such solvated and unsolvated forms of compounds of Formula (I), particularly to the extent that such forms possess ATM kinase inhibitory activity, as for example measured using the tests described herein.

Atoms of the compounds and salts described in this specification may exist as their isotopes. The invention encompasses all compounds of Formula (I) where an atom is replaced by one or more of its isotopes (for example a compound of Formula (I) where one or more carbon atom is an $^{11}$C or $^{13}$C carbon isotope, or where one or more hydrogen atoms is a $^{2}$H or $^{3}$H isotope).

Compounds and salts described in this specification may exist as a mixture of tautomers. "Tautomers" are structural isomers that exist in equilibrium resulting from the migration of a hydrogen atom. The invention includes all tautomers of compounds of Formula (I) particularly to the extent that such tautomers possess ATM kinase inhibitory activity.

Compounds and salts described in this specification may be crystalline, and may exhibit one or more crystalline forms. The invention encompasses any crystalline or amorphous form of a compound of Formula (I), or mixture of such forms, which possesses ATM kinase inhibitory activity.

It is generally known that crystalline materials may be characterised using conventional techniques such as X-Ray Powder Diffraction (XRPD), Differential Scanning Calorimetry (DSC), Thermal Gravimetric Analysis (TGA), Diffuse Reflectance Infrared Fourier Transform (DRIFT) spectroscopy, Near Infrared (NIR) spectroscopy, solution and/or solid state nuclear magnetic resonance spectroscopy. The water content of crystalline materials may be determined by Karl Fischer analysis.

The crystalline forms described herein provide XRPD patterns substantially the same as the XRPD patterns shown in the Figures, and have the various 2-theta values as shown in the Tables included herein. One skilled in the art will understand that an XRPD pattern or diffractogram may be obtained which has one or more measurement errors depending on the recording conditions, such as the equipment or machine used. Similarly, it is generally known that intensities in an XRPD pattern may fluctuate depending on measurement conditions or sample preparation as a result of preferred orientation. Persons skilled in the art of XRPD will further realise that the relative intensity of peaks can also be affected by, for example, grains above 30 µm in size and non-unitary aspect ratios. The skilled person understands that the position of reflections can be affected by the precise height at which the sample sits in the diffractometer, and also the zero calibration of the diffractometer. The surface planarity of the sample may also have a small effect.

As a result of these considerations, the diffraction pattern data presented are not to be taken as absolute values (Jenkins, R & Snyder, R. L. 'Introduction to X-Ray Powder Difractometry' John Wiley & Sons 1996; Bunn, C. W. (1948), 'Chemical Crystallography', Clarendon Press, London; Klug, H. P. & Alexander, L. E. (1974), 'X-Ray Diffraction Procedures'). It should correspondingly be understood that the solid forms are not limited to the crystals that provide XRPD patterns that are identical to the XRPD pattern shown in the Figures, and any crystals providing XRPD patterns substantially the same as those shown in the Figures fall within the scope of the invention. A person skilled in the art of XRPD is able to judge the substantial identity of XRPD patterns. Generally, a measurement error of a diffraction angle in an XRPD is approximately plus or minus 0.2° 2-theta, and such degree of a measurement error should be taken into account when considering the X-ray powder diffraction pattern in the Figures and when reading data contained in the Tables included herein.

The compound of Example 2 exhibits crystalline properties, and one crystalline form has been characterised.

Therefore, in one embodiment there is provided Form A of 7-fluoro-1-isopropyl-3-methyl-8-[6-[3-(1-piperidyl)propoxy]-3-pyridyl]imidazo[4,5-c]quinolin-2-one.

In one embodiment there is provided a crystalline form, Form A of 7-fluoro-1-isopropyl-3-methyl-8-[6-[3-(1-piperidyl)propoxy]-3-pyridyl]imidazo[4,5-c]quinolin-2-one, which has an X-ray powder diffraction pattern with at least one specific peak at about 2-theta=22.7°.

In one embodiment there is provided a crystalline form, Form A of 7-fluoro-1-isopropyl-3-methyl-8-[6-[3-(1-piperidyl)propoxy]-3-pyridyl]imidazo[4,5-c]quinolin-2-one, which has an X-ray powder diffraction pattern with at least one specific peak at about 2-theta=23.4°.

In one embodiment there is provided a crystalline form, Form A of 7-fluoro-1-isopropyl-3-methyl-8-[6-[3-(1-piperidyl)propoxy]-3-pyridyl]imidazo[4,5-c]quinolin-2-one, which has an X-ray powder diffraction pattern with at least two specific peaks at about 2-theta=22.7 and 23.4°.

In one embodiment there is provided a crystalline form, Form A of 7-fluoro-1-isopropyl-3-methyl-8-[6-[3-(1-piperidyl)propoxy]-3-pyridyl]imidazo[4,5-c]quinolin-2-one, which has an X-ray powder diffraction pattern with at least two specific peaks at about 2-theta=3.7 and 14.8°.

In one embodiment there is provided a crystalline form, Form A of 7-fluoro-1-isopropyl-3-methyl-8-[6-[3-(1-piperidyl)propoxy]-3-pyridyl]imidazo[4,5-c]quinolin-2-one, which has an X-ray powder diffraction pattern with specific peaks at about 2-theta=3.7, 11.3, 13.1, 14.8, 18.0, 18.4, 19.4, 21.0, 22.3 and 23.2°.

In one embodiment there is provided a crystalline form, Form A of 7-fluoro-1-isopropyl-3-methyl-8-[6-[3-(1-piperidyl)propoxy]-3-pyridyl]imidazo[4,5-c]quinolin-2-one which has an X-ray powder diffraction pattern substantially the same as the X-ray powder diffraction pattern shown in FIG. 1.

In one embodiment there is provided a crystalline form, Form A of 7-fluoro-1-isopropyl-3-methyl-8-[6-[3-(1-piperidyl)propoxy]-3-pyridyl]imidazo[4,5-c]quinolin-2-one, which has an X-ray powder diffraction pattern with at least one specific peak at 2-theta=22.7° plus or minus 0.2° 2-theta.

In one embodiment there is provided a crystalline form, Form A of 7-fluoro-1-isopropyl-3-methyl-8-[6-[3-(1-piperidyl)propoxy]-3-pyridyl]imidazo[4,5-c]quinolin-2-one, which has an X-ray powder diffraction pattern with at least one specific peak at 2-theta=23.4° plus or minus 0.2° 2-theta.

In one embodiment there is provided a crystalline form, Form A of 7-fluoro-1-isopropyl-3-methyl-8-[6-[3-(1-piperidyl)propoxy]-3-pyridyl]imidazo[4,5-c]quinolin-2-one, which has an X-ray powder diffraction pattern with at least two specific peaks at 2-theta=22.7 and 23.4° plus or minus 0.2° 2-theta.

In one embodiment there is provided a crystalline form, Form A of 7-fluoro-1-isopropyl-3-methyl-8-[6-[3-(1-piperidyl)propoxy]-3-pyridyl]imidazo[4,5-c]quinolin-2-one, which has an X-ray powder diffraction pattern with at least one specific peak at 2-theta=3.7° plus or minus 0.2° 2-theta.

In one embodiment there is provided a crystalline form, Form A of 7-fluoro-1-isopropyl-3-methyl-8-[6-[3-(1-piperidyl)propoxy]-3-pyridyl]imidazo[4,5-c]quinolin-2-one, which has an X-ray powder diffraction pattern with at least one specific peak at 2-theta=14.8° plus or minus 0.2° 2-theta.

In one embodiment there is provided a crystalline form, Form A of 7-fluoro-1-isopropyl-3-methyl-8-[6-[3-(1-piperidyl)propoxy]-3-pyridyl]imidazo[4,5-c]quinolin-2-one, which has an X-ray powder diffraction pattern with at least two specific peaks at 2-theta=3.7 and 14.8° plus or minus 0.2° 2-theta.

In one embodiment there is provided a crystalline form, Form A of 7-fluoro-1-isopropyl-3-methyl-8-[6-[3-(1-piperidyl)propoxy]-3-pyridyl]imidazo[4,5-c]quinolin-2-one, which has an X-ray powder diffraction pattern with specific peaks at 2-theta=3.7, 11.3, 13.1, 14.8, 18.0, 18.4, 19.4, 21.0, 22.3 and 23.2° plus or minus 0.2° 2-theta.

DSC analysis of Form A of 7-fluoro-1-isopropyl-3-methyl-8-[6-[3-(1-piperidyl)propoxy]-3-pyridyl]imidazo[4,5-c]quinolin-2-one shows a melting endotherm with an onset of 141.5° C. and a peak at 144.2° C. (FIG. 2).

A person skilled in the art understands that the value or range of values observed in a particular compound's DSC Thermogram will show variation between batches of different purities. Therefore, whilst for one compound the range may be small, for others the range may be quite large. Generally, a measurement error of a diffraction angle in DSC thermal events is approximately plus or minus 5° C., and such degree of a measurement error should be taken into account when considering the DSC data included herein.

Therefore, in one embodiment there is provided a crystalline form, Form A of 7-fluoro-1-isopropyl-3-methyl-8-[6-[3-(1-piperidyl)propoxy]-3-pyridyl]imidazo[4,5-c]quinolin-2-one which has a DSC endotherm with an onset of melting at about 141.5° C. and a peak at about 144.2° C.

Therefore, in one embodiment there is provided a crystalline form, Form A of 7-fluoro-1-isopropyl-3-methyl-8-[6-[3-(1-piperidyl)propoxy]-3-pyridyl]imidazo[4,5-c]quinolin-2-one which has a DSC endotherm with an onset of melting at 141.5° C. plus or minus 5° C. and a peak at 144.2° C. plus or minus 5° C.

In one embodiment there is provided a crystalline form, Form A of 7-fluoro-1-isopropyl-3-methyl-8-[6-[3-(1-piperidyl)propoxy]-3-pyridyl]imidazo[4,5-c]quinolin-2-one which has a DSC endotherm with an onset of melting at 141.5° C. and a peak at 144.2° C.

In one embodiment there is provided a crystalline form, Form A of 7-fluoro-1-isopropyl-3-methyl-8-[6-[3-(1-piperidyl)propoxy]-3-pyridyl]imidazo[4,5-c]quinolin-2-one which has a DSC thermogram substantially as shown in FIG. 2.

In one embodiment there is provided Form B of 7-fluoro-1-isopropyl-3-methyl-8-[6-[3-(1-piperidyl)propoxy]-3-pyridyl]imidazo[4,5-c]quinolin-2-one.

In one embodiment there is provided a crystalline form, Form B of 7-fluoro-1-isopropyl-3-methyl-8-[6-[3-(1-piperidyl)propoxy]-3-pyridyl]imidazo[4,5-c]quinolin-2-one, which has an X-ray powder diffraction pattern with at least one specific peak at about 2-theta=14.8°.

In one embodiment there is provided a crystalline form, Form B of 7-fluoro-1-isopropyl-3-methyl-8-[6-[3-(1-piperidyl)propoxy]-3-pyridyl]imidazo[4,5-c]quinolin-2-one, which has an X-ray powder diffraction pattern with at least one specific peak at about 2-theta=21.0°.

In one embodiment there is provided a crystalline form, Form B of 7-fluoro-1-isopropyl-3-methyl-8-[6-[3-(1-piperidyl)propoxy]-3-pyridyl]imidazo[4,5-c]quinolin-2-one, which has an X-ray powder diffraction pattern with at least two specific peaks at about 2-theta=14.8 and 21.0°.

In one embodiment there is provided a crystalline form, Form B of 7-fluoro-1-isopropyl-3-methyl-8-[6-[3-(1-piperidyl)propoxy]-3-pyridyl]imidazo[4,5-c]quinolin-2-one, which has an X-ray powder diffraction pattern with at least two specific peaks at about 2-theta=3.4 and 11.7°.

In one embodiment there is provided a crystalline form, Form B of 7-fluoro-1-isopropyl-3-methyl-8-[6-[3-(1-piperidyl)propoxy]-3-pyridyl]imidazo[4,5-c]quinolin-2-one, which has an X-ray powder diffraction pattern with specific peaks at about 2-theta=3.4, 11.7, 13.1, 13.5, 17.5, 18.1, 19.0, 22.7, 23.4 and 24.0°.

In one embodiment there is provided a crystalline form, Form B of 7-fluoro-1-isopropyl-3-methyl-8-[6-[3-(1-piperidyl)propoxy]-3-pyridyl]imidazo[4,5-c]quinolin-2-one which has an X-ray powder diffraction pattern substantially the same as the X-ray powder diffraction pattern shown in FIG. 3.

In one embodiment there is provided a crystalline form, Form B of 7-fluoro-1-isopropyl-3-methyl-8-[6-[3-(1-piperidyl)propoxy]-3-pyridyl]imidazo[4,5-c]quinolin-2-one, which has an X-ray powder diffraction pattern with at least one specific peak at 2-theta=14.8° plus or minus 0.2° 2-theta.

In one embodiment there is provided a crystalline form, Form B of 7-fluoro-1-isopropyl-3-methyl-8-[6-[3-(1-piperidyl)propoxy]-3-pyridyl]imidazo[4,5-c]quinolin-2-one, which has an X-ray powder diffraction pattern with at least one specific peak at 2-theta=21.0° plus or minus 0.2° 2-theta.

In one embodiment there is provided a crystalline form, Form B of 7-fluoro-1-isopropyl-3-methyl-8-[6-[3-(1-piperidyl)propoxy]-3-pyridyl]imidazo[4,5-c]quinolin-2-one, which has an X-ray powder diffraction pattern with at least two specific peaks at 2-theta=14.8 and 21.0° plus or minus 0.2° 2-theta.

In one embodiment there is provided a crystalline form, Form B of 7-fluoro-1-isopropyl-3-methyl-8-[6-[3-(1-piperidyl)propoxy]-3-pyridyl]imidazo[4,5-c]quinolin-2-one, which has an X-ray powder diffraction pattern with at least one specific peak at 2-theta=3.4° plus or minus 0.2° 2-theta.

In one embodiment there is provided a crystalline form, Form B of 7-fluoro-1-isopropyl-3-methyl-8-[6-[3-(1-piperidyl)propoxy]-3-pyridyl]imidazo[4,5-c]quinolin-2-one, which has an X-ray powder diffraction pattern with at least one specific peak at 2-theta=11.7° plus or minus 0.2° 2-theta.

In one embodiment there is provided a crystalline form, Form B of 7-fluoro-1-isopropyl-3-methyl-8-[6-[3-(1-piperidyl)propoxy]-3-pyridyl]imidazo[4,5-c]quinolin-2-one, which has an X-ray powder diffraction pattern with at least two specific peaks at 2-theta=3.4 and 11.7° plus or minus 0.2° 2-theta.

In one embodiment there is provided a crystalline form, Form B of 7-fluoro-1-isopropyl-3-methyl-8-[6-[3-(1-piperidyl)propoxy]-3-pyridyl]imidazo[4,5-c]quinolin-2-one, which has an X-ray powder diffraction pattern with specific peaks at 2-theta=3.4, 11.7, 13.1, 13.5, 17.5, 18.1, 19.0, 22.7, 23.4 and 24.0° plus or minus 0.2° 2-theta.

DSC analysis of Form B of 7-fluoro-1-isopropyl-3-methyl-8-[6-[3-(1-piperidyl)propoxy]-3-pyridyl]imidazo[4,5-c]quinolin-2-one shows a melting endotherm with an onset of 144.7° C. and a peak at 145.8° C. (FIG. 4).

Therefore, in one embodiment there is provided a crystalline form, Form B of 7-fluoro-1-isopropyl-3-methyl-8-[6-[3-(1-piperidyl)propoxy]-3-pyridyl]imidazo[4,5-c]quinolin-2-one which has a DSC endotherm with an onset of melting at about 144.7° C. and a peak at about 145.8° C.

Therefore, in one embodiment there is provided a crystalline form, Form B of 7-fluoro-1-isopropyl-3-methyl-8-[6-[3-(1-piperidyl)propoxy]-3-pyridyl]imidazo[4,5-c]quinolin-2-one which has a DSC endotherm with an onset of melting at 144.7° C. plus or minus 5° C. and a peak at 145.8° C. plus or minus 5° C.

In one embodiment there is provided a crystalline form, Form B of 7-fluoro-1-isopropyl-3-methyl-8-[6-[3-(1-piperidyl)propoxy]-3-pyridyl]imidazo[4,5-c]quinolin-2-one which has a DSC endotherm with an onset of melting at 144.7° C. and a peak at 145.8° C.

In one embodiment there is provided a crystalline form, Form B of 7-fluoro-1-isopropyl-3-methyl-8-[6-[3-(1-piperidyl)propoxy]-3-pyridyl]imidazo[4,5-c]quinolin-2-one which has a DSC thermogram substantially as shown in FIG. 4.

When it is stated that an embodiment relates to a crystalline form, the degree of crystallinity may be greater than about 60%. In some embodiments the degree of crystallinity is greater than about 80%. In some embodiments the degree of crystallinity is greater than about 90%. In some embodiments the degree of crystallinity is greater than about 95%. In some embodiments the degree of crystallinity is greater than about 98%. Compounds of Formula (I) may for example be prepared by the reaction of a compound of Formula (II):

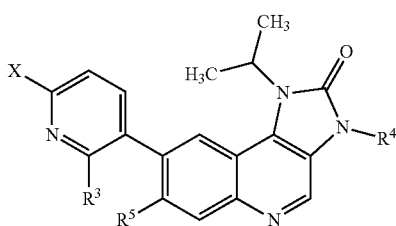

(II)

or a salt thereof, where $R^3$, $R^4$ and $R^5$ are as defined in any of the embodiments herein and X is a leaving group (for example a halogen atom, or alternatively a fluorine atom) with a compound of formula (III):

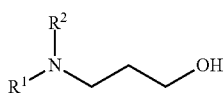

(III)

or a salt thereof, where $R^1$ and $R^2$ are as defined in any of the embodiments herein. The reaction is conveniently performed in a suitable solvent (for example DMF, DMA or THF) and in the presence of a base (for example sodium hydride) at a suitable temperature (for example a temperature in the range of about 20-50° C.).

Compounds of Formula (II), and salts thereof, are therefore useful as intermediates in the preparation of the compounds of Formula (I) and provide a further embodiment. In one embodiment there is provided a compound of Formula (II), or a salt thereof, where:

$R^3$ is hydro or fluoro;
$R^4$ is hydro or methyl;
$R^5$ is hydro or fluoro; and
X is a leaving group. In one embodiment X is a halogen atom or a triflate group. In one embodiment X is a fluorine atom.

In one embodiment there is provided 7-fluoro-8-(6-fluoro-3-pyridyl)-1-isopropyl-3-methyl-imidazo[4,5-c]quinolin-2-one, or a salt thereof.

In one embodiment there is provided 8-(6-fluoro-3-pyridyl)-1-isopropyl-3-methyl-imidazo[4,5-c]quinolin-2-one, or a salt thereof.

In any of the embodiments where a compound of Formula (II) or a salt thereof is mentioned it is to be understood that such salts do not need to be pharmaceutically acceptable salts. A suitable salt of a compound of Formula (II) is, for example, an acid-addition salt. An acid addition salt of a compound of Formula (II) may be formed by bringing the compound into contact with a suitable inorganic or organic acid under conditions known to the skilled person. An acid addition salt may for example be formed using an inorganic acid selected from the group consisting of hydrochloric acid, hydrobromic acid, sulphuric acid and phosphoric acid. An acid addition salt may also be formed using an organic acid selected from the group consisting of trifluoroacetic acid, citric acid, maleic acid, oxalic acid, acetic acid, formic acid, benzoic acid, fumaric acid, succinic acid, tartaric acid, lactic acid, pyruvic acid, methanesulfonic acid, benzenesulfonic acid and para-toluenesulfonic acid.

Therefore, in one embodiment there is provided a compound of Formula (II) or a salt thereof, where the salt is a hydrochloric acid, hydrobromic acid, sulphuric acid, phosphoric acid, trifluoroacetic acid, citric acid, maleic acid, oxalic acid, acetic acid, formic acid, benzoic acid, fumaric acid, succinic acid, tartaric acid, lactic acid, pyruvic acid, methanesulfonic acid, benzenesulfonic acid or para-toluenesulfonic acid salt.

The compounds of Formula (II) may for example be prepared by the reaction of a compound of Formula (IV):

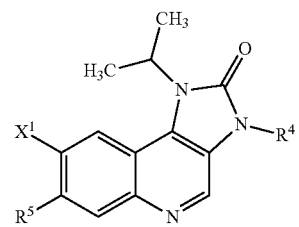

(IV)

where $R^4$ and $R^5$ are as defined in any of the embodiments herein and $X^1$ is a leaving group (for example an iodine, bromine, or chlorine atom or a triflate group, or alternatively a bromine atom) with a compound of formula (V):

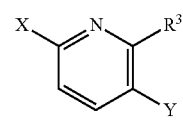

(V)

or a salt thereof, where $R^3$ and X are as defined in any of the embodiments herein and Y is a boronic acid, boronic ester or potassium trifluoroborate group (for example boronic acid, boronic acid pinacol ester, or potassium trifluoroborate). The reaction may be performed under standard conditions well known to those skilled in the art, for example in the presence of a palladium source (for example tetrakis triphenylphosphine palladium or palladium(II) acetate), optionally a phosphine ligand (for example Xantphos or S-phos), and a suitable base (for example cesium carbonate or triethylamine).

Compounds of Formula (IV) are therefore useful as intermediates in the preparation of the compounds of Formula (I) and provide a further embodiment. In one embodiment there is provided a compound of Formula (IV), or a salt thereof, where:

$R^4$ is hydro or methyl;
$R^5$ is hydro or fluoro; and
$X^1$ is a leaving group. In one embodiment $X^1$ is an iodine, bromine, or chlorine atom or a triflate group. In one embodiment $X^1$ is a bromine atom.

In one embodiment there is provided 8-bromo-7-fluoro-1-isopropyl-3-methyl-imidazo[4,5-c]quinolin-2-one, or a salt thereof.

In one embodiment there is provided 8-bromo-1-isopropyl-3-methyl-imidazo[4,5-c]quinolin-2-one, or a salt thereof.

Compounds of formula (IV) can be prepared by methods similar to those shown in the Examples section.

Compounds of Formula (I) may also be prepared by the reaction of a compound of Formula (IV) as described above with a compound of formula (VI):

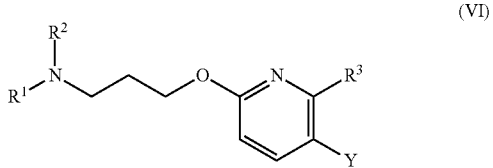

(VI)

where $R^1$, $R^2$ and $R^3$ are as defined in any of the embodiments herein and Y is a boronic acid, boronic ester or potassium trifluoroborate group (for example boronic acid, boronic acid pinacol ester, or potassium trifluoroborate). The reaction may be performed under standard conditions well known to those skilled in the art, for example in the presence of a palladium source (for example tetrakis triphenylphosphine palladium or palladium(II) acetate), optionally a phosphine ligand (for example Xantphos or S-phos), and a suitable base (for example cesium carbonate or triethylamine).

Compounds of formula (VI) can be prepared by methods similar to those shown in the Examples section.

In one embodiment there is provided any one of the novel intermediates described in the experimental section.

As a result of their ATM kinase inhibitory activity, the compounds of Formula (I), and pharmaceutically acceptable salts thereof are expected to be useful in therapy, for example in the treatment of diseases or medical conditions mediated at least in part by ATM kinase, including cancer.

Where "cancer" is mentioned, this includes both non-metastatic cancer and also metastatic cancer, such that treating cancer involves treatment of both primary tumours and also tumour metastases.

"ATM kinase inhibitory activity" refers to a decrease in the activity of ATM kinase as a direct or indirect response to the presence of a compound of Formula (I), or pharmaceutically acceptable salt thereof, relative to the activity of ATM kinase in the absence of compound of Formula (I), or pharmaceutically acceptable salt thereof. Such a decrease in activity may be due to the direct interaction of the compound of Formula (I), or pharmaceutically acceptable salt thereof with ATM kinase, or due to the interaction of the compound of Formula (I), or pharmaceutically acceptable salt thereof with one or more other factors that in turn affect ATM kinase activity. For example, the compound of Formula (I), or pharmaceutically acceptable salt thereof may decrease ATM kinase by directly binding to the ATM kinase, by causing (directly or indirectly) another factor to decrease ATM kinase activity, or by (directly or indirectly) decreasing the amount of ATM kinase present in the cell or organism.

The term "therapy" is intended to have its normal meaning of dealing with a disease in order to entirely or partially relieve one, some or all of its symptoms, or to correct or compensate for the underlying pathology. The term "therapy" also includes "prophylaxis" unless there are specific indications to the contrary. The terms "therapeutic" and "therapeutically" should be interpreted in a corresponding manner.

The term "prophylaxis" is intended to have its normal meaning and includes primary prophylaxis to prevent the development of the disease and secondary prophylaxis whereby the disease has already developed and the patient is temporarily or permanently protected against exacerbation or worsening of the disease or the development of new symptoms associated with the disease.

The term "treatment" is used synonymously with "therapy". Similarly the term "treat" can be regarded as "applying therapy" where "therapy" is as defined herein.

In one embodiment there is provided a compound of Formula (I), or a pharmaceutically acceptable salt thereof, for use in therapy.

In one embodiment there is provided the use of the compound of Formula (I), or a pharmaceutically acceptable salt thereof, for the manufacture of a medicament.

In one embodiment there is provided a compound of Formula (I), or a pharmaceutically acceptable salt thereof, for use in the treatment of a disease mediated by ATM kinase. In one embodiment, said disease mediated by ATM kinase is cancer. In one embodiment, said cancer is selected from the group consisting of colorectal cancer, glioblastoma, gastric cancer, ovarian cancer, diffuse large B-cell lymphoma, chronic lymphocytic leukaemia, acute myeloid leukaemia, head and neck squamous cell carcinoma, breast cancer, hepatocellular carcinoma, small cell lung cancer and non-small cell lung cancer. In one embodiment, said cancer is selected from the group consisting of colorectal cancer, glioblastoma, gastric cancer, ovarian cancer, diffuse large B-cell lymphoma, chronic lymphocytic leukaemia, head and neck squamous cell carcinoma and lung cancer. In one embodiment, said cancer is colorectal cancer.

In one embodiment there is provided a compound of Formula (I), or a pharmaceutically acceptable salt thereof, for use in the treatment of cancer.

In one embodiment there is provided a compound of Formula (I), or a pharmaceutically acceptable salt thereof, for use in the treatment of Huntingdon's disease.

In one embodiment there is provided a compound of Formula (I), or a pharmaceutically acceptable salt thereof, for use as a neuroprotective agent.

A "neuroprotective agent" is an agent that aids relative preservation of neuronal structure and/or function.

In one embodiment there is provided the use of the compound of Formula (I), or a pharmaceutically acceptable salt thereof, for the manufacture of a medicament for the treatment of a disease mediated by ATM kinase. In one embodiment, said disease mediated by ATM kinase is cancer. In one embodiment, said cancer is selected from the group consisting of colorectal cancer, glioblastoma, gastric cancer, ovarian cancer, diffuse large B-cell lymphoma, chronic lymphocytic leukaemia, acute myeloid leukaemia, head and neck squamous cell carcinoma, breast cancer, hepatocellular carcinoma, small cell lung cancer and non-small cell lung cancer. In one embodiment, said cancer is selected from the group consisting of colorectal cancer, glioblastoma, gastric cancer, ovarian cancer, diffuse large B-cell lymphoma, chronic lymphocytic leukaemia, head and neck squamous cell carcinoma and lung cancer. In one embodiment, said cancer is colorectal cancer.

In one embodiment there is provided the use of the compound of Formula (I), or a pharmaceutically acceptable salt thereof, for the manufacture of a medicament for the treatment of cancer.

In one embodiment there is provided the use of the compound of Formula (I), or a pharmaceutically acceptable salt thereof, for the manufacture of a medicament for the treatment of Huntingdon's disease.

In one embodiment there is provided the use of the compound of Formula (I), or a pharmaceutically acceptable salt thereof, for the manufacture of a medicament for use as a neuroprotective agent.

In one embodiment there is provided a method for treating a disease in which inhibition of ATM kinase is beneficial in a warm-blooded animal in need of such treatment, which comprises administering to said warm-blooded animal a therapeutically effective amount of a compound of Formula (I), or a pharmaceutically acceptable salt thereof. In one embodiment, said disease is cancer. In one embodiment, said cancer is selected from the group consisting of colorectal cancer, glioblastoma, gastric cancer, ovarian cancer, diffuse large B-cell lymphoma, chronic lymphocytic leukaemia, acute myeloid leukaemia, head and neck squamous cell carcinoma, breast cancer, hepatocellular carcinoma, small cell lung cancer and non-small cell lung cancer. In one embodiment, said cancer is selected from the group consisting of colorectal cancer, glioblastoma, gastric cancer, ovarian cancer, diffuse large B-cell lymphoma, chronic lymphocytic leukaemia, head and neck squamous cell carcinoma and lung cancer. In one embodiment, said cancer is colorectal cancer.

In any embodiment, a disease in which inhibition of ATM kinase is beneficial may be Huntingdon' disease.

In one embodiment there is provided a method for effecting neuroprotection in a warm-blooded animal in need of such treatment, which comprises administering to said warm-blooded animal a therapeutically effective amount of a compound of Formula (I), or a pharmaceutically acceptable salt thereof.

The term "therapeutically effective amount" refers to an amount of a compound of Formula (I) as described in any of the embodiments herein which is effective to provide "therapy" in a subject, or to "treat" a disease or disorder in a subject. In the case of cancer, the therapeutically effective amount may cause any of the changes observable or measurable in a subject as described in the definition of "therapy", "treatment" and "prophylaxis" above. For example, the effective amount can reduce the number of cancer or tumour cells; reduce the overall tumour size; inhibit or stop tumour cell infiltration into peripheral organs including, for example, the soft tissue and bone; inhibit and stop tumour metastasis; inhibit and stop tumour growth; relieve to some extent one or more of the symptoms associated with the cancer; reduce morbidity and mortality; improve quality of life; or a combination of such effects. An effective amount may be an amount sufficient to decrease the symptoms of a disease responsive to inhibition of ATM kinase activity. For cancer therapy, efficacy in-vivo can, for example, be measured by assessing the duration of survival, time to disease progression (TTP), the response rates (RR), duration of response, and/or quality of life. As recognized by those skilled in the art, effective amounts may vary depending on route of administration, excipient usage, and co-usage with other agents. For example, where a combination therapy is used, the amount of the compound of formula (I) or pharmaceutically acceptable salt described in this specification and the amount of the other pharmaceutically active agent(s) are, when combined, jointly effective to treat a targeted disorder in the animal patient. In this context, the combined amounts are in a "therapeutically effective amount" if they are, when combined, sufficient to decrease the symptoms of a disease responsive to inhibition of ATM activity as described above. Typically, such amounts may be determined by one skilled in the art by, for example, starting with the dosage range described in this specification for the compound of formula (I) or pharmaceutically acceptable salt thereof and an approved or otherwise published dosage range(s) of the other pharmaceutically active compound(s).

"Warm-blooded animals" include, for example, humans.

In one embodiment there is provided a method for treating cancer in a warm-blooded animal in need of such treatment, which comprises administering to said warm-blooded animal a therapeutically effective amount of a compound of Formula (I), or a pharmaceutically acceptable salt thereof. In one embodiment, said cancer is selected from the group consisting of colorectal cancer, glioblastoma, gastric cancer, ovarian cancer, diffuse large B-cell lymphoma, chronic lymphocytic leukaemia, acute myeloid leukaemia, head and neck squamous cell carcinoma, breast cancer, hepatocellular carcinoma, small cell lung cancer and non-small cell lung cancer. In one embodiment, said cancer is selected from the group consisting of colorectal cancer, glioblastoma, gastric cancer, ovarian cancer, diffuse large B-cell lymphoma, chronic lymphocytic leukaemia, head and neck squamous cell carcinoma and lung cancer. In one embodiment, said cancer is colorectal cancer.

In any embodiment where cancer is mentioned in a general sense, said cancer may be selected from the group consisting of colorectal cancer, glioblastoma, gastric cancer, ovarian cancer, diffuse large B-cell lymphoma, chronic lymphocytic leukaemia, acute myeloid leukaemia, head and neck squamous cell carcinoma, breast cancer, hepatocellular carcinoma, small cell lung cancer and non-small cell lung cancer. Said cancer may also be selected from the group consisting of colorectal cancer, glioblastoma, gastric cancer, ovarian cancer, diffuse large B-cell lymphoma, chronic lymphocytic leukaemia, head and neck squamous cell carcinoma and lung cancer.

In any embodiment where cancer is mentioned in a general sense the following embodiments may apply:

In one embodiment the cancer is colorectal cancer.

In one embodiment the cancer is glioblastoma.

In one embodiment the cancer is gastric cancer.

In one embodiment the cancer is oesophageal cancer.

In one embodiment the cancer is ovarian cancer.

In one embodiment the cancer is endometrial cancer.

In one embodiment the cancer is cervical cancer.

In one embodiment the cancer is diffuse large B-cell lymphoma.

In one embodiment the cancer is chronic lymphocytic leukaemia.

In one embodiment the cancer is acute myeloid leukaemia.

In one embodiment the cancer is head and neck squamous cell carcinoma.

In one embodiment the cancer is breast cancer. In one embodiment the cancer is triple negative breast cancer.

"Triple negative breast cancer" is any breast cancer that does not express the genes for the oestrogen receptor, progesterone receptor and Her2/neu.

In one embodiment the cancer is hepatocellular carcinoma.

In one embodiment the cancer is lung cancer. In one embodiment the lung cancer is small cell lung cancer. In one embodiment the lung cancer is non-small cell lung cancer.

In one embodiment the cancer is metastatic cancer. In one embodiment the metastatic cancer comprises metastases of the central nervous system. In one embodiment the metastases of the central nervous system comprise brain metastases. In one embodiment the metastases of the central nervous system comprise leptomeningeal metastases.

"Leptomeningeal metastases" occur when cancer spreads to the meninges, the layers of tissue that cover the brain and the spinal cord. Metastases can spread to the meninges through the blood or they can travel from brain metastases, carried by the cerebrospinal fluid (CSF) that flows through the meninges. In one embodiment the cancer is non-metastatic cancer.

The anti-cancer treatment described in this specification may be useful as a sole therapy, or may involve, in addition to administration of the compound of Formula (I), conventional surgery, radiotherapy or chemotherapy; or a combination of such additional therapies. Such conventional surgery, radiotherapy or chemotherapy may be administered simultaneously, sequentially or separately to treatment with the compound of Formula (I).

Radiotherapy may include one or more of the following categories of therapy:
i. External radiation therapy using electromagnetic radiation, and intraoperative radiation therapy using electromagnetic radiation;
ii. Internal radiation therapy or brachytherapy; including interstitial radiation therapy or intraluminal radiation therapy; or
iii. Systemic radiation therapy, including but not limited to iodine 131 and strontium 89.

Therefore, in one embodiment there is provided a compound of Formula (I), or a pharmaceutically acceptable salt thereof, and radiotherapy, for use in the treatment of cancer. In one embodiment the cancer is glioblastoma. In one embodiment, the cancer is metastatic cancer. In one embodiment the metastatic cancer comprises metastases of the central nervous system. In one embodiment the metastases of the central nervous system comprise brain metastases. In one embodiment the metastases of the central nervous system comprise leptomeningeal metastases.

In one embodiment there is provided a compound of Formula (I), or a pharmaceutically acceptable salt thereof, for use in the treatment of cancer, where the compound of Formula (I), or a pharmaceutically acceptable salt thereof, is administered in combination with radiotherapy. In one embodiment the cancer is glioblastoma. In one embodiment, the cancer is metastatic cancer. In one embodiment the metastatic cancer comprises metastases of the central nervous system. In one embodiment the metastases of the central nervous system comprise brain metastases. In one embodiment the metastases of the central nervous system comprise leptomeningeal metastases.

In one embodiment there is provided a compound of Formula (I), or a pharmaceutically acceptable salt thereof, and radiotherapy, for use in the simultaneous, separate or sequential treatment of cancer. In one embodiment the cancer is selected from glioblastoma, lung cancer (for example small cell lung cancer or non-small cell lung cancer), breast cancer (for example triple negative breast cancer), head and neck squamous cell carcinoma, oesophageal cancer, cervical cancer and endometrial cancer. In one embodiment the cancer is glioblastoma. In one embodiment, the cancer is metastatic cancer. In one embodiment the metastatic cancer comprises metastases of the central nervous system. In one embodiment the metastases of the central nervous system comprise brain metastases. In one embodiment the metastases of the central nervous system comprise leptomeningeal metastases.

In one embodiment there is provided a compound of Formula (I), or a pharmaceutically acceptable salt thereof, for use in the treatment of cancer, where the compound of Formula (I), or a pharmaceutically acceptable salt thereof, is administered simultaneously, separately or sequentially with radiotherapy. In one embodiment the cancer is selected from glioblastoma, lung cancer (for example small cell lung cancer or non-small cell lung cancer), breast cancer (for example triple negative breast cancer), head and neck squamous cell carcinoma, oesophageal cancer, cervical cancer and endometrial cancer. In one embodiment the cancer is glioblastoma. In one embodiment, the cancer is metastatic cancer. In one embodiment the metastatic cancer comprises metastases of the central nervous system. In one embodiment the metastases of the central nervous system comprise brain metastases. In one embodiment the metastases of the central nervous system comprise leptomeningeal metastases.

In one embodiment there is provided a method of treating cancer in a warm-blooded animal who is in need of such treatment, which comprises administering to said warm-blooded animal a compound of Formula (I), or a pharmaceutically acceptable salt thereof and radiotherapy, where the compound of Formula (I), or a pharmaceutically acceptable salt thereof, and radiotherapy are jointly effective in producing an anti-cancer effect. In one embodiment the cancer is selected from glioblastoma, lung cancer (for example small cell lung cancer or non-small cell lung cancer), breast cancer (for example triple negative breast cancer), head and neck squamous cell carcinoma, oesophageal cancer, cervical cancer and endometrial cancer. In one embodiment the cancer is glioblastoma. In one embodiment, the cancer is metastatic cancer. In one embodiment the metastatic cancer comprises metastases of the central nervous system. In one embodiment the metastases of the central nervous system comprise brain metastases. In one embodiment the metastases of the central nervous system comprise leptomeningeal metastases.

In one embodiment there is provided a method of treating cancer in a warm-blooded animal who is in need of such treatment, which comprises administering to said warm-blooded animal a compound of Formula (I), or a pharmaceutically acceptable salt thereof and simultaneously, separately or sequentially administering radiotherapy, where the compound of Formula (I), or a pharmaceutically acceptable salt thereof, and radiotherapy are jointly effective in producing an anti-cancer effect. In one embodiment the cancer is glioblastoma. In one embodiment, the cancer is metastatic cancer. In one embodiment the metastatic cancer comprises metastases of the central nervous system. In one embodiment the metastases of the central nervous system comprise brain metastases. In one embodiment the metastases of the central nervous system comprise leptomeningeal metastases.

In any embodiment the radiotherapy is selected from the group consisting of one or more of the categories of radiotherapy listed under points (i)-(iii) above.

Chemotherapy may include one or more of the following categories of anti-tumour substance:
i. Antineoplastic agents and combinations thereof, such as DNA alkylating agents (for example cisplatin, oxaliplatin, carboplatin, cyclophosphamide, nitrogen mustards like ifosfamide, bendamustine, melphalan, chlorambucil, busulphan, temozolamide and nitrosoureas like carmustine); antimetabolites (for example gemcitabine and antifolates such as fluoropyrimidines like 5-fluorouracil and tegafur, raltitrexed, methotrexate, cytosine arabinoside, and hydroxyurea); anti-tumour antibiotics (for example anthracyclines like adriamycin, bleomycin, doxorubicin, liposomal doxorubicin, pirarubicin, daunomycin, valrubicin, epirubicin, idarubicin, mitomycin-C, dactinomycin, amrubicin and mithramycin); antimitotic agents (for example vinca alkaloids like vincristine, vinblastine, vindesine and vinorelbine and taxoids like taxol and taxotere and polokinase inhibitors); and topoisomerase inhibitors (for example epipodophyllotoxins like etoposide and teniposide, amsacrine, irinotecan, topotecan and camptothecin);

inhibitors of DNA repair mechanisms such as CHK kinase; DNA-dependent protein kinase inhibitors; inhibitors of poly (ADP-ribose) polymerase (PARP inhibitors, including olaparib); and Hsp90 inhibitors such as tanespimycin and retaspimycin, inhibitors of ATR kinase (such as AZD6738); and inhibitors of WEE1 kinase (such as AZD1775/MK-1775);

ii. Antiangiogenic agents such as those that inhibit the effects of vascular endothelial growth factor, for example the anti-vascular endothelial cell growth factor antibody bevacizumab and for example, a VEGF receptor tyrosine kinase inhibitor such as vandetanib (ZD6474), sorafenib, vatalanib (PTK787), sunitinib (SU11248), axitinib (AG-013736), pazopanib (GW 786034) and cediranib (AZD2171); compounds such as those disclosed in International Patent Applications WO97/22596, WO 97/30035, WO 97/32856 and WO 98/13354; and compounds that work by other mechanisms (for example linomide, inhibitors of integrin αvβ3 function and angiostatin), or inhibitors of angiopoietins and their receptors (Tie-1 and Tie-2), inhibitors of PLGF, inhibitors of delta-like ligand (DLL-4);

iii. Immunotherapy approaches, including for example ex-vivo and in-vivo approaches to increase the immunogenicity of patient tumour cells, such as transfection with cytokines such as interleukin 2, interleukin 4 or granulocyte-macrophage colony stimulating factor; approaches to decrease T-cell anergy or regulatory T-cell function; approaches that enhance T-cell responses to tumours, such as blocking antibodies to CTLA4 (for example ipilimumab and tremelimumab), B7H1, PD-1 (for example BMS-936558 or AMP-514), PD-L 1 (for example MEDI4736) and agonist antibodies to CD137; approaches using transfected immune cells such as cytokine-transfected dendritic cells; approaches using cytokine-transfected tumour cell lines, approaches using antibodies to tumour associated antigens, and antibodies that deplete target cell types (e.g., unconjugated anti-CD20 antibodies such as Rituximab, radiolabeled anti-CD20 antibodies Bexxar and Zevalin, and anti-CD54 antibody Campath); approaches using anti-idiotypic antibodies; approaches that enhance Natural Killer cell function; and approaches that utilize antibody-toxin conjugates (e.g. anti-CD33 antibody Mylotarg); immunotoxins such as moxetumumab pasudotox; agonists of toll-like receptor 7 or toll-like receptor 9;

iv. Efficacy enhancers, such as leucovorin.

Therefore, in one embodiment there is provided a compound of Formula (I), or a pharmaceutically acceptable salt thereof, and at least one additional anti-tumour substance, for use in the treatment of cancer. In one embodiment there is provided a compound of Formula (I), or a pharmaceutically acceptable salt thereof, for use in the treatment of cancer, where the compound of Formula (I), or a pharmaceutically acceptable salt thereof is administered in combination with an additional anti-tumour substance. In one embodiment there is one additional anti-tumour substance. In one embodiment there are two additional anti-tumour substances. In one embodiment there are three or more additional anti-tumour substances.

In one embodiment there is provided a compound of Formula (I), or a pharmaceutically acceptable salt thereof, and at least one additional anti-tumour substance for use in the simultaneous, separate or sequential treatment of cancer. In one embodiment there is provided a compound of Formula (I), or a pharmaceutically acceptable salt thereof, for use in the treatment of cancer, where the compound of Formula (I), or a pharmaceutically acceptable salt thereof, is administered simultaneously, separately or sequentially with an additional anti-tumour substance.

In one embodiment there is provided a method of treating cancer in a warm-blooded animal who is in need of such treatment, which comprises administering to said warm-blooded animal a compound of Formula (I), or a pharmaceutically acceptable salt thereof and at least one additional anti-tumour substance, where the amounts of the compound of Formula (I), or a pharmaceutically acceptable salt thereof, and the additional anti-tumour substance are jointly effective in producing an anti-cancer effect.

In one embodiment there is provided a method of treating cancer in a warm-blooded animal who is in need of such treatment, which comprises administering to said warm-blooded animal a compound of Formula (I), or a pharmaceutically acceptable salt thereof, and simultaneously, separately or sequentially administering at least one additional anti-tumour substance to said warm-blooded animal, where the amounts of the compound of Formula (I), or pharmaceutically acceptable salt thereof, and the additional anti-tumour substance are jointly effective in producing an anti-cancer effect.

In any embodiment the additional anti-tumour substance is selected from the group consisting of one or more of the anti-tumour substances listed under points (i)-(iv) above.

In one embodiment there is provided a compound of Formula (I), or a pharmaceutically acceptable salt thereof, and at least one anti-neoplastic agent for use in the treatment of cancer. In one embodiment there is provided a compound of Formula (I), or a pharmaceutically acceptable salt thereof, for use in the treatment of cancer, where the compound of Formula (I), or a pharmaceutically acceptable salt thereof, is administered in combination with at least one anti-neoplastic agent. In one embodiment the anti-neoplastic agent is selected from the list of antineoplastic agents in point (i) above.

In one embodiment there is provided a compound of Formula (I), or a pharmaceutically acceptable salt thereof, and at least one anti-neoplastic agent for use in the simultaneous, separate or sequential treatment of cancer. In one embodiment there is provided a compound of Formula (I), or a pharmaceutically acceptable salt thereof, for use in the treatment of cancer, where the compound of Formula (I), or a pharmaceutically acceptable salt thereof, is administered simultaneously, separately or sequentially with at least one anti-neoplastic agent. In one embodiment the antineoplastic agent is selected from the list of antineoplastic agents in point (i) above.

In one embodiment there is provided a compound of Formula (I), or a pharmaceutically acceptable salt thereof, and at least one additional anti-tumour substance selected from the group consisting of cisplatin, oxaliplatin, carboplatin, valrubicin, idarubicin, doxorubicin, pirarubicin, irinotecan, topotecan, amrubicin, epirubicin, etoposide, mitomycin, bendamustine, chlorambucil, cyclophosphamide, ifosfamide, carmustine, melphalan, bleomycin, olaparib, MEDI4736, AZD1775 and AZD6738, for use in the treatment of cancer.

In one embodiment there is provided a compound of Formula (I), or a pharmaceutically acceptable salt thereof, and at least one additional anti-tumour substance selected from the group consisting of cisplatin, oxaliplatin, carboplatin, doxorubicin, pirarubicin, irinotecan, topotecan, amrubicin, epirubicin, etoposide, mitomycin, bendamustine, chlorambucil, cyclophosphamide, ifosfamide, carmustine, melphalan, bleomycin, olaparib, AZD1775 and AZD6738, for use in the treatment of cancer.

In one embodiment there is provided a compound of Formula (I), or a pharmaceutically acceptable salt thereof, for use in the treatment of cancer, where the compound of Formula (I), or a pharmaceutically acceptable salt thereof, is administered in combination with at least one additional anti-tumour substance selected from the group consisting of cisplatin, oxaliplatin, carboplatin, valrubicin, idarubicin, doxorubicin, pirarubicin, irinotecan, topotecan, amrubicin, epirubicin, etoposide, mitomycin, bendamustine, chlorambucil, cyclophosphamide, ifosfamide, carmustine, melphalan, bleomycin, olaparib, MEDI4736, AZD1775 and AZD6738.

In one embodiment there is provided a compound of Formula (I), or a pharmaceutically acceptable salt thereof, and at least one additional anti-tumour substance selected from the group consisting of doxorubicin, irinotecan, topotecan, etoposide, mitomycin, bendamustine, chlorambucil, cyclophosphamide, ifosfamide, carmustine, melphalan, bleomycin and olaparib for use in the treatment of cancer.

In one embodiment there is provided a compound of Formula (I), or a pharmaceutically acceptable salt thereof, for use in the treatment of cancer, where the compound of Formula (I), or a pharmaceutically acceptable salt thereof, is administered in combination with at least one additional anti-tumour substance selected from the group consisting of doxorubicin, irinotecan, topotecan, etoposide, mitomycin, bendamustine, chlorambucil, cyclophosphamide, ifosfamide, carmustine, melphalan, bleomycin and olaparib.

In one embodiment there is provided a compound of Formula (I), or a pharmaceutically acceptable salt thereof, and at least one additional anti-tumour substance selected from the group consisting of doxorubicin, irinotecan, topotecan, etoposide, mitomycin, bendamustine, chlorambucil, cyclophosphamide, ifosfamide, carmustine, melphalan and bleomycin, for use in the treatment of cancer.

In one embodiment there is provided a compound of Formula (I), or a pharmaceutically acceptable salt thereof, for use in the treatment of cancer, where the compound of Formula (I), or a pharmaceutically acceptable salt thereof, is administered in combination with at least one additional anti-tumour substance selected from the group consisting of doxorubicin, irinotecan, topotecan, etoposide, mitomycin, bendamustine, chlorambucil, cyclophosphamide, ifosfamide, carmustine, melphalan and bleomycin.

In one embodiment there is provided a compound of Formula (I), or a pharmaceutically acceptable salt thereof, for use in the treatment of cancer, where the compound of Formula (I), or a pharmaceutically acceptable salt thereof, is administered in combination with at least one additional anti-tumour substance selected from the group consisting of doxorubicin, pirarubicin, amrubicin and epirubicin. In one embodiment the cancer is acute myeloid leukaemia. In one embodiment the cancer is breast cancer (for example triple negative breast cancer). In one embodiment the cancer is hepatocellular carcinoma.

In one embodiment there is provided a compound of Formula (I), or a pharmaceutically acceptable salt thereof, and irinotecan, for use in the treatment of cancer. In one embodiment there is provided a compound of Formula (I), or a pharmaceutically acceptable salt thereof, for use in the treatment of cancer, where the compound of Formula (I), or a pharmaceutically acceptable salt thereof, is administered in combination with irinotecan. In one embodiment the cancer is colorectal cancer.

In one embodiment there is provided a compound of Formula (I), or a pharmaceutically acceptable salt thereof, and FOLFIRI, for use in the treatment of cancer. In one embodiment there is provided a compound of Formula (I), or a pharmaceutically acceptable salt thereof, for use in the treatment of cancer, where the compound of Formula (I), or a pharmaceutically acceptable salt thereof, is administered in combination with FOLFIRI. In one embodiment the cancer is colorectal cancer.

FOLFIRI is a dosage regime involving a combination of leucovorin, 5-fluorouracil and irinotecan.

In one embodiment there is provided a compound of Formula (I), or a pharmaceutically acceptable salt thereof, for use in the treatment of cancer, where the compound of Formula (I), or a pharmaceutically acceptable salt thereof, is administered in combination with olaparib. In one embodiment the cancer is gastric cancer.

In one embodiment there is provided a compound of Formula (I), or a pharmaceutically acceptable salt thereof, for use in the treatment of cancer, where the compound of Formula (I), or a pharmaceutically acceptable salt thereof, is administered in combination with topotecan. In one embodiment the cancer is small cell lung cancer. In one embodiment there is provided a compound of Formula (I), or a pharmaceutically acceptable salt thereof, for use in the treatment of cancer, where the compound of Formula (I), or a pharmaceutically acceptable salt thereof, is administered in combination with immunotherapy. In one embodiment the immunotherapy is one or more of the agents listed under point (iii) above. In one embodiment the immunotherapy is an anti-PD-L1 antibody (for example MEDI4736).

According to a further embodiment there is provided a kit comprising:
a) A compound of formula (I), or a pharmaceutically acceptable salt thereof, in a first unit dosage form;
b) A further additional anti-tumour substance in a further unit dosage form; c) Container means for containing said first and further unit dosage forms; and optionally
d) Instructions for use. In one embodiment the anti-tumour substance comprises an anti-neoplastic agent.

In any embodiment where an anti-neoplastic agent is mentioned, the anti-neoplastic agent is one or more of the agents listed under point (i) above.

The compounds of Formula (I), and pharmaceutically acceptable salts thereof, may be administered as pharmaceutical compositions, comprising one or more pharmaceutically acceptable excipients.

Therefore, in one embodiment there is provided a pharmaceutical composition comprising a compound of Formula (I), or a pharmaceutically acceptable salt thereof, and at least one pharmaceutically acceptable excipient.

The excipient(s) selected for inclusion in a particular composition will depend on factors such as the mode of administration and the form of the composition provided. Suitable pharmaceutically acceptable excipients are well known to persons skilled in the art and are described, for example, in the *Handbook of Pharmaceutical Excipients*, Sixth edition, Pharmaceutical Press, edited by Rowe, Ray C; Sheskey, Paul J; Quinn, Marian. Pharmaceutically acceptable excipients may function as, for example, adjuvants, diluents, carriers, stabilisers, flavourings, colorants, fillers, binders, disintegrants, lubricants, glidants, thickening agents and coating agents. As persons skilled in the art will appreciate, certain pharmaceutically acceptable excipients may serve more than one function and may serve alternative functions depending on how much of the excipient is present in the composition and what other excipients are present in the composition.

The pharmaceutical compositions may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing), or as a suppository for rectal dosing. The compositions may be obtained by conventional procedures well known in the art. Compositions intended for oral use may contain additional components, for example, one or more colouring, sweetening, flavouring and/or preservative agents.

The compound of Formula (I) will normally be administered to a warm-blooded animal at a unit dose within the range 2.5-5000 mg/m$^2$ body area of the animal, or approximately 0.05-100 mg/kg, and this normally provides a therapeutically-effective dose. A unit dose form such as a tablet or capsule will usually contain, for example 0.1-250 mg of active ingredient. The daily dose will necessarily be varied depending upon the host treated, the particular route of administration, any therapies being co-administered, and the severity of the illness being treated. Accordingly the practitioner who is treating any particular patient may determine the optimum dosage.

The pharmaceutical compositions described herein comprise compounds of Formula (I), or a pharmaceutically acceptable salt thereof, and are therefore expected to be useful in therapy.

As such, in one embodiment there is provided a pharmaceutical composition for use in therapy, comprising a compound of Formula (I), or a pharmaceutically acceptable salt thereof, and at least one pharmaceutically acceptable excipient.

In one embodiment there is provided a pharmaceutical composition for use in the treatment of a disease in which inhibition of ATM kinase is beneficial, comprising a compound of Formula (I), or a pharmaceutically acceptable salt thereof, and at least one pharmaceutically acceptable excipient.

In one embodiment there is provided a pharmaceutical composition for use in the treatment of cancer, comprising a compound of Formula (I), or a pharmaceutically acceptable salt thereof, and at least one pharmaceutically acceptable excipient.

In one embodiment there is provided a pharmaceutical composition for use in the treatment of a cancer in which inhibition of ATM kinase is beneficial, comprising a compound of Formula (I), or a pharmaceutically acceptable salt thereof, and at least one pharmaceutically acceptable excipient.

In one embodiment there is provided a pharmaceutical composition for use in the treatment of colorectal cancer, glioblastoma, gastric cancer, ovarian cancer, diffuse large B-cell lymphoma, chronic lymphocytic leukaemia, acute myeloid leukaemia, head and neck squamous cell carcinoma, breast cancer, hepatocellular carcinoma, small cell lung cancer or non-small cell lung cancer, comprising a compound of Formula (I), or a pharmaceutically acceptable salt thereof, and at least one pharmaceutically acceptable excipient.

EXAMPLES

The various embodiments of the invention are illustrated by the following Examples. The invention is not to be interpreted as being limited to the Examples. During the preparation of the Examples, generally:

i. Operations were carried out at ambient temperature, i.e. in the range of about 17 to 30° C. and under an atmosphere of an inert gas such as nitrogen unless otherwise stated;

ii. Evaporations were carried out by rotary evaporation or utilising Genevac equipment in vacuo and work-up procedures were carried out after removal of residual solids by filtration;

iii. Flash chromatography purifications were performed on an automated Armen Glider Flash: Spot II Ultimate (Armen Instrument, Saint-Ave, France) or automated Presearch combiflash companions using prepacked Merck normal phase Si60 silica cartridges (granulometry: 15-40 or 40-63 μm) obtained from Merck, Darmstad, Germany, silicycle silica cartridges or graceresolv silica cartridges;

iv. Preparative chromatography was performed on a Waters instrument (600/2700 or 2525) fitted with a ZMD or ZQ ESCi mass spectrometers and a Waters X-Terra or a Waters X-Bridge or a Waters SunFire reverse-phase column (C-18, 5 microns silica, 19 mm or 50 mm diameter, 100 mm length, flow rate of 40 mL/minute) using decreasingly polar mixtures of water (containing 1% ammonia) and acetonitrile or decreasingly polar mixtures of water (containing 0.1% formic acid) and acetonitrile as eluents;

v. Yields, where present, are not necessarily the maximum attainable;

vi. Structures of end-products of Formula (I) were confirmed by nuclear magnetic resonance (NMR) spectroscopy, with NMR chemical shift values measured on the delta scale. Proton magnetic resonance spectra were determined using a Bruker advance 700 (700 MHz), Bruker Avance 500 (500 MHz), Bruker 400 (400 MHz) or Bruker 300 (300 MHz) instrument; 19F NMR were determined at 282 MHz or 376 MHz; 13C NMR were determined at 75 MHz or 100 MHz; measurements were taken at around 20-30° C. unless otherwise specified; the following abbreviations have been used: s, singlet; d, doublet; t, triplet; q, quartet; m, multiplet; dd, doublet of doublets; ddd, doublet of doublet of doublet; dt, doublet of triplets; bs, broad signal;

vii. End-products of Formula (I) were also characterised by mass spectroscopy following liquid chromatography (LCMS); LCMS was carried out using an Waters Alliance HT (2790 & 2795) fitted with a Waters ZQ ESCi or ZMD ESCi mass spectrometer and an X Bridge 5 μm C-18 column (2.1×50 mm) at a flow rate of 2.4 mL/min, using a solvent system of 95% A+5% C to 95% B+5% C over 4 minutes, where A=water, B=methanol, C=1:1 methanol:water (containing 0.2% ammonium carbonate); or by using a Shimadzu UFLC or UHPLC coupled with DAD detector, ELSD detector and 2020 EV mass spectrometer (or equivalent) fitted with a Phenomenex Gemini-NX C18 3.0×50 mm, 3.0 μM column or equivalent (basic conditions) or a Shim pack XR—ODS 3.0×50 mm, 2.2 μM column or Waters BEH C18 2.1×50 mm, 1.7 μM column or equivalent using a solvent system of 95% D+5% E to 95% E+5% D over 4 minutes, where D=water (containing 0.05% TFA), E=Acetonitrile (containing 0.05% TFA) (acidic conditions) or a solvent system of 90% F+10% G to 95% G+5% F over 4 minutes, where F=water (containing 6.5 mM ammonium hydrogen carbonate and adjusted to pH10 by addition of ammonia), G=Acetonitrile (basic conditions);

viii. Intermediates were not generally fully characterised and purity was assessed by thin layer chromatographic, mass spectral, HPLC and/or NMR analysis;

ix. X-ray powder diffraction spectra were determined (using a Bruker D4 Analytical Instrument) by mounting a sample of the crystalline material on a Bruker single silicon crystal (SSC) wafer mount and spreading out the sample into a thin layer with the aid of a microscope slide. The sample was spun at 30 revolutions per minute (to improve counting statistics) and irradiated with X-rays generated by a copper long-fine focus tube operated at 40 kV and 40 mA with a wavelength of 1.5418 angstroms. The collimated X-ray source was passed through an automatic variable divergence slit set at V20 and the reflected radiation directed through a 5.89 mm antiscatter slit and a 9.55 mm detector slit. The sample was exposed for 0.03 seconds per 0.00570° 2-theta increment (continuous scan mode) over the range 2 degrees to 40 degrees 2-theta in theta-theta mode. The running time was 3 minutes and 36 seconds. The instrument was equipped with a Position sensitive detector (Lynxeye). Control and data capture was by means of a Dell Optiplex 686 NT 4.0 Workstation operating with Diffrac+ software;

x. Differential Scanning Calorimetry was performed on a TA Instruments Q1000 DSC. Typically, less than 5 mg of material contained in a standard aluminium pan fitted with a lid was heated over the temperature range 25° C. to 300° C. at a constant heating rate of 10° C. per minute. A purge gas using nitrogen was used at a flow rate 50 ml per minute xi. The following abbreviations have been used: h=hour(s); r.t.=room temperature (~18-25° C.); conc.=concentrated; FCC=flash column chromatography using silica; DCM=dichloromethane; DIPEA=diisopropylethylamine; DMA=N,N-dimethylacetamide; DMF=N,N-dimethylformamide; DMSO=dimethylsulfoxide; Et$_2$O=diethyl ether; EtOAc=ethyl acetate; EtOH=ethanol; K$_2$CO$_3$=potassium carbonate; MeOH=methanol; MeCN=acetonitrile; MTBE=Methyltertbutylether; MgSO$_4$=anhydrous magnesium sulphate; Na$_2$SO$_4$=anhydrous sodium sulphate; THF=tetrahydrofuran; sat.=saturated aqueous solution; and xii. IUPAC names were generated using either "Canvas" or 'IBIS', AstraZeneca proprietary programs. As stated in the introduction, the compounds of the invention comprise an imidazo[4,5-c]quinolin-2-one core. However, in certain Examples the IUPAC name describes the core as an imidazo[5,4-c]quinolin-2-one. The imidazo[4,5-c]quinolin-2-one and imidazo[5,4-c]quinolin-2-one cores are nevertheless the same, with the naming convention different because of the peripheral groups.

Example 1

8-[6-[3-(Dimethylamino)propoxy]-3-pyidyl]-7-fluoro-1-isopropyl-3-methyl-imidazo[4,5-c]quinolin-2-one

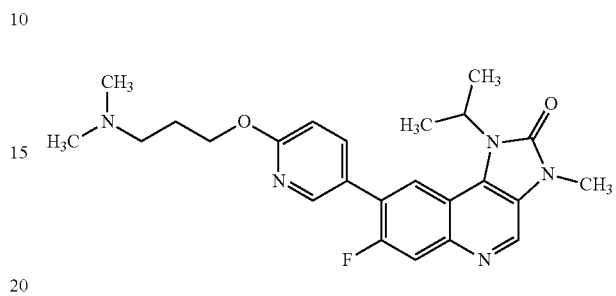

3-(Dimethylamino)propan-1-ol (0.433 mL, 3.66 mmol) was added slowly to a slurry of sodium hydride (0.333 g, 8.33 mmol) in THF (10 mL) and the solution stirred at 0° C. for 30 minutes. The solution was added to a solution of 7-fluoro-8-(6-fluoro-3-pyridyl)-1-isopropyl-3-methyl-imidazo[4,5-c]quinolin-2-one (1.18 g, 3.33 mmol) in THF (20 mL). The reaction was stirred at r.t. for 24 h and quenched with water. The solvent was removed under reduced pressure and extracted with DCM (2×100 mL). The organics were washed with water (50 mL), dried over a phase separator and the solvent removed under reduced pressure to afford crude product. The crude product was purified by flash silica chromatography, elution gradient 0 to 10% MeOH in DCM, to afford the desired material. The solid was heated in MeCN (15 mL) and allowed to cool to r.t. overnight. The white solid was filtered under vacuum and dried in a vacuum oven for 3 h to afford the desired material as a white solid (1.79 g, 41%). NMR Spectrum: $^1$H NMR (500 MHz, DMSO-d6) δ 1.65 (6H, d), 1.90 (2H, p), 2.17 (6H, s), 2.38 (2H, t), 3.50 (3H, s), 4.38 (2H, t), 5.29 (H, hept), 6.99 (1H, dd), 7.92 (1H, d), 8.05 (1H, dt), 8.33 (1H, d), 8.50 (1H, dd), 8.91 (1H, s). $^1$H NMR (500 MHz, CDCl$_3$) δ 1.76 (6H, d), 1.96-2.06 (2H, m), 2.28 (6H, s), 2.44-2.51 (2H, m), 3.58 (3H, s), 4.44 (2H, t), 5.22 (1H, s), 6.89 (1H, dd), 7.86-7.92 (2H, m), 8.21 (1H, d), 8.41 (1H, d), 8.69 (1H, s). Mass Spectrum: m/z (ES+)[M+H]+=438.

The desired material can also be isolated as the methane sulfonic acid salt as described below: 1M Methanesulfonic acid in DCM (0.660 mL, 0.66 mmol) was added portionwise to isolated free base (275 mg, 0.63 mmol) in DCM (5 mL) at ambient temperature over a period of 1 minute. The resulting solution was stirred at ambient temperature for 1 h then concentrated in vacuo and the residue dried under vacuum to afford the desired methanesulfonic acid salt as a white solid (336 mg, 100%). NMR Spectrum: $^1$H NMR (500 MHz, DMSO-d6) δ 1.65 (6H, d), 2.05-2.21 (2H, m), 2.32 (3H, s), 2.76 (6H, s), 3.04-3.21 (2H, m), 3.51 (3H, s), 4.43 (2H, t), 5.29 (1H, hept), 7.02 (1H, dd), 7.93 (1H, d), 8.09 (1H, dt), 8.32 (1H, d), 8.53 (1H, dd), 8.92 (1H, s), 9.36 (1H, s). Mass Spectrum: m/z (ES+)[M+H]+=438.

Intermediate A1: 7-Fluoro-8-(6-fluoro-3-pyridyl)-1-isopropyl-3-methyl-imidazo[4,5-c]quinolin-2-one

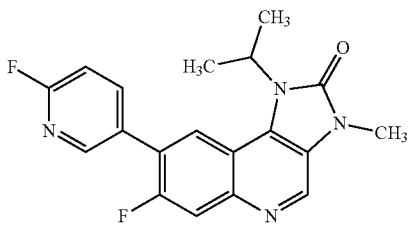 [SMILES: CC(C)n1c(=O)n(C)c2cnc3cc(F)c(-c4ccc(F)nc4)cc3c21]

Dichlorobis(di-tert-butyl(3-sulfopropyl)phosphonio)palladate(II) (0.05M solution in water, 11.83 mL, 0.59 mmol) was added to a degassed mixture of 8-bromo-7-fluoro-1-isopropyl-3-methyl-imidazo[4,5-c]quinolin-2-one (4.0 g, 11.83 mmol), (6-fluoropyridin-3-yl)boronic acid (2.0 g, 14.19 mmol) and 2M potassium carbonate solution (17.74 mL, 35.48 mmol) in 1,4-dioxane (50 mL) and water (12.5 mL). The mixture was purged with nitrogen and heated to 80° C. for 1 h then allowed to cool and concentrated under reduced pressure to remove. The remaining solution was diluted with DCM (250 mL), washed with water (200 mL) and the organic layer dried with a phase separating cartridge and evaporated to afford crude product. The crude product was purified by flash silica chromatography, elution gradient 0 to 10% MeOH in DCM, to afford the desired material as a white solid (3.70 g, 88%). NMR Spectrum: $^1$H NMR (500 MHz, CDCl$_3$) δ 1.77 (6H, dd), 3.58 (3H, d), 5.20 (1H, s), 7.11 (1H, ddd), 7.93 (1H, d), 8.06-8.14 (1H, m), 8.22 (1H, d), 8.46-8.51 (1H, m), 8.72 (1H, s). Mass Spectrum: m/z (ES+)[M+H]+=355.3.

Dichlorobis(di-tert-butyl(3-sulfopropyl)phosphonio)palladate(II) (0.05M solution in water) can be prepared as described below:

Degassed water (30 mL) was added to sodium tetrachloropalladate(II) (0.410 g, 1.39 mmol) and 3-(di-tert-butylphosphino)propane-1-sulfonic acid (0.748 g, 2.79 mmol) at ambient temperature under an inert atmosphere. The suspension was stirred for 5 minutes, then the solid removed by filtration and discarded to leave the desired reagent as a red-brown solution.

Intermediate A2: 8-Bromo-7-fluoro-1-isopropyl-3-methyl-imidazo[4,5-c]quinolin-2-one

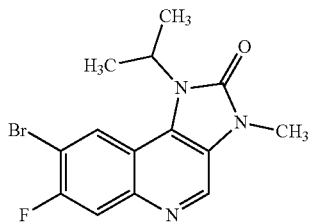 [SMILES: CC(C)n1c(=O)n(C)c2cnc3cc(F)c(Br)cc3c21]

A solution of sodium hydroxide (11.29 g, 282.28 mmol) in water (600 mL) was added to a stirred mixture of 8-bromo-7-fluoro-1-isopropyl-3H-imidazo[4,5-c]quinolin-2-one (61 g, 188.19 mmol), tetrabutylammonium bromide (6.07 g, 18.82 mmol) and methyl iodide (23.53 mL, 376.37 mmol) in DCM (1300 mL) and the mixture stirred at ambient temperature for 17 h. The same process was repeated on an identical scale and the reaction mixtures combined, concentrated and diluted with MeOH (750 mL). The precipitate was collected by filtration, washed with MeOH (500 mL) and the solid dried under vacuum to afford the desired material as a white solid (108 g, 85%). NMR Spectrum: $^1$H NMR (400 MHz, CDCl$_3$) δ 1.76 (6H, d), 3.57 (3H, s), 5.13 (1H, t), 7.83 (1H, d), 8.41 (1H, d), 8.69 (1H, s). Mass Spectrum: m/z (ES+)[M+H]+=380.

Intermediate A3: 8-Bromo-7-fluoro-1-isopropyl-3H-imidazo[4,5-c]quinolin-2-one

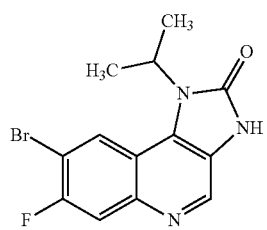 [SMILES: CC(C)n1c(=O)[nH]c2cnc3cc(F)c(Br)cc3c21]

Triethylamine (164 mL, 1173.78 mmol) was added in one portion to 6-bromo-7-fluoro-4-(isopropylamino)quinoline-3-carboxylic acid (128 g, 391.26 mmol) in DMF (1500 mL) and the mixture stirred at ambient temperature under an inert atmosphere for 30 minutes. Diphenylphosphoryl azide (101 mL, 469.51 mmol) was added and the solution stirred for a further 30 minutes at ambient temperature then 3 h at 60° C. The reaction mixture was poured into ice water, the precipitate collected by filtration, washed with water (1 L) and dried under vacuum to afford the desired material as a yellow solid (122 g, 96%). NMR Spectrum: $^1$H NMR (400 MHz, DMSO-d6) δ 1.62 (6H, d), 5.12-5.19 (1H, m), 7.92 (1H, d), 8.57 (1H, d), 8.68 (1H, s), 11.58 (1H, s). Mass Spectrum: m/z (ES+)[M+H]+=324.

8-Bromo-7-fluoro-1-isopropyl-3H-imidazo[4,5-c]quinolin-2-one can also be prepared as described below.

1,3,5-Trichloro-1,3,5-triazinane-2,4,6-trione (5.91 g, 25.45 mmol) was added portionwise to a stirred suspension of 6-bromo-7-fluoro-4-(isopropylamino)quinoline-3-carboxamide (16.6 g, 50.89 mmol) and 1,8-diazabicyclo[5.4.0]undec-7-ene (15.22 mL, 101.79 mmol) in methanol (200 mL) at 5° C. The resulting suspension was stirred at ambient temperature for 1 h. The reaction was filtered and the solid dried in a vacuum oven for 2 h to afford the desired material as a pale yellow solid (14.18 g, 86%). Additional material was obtained after leaving the filtrate to stand for 2 days and then filtering. The additional solid isolated was heated in EtOH (50 mL) for 30 minutes then allowed to cool and filtered to provide additional desired material as a white solid (2.6 mg). Analytical data was consistent with that obtained from alternative preparations described earlier.

A large scale preparation of 8-bromo-7-fluoro-1-isopropyl-3H-imidazo[4,5-c]quinolin-2-one was also carried out as follows. 6-Bromo-7-fluoro-4-(isopropylamino)quinoline-3-carboxylic acid (3.910 kg, 11.15 mol, 93.3 mass %) was charged to a vessel under nitrogen, followed by DMF (22 L). The resulting slurry was stirred and triethylamine (4.7 L) added over 2 min. The resulting mixture was stirred at 21-23° C., then warmed to 56° C. Diphenyl phosphoryl azide (2.9 L, 13 mol, 99.5 mass %) was added over 1 h, keeping the temperature of the mixture in the range 56-61° C. by varying the rate of addition and the jacket set point (exothermic addition—jacket set point 50-57° C.). The addition vessel was rinsed through into the reactor with DMF (0.75 L) and the reaction mixture stirred at 55° C. for 1 h, then analysed by HPLC which indicated completion of the reaction to give the intermediate compound 8-bromo-7-fluoro-1-isopropyl-3H-imidazo[4,5-c]quinolin-2-one. N,N-Dimethylformamide dimethyl acetal (7.29 L, 54.4 mol, 99.2 mass %) was then added over 5 min, and the mixture warmed to 100° C.—precipitation was observed when the temperature reached 94° C. and the stirring rate was increased from 150 to 300 r.p.m. The mixture was stirred for 24 h at 100° C. and analysed by HPLC which indicated 1.2% area of the intermediate (target <0.5% area of intermediate) heating was continued at 99° C. for a further 16 h after which time the reaction was adjudged to have reached a satisfactory level of completion (0.45% area of intermediate remaining). The mixture was then cooled to 22° C. and water (23 L) added over 25 min. keeping the temperature below 30° C. (jacket set initially to 0-5° C. for the first part of the addition which is exothermic—vessel contents kept in the range 22-26° C. throughout the addition). The resulting slurry was stirred at 25-26° C. for 50 min. then filtered and washed with twice with water (11.2 and 11.5 L) that was added to the filter cake via the reaction vessel. The collected solid was sucked dry on the filter for 1 h then transferred to a vacuum oven and dried in vacuo at 60° C. for approx. 26 h to give the desired product (3.445 kg, 9.41 mol, 92.4 mass %, 84.4% Yield).

Intermediate A4: 6-Bromo-7-fluoro-4-(isopropylamino)quinoline-3-carboxylic acid

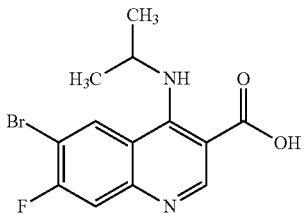 [SMILES: CC(C)Nc1c(C(=O)O)cnc2cc(F)c(Br)cc12]

2N Sodium hydroxide solution (833 mL, 1666.66 mmol) was added portionwise to ethyl 6-bromo-7-fluoro-4-(isopropylamino)quinoline-3-carboxylate (148 g, 416.66 mmol) in THF (1500 mL) at 15° C. and the resulting mixture stirred at 60° C. for 5 h. The reaction mixture was concentrated, diluted with water (2 L) and the mixture acidified with 2M hydrochloric acid. The precipitate was collected by filtration, washed with water (1 L) and dried under vacuum to afford the desired material as a white solid (128 g, 94%). MR Spectrum: $^1$H NMR (400 MHz, DMSO-d6) δ 1.24-1.36 (6H, m), 4.37 (1H, s), 7.78 (1H, t), 8.55 (1H, s), 8.90 (1H, s). Mass Spectrum: m/z (ES+)[M+H]+=327.

6-Bromo-7-fluoro-4-(isopropylamino)quinoline-3-carboxylic acid was also prepared on a larger scale according to the following procedure. A stirred suspension of ethyl 6-bromo-4-chloro-7-fluoroquinoline-3-carboxylate (4 kg, 12.00 mol, 99.8 mass %) in THF (24 L) was heated to 52° C. under an atmosphere of nitrogen. Isopropyl amine (2.10 L, 25.60 mol, 99.9 mass %) was then added over 1 h 30 min. The temperature rose to 54° C. after approximately half of the isopropyl amine was added, the addition was paused, cooling applied, and addition resumed when the temperature had fallen to 48° C. The addition vessel was rinsed with THF (4 L) and the rinse added to the reaction mixture. The mixture was stirred for 18.5 h at 50° C. and then analysed by HPLC which indicated approx. 4% of the starting chloroester remaining (target <0.5%). Further isopropyl amine (150 mL, 1.830 mol, 99.9 mass %) was added and mixture stirrer for a further 22.5 h by which time the reaction was adjudged to have gone to completion. Sodium hydroxide solution (1.99M in water; 13.3 L, 26.50 mol) was charged to the mixture over 5 min. to give a pale yellow mixture that was heated to 60° C. and stirred at this temperature for 22.5 h, then analysed by HPLC that indicated satisfactory completion of the ester hydrolysis. The mixture was cooled to 18° C. then discharged from the vessel to a receiver vessel and recharged back to the reaction vessel via an inline filter. THF (12 L) was charged to the receiver and transferred to the reactor via the inline filter. The vessel jacket temperature was set to 15° C. and Phosphoric acid (1.250 L, 85 mass %) added over 1 h; the temperature of the mixture was 17-18° C. during the addition, resulting in precipitation of the crude product. The resulting slurry was stirred for 20 h at 20° C., then filtered and washed with water (2×20 L) that was added to the filter cake via the reaction vessel. The collected solid was sucked dry on the filter then transferred to a vacuum oven and dried in vacuo at 60° C. for approx. 52 h to give the desired product (3.935 Kg, 11.22 mol, 93.3 mass %, 93.5% Yield).

Intermediate A5: Ethyl 6-bromo-7-fluoro-4-(isopropylamino)quinoline-3-carboxylate

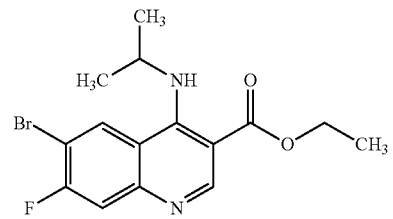 [SMILES: CCOC(=O)c1cnc2cc(F)c(Br)cc2c1NC(C)C]

DIPEA (154 mL, 884.07 mmol) was added portionwise to propan-2-amine (39.2 g, 663.05 mmol) and ethyl 6-bromo-4-chloro-7-fluoroquinoline-3-carboxylate (147 g, 442.04 mmol) in DMA (600 mL) at ambient temperature and the resulting mixture stirred at 100° C. for 4 h. The reaction mixture was poured into ice water, the precipitate collected by filtration, washed with water (1 L) and dried under vacuum to afford the desired material as a light brown solid (148 g, 94%). NMR Spectrum: $^1$H NMR (400 MHz, DMSO-d6) δ 1.26-1.33 (9H, m), 4.17-4.25 (1H, m), 4.32-4.37 (2H, m), 7.28 (1H, d), 8.50 (1H, d), 8.59 (1H, d), 8.86 (1H, s). Mass Spectrum: m/z (ES+)[M+H]+=355.

Intermediate A6: Ethyl 6-bromo-4-chloro-7-fluoroquinoline-3-carboxylate

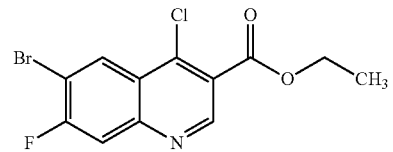 [SMILES: CCOC(=O)c1cnc2cc(F)c(Br)cc2c1Cl]

DMF (0.535 mL, 6.91 mmol) was added to ethyl 6-bromo-7-fluoro-1-[(4-methoxyphenyl)methyl]-4-oxo-quinoline-3-carboxylate (200 g, 460.56 mmol) in thionyl chloride (600 mL) at 10° C. under an inert atmosphere and the resulting mixture stirred at 70° C. for 3 h. The mixture was evaporated to dryness and the residue azeotroped with toluene (300 mL) to afford crude product. The crude product was purified by crystallisation from hexane to afford the desired material as a white solid (147 g, 96%). NMR Spectrum: $^1$H NMR (400 MHz, CDCl$_3$) δ 1.49 (3H, t), 4.514.56 (2H, m), 7.91 (1H, d), 8.71 (1H, d), 9.26 (1H, s). Mass Spectrum: m/z (ES+)[M+H]+=334.

Ethyl 6-bromo-4-chloro-7-fluoroquinoline-3-carboxylate was also prepared on a larger scale according to the following procedure. DMF (0.235 L, 2.56 mol) was added to ethyl 6-bromo-7-fluoro-1-[(4-methoxyphenyl)methyl]-4-oxo-quinoline-3-carboxylate (13.53 kg, 30.43 mol, 97.7 mass %) in toluene (90 L) under an inert atmosphere. The resulting suspension was stirred and heated to 88° C. over 48 minutes. A solution of thionyl chloride (3.32 L, 45.7 mol) in toluene (1.65 L) was then added to the mixture over 4 h 10 min., maintaining the temperature of the mixture in the range 89-91° C. The mixture was held at 89° C. for 50 minutes then analysed by HPLC which indicated completion of the reaction (no starting material detected). The mixture was cooled to 20° C. over 1 h and held overnight at this temperature. The mixture was discharged from the reaction vessel and the vessel rinsed with toluene (13 L). The rinse was added to the main batch. The batch was split into two equal halves and the first half treated as follows: it was evaporated to dryness over approx. 5 h on a 50 L rotary evaporator (batch added in portions as evaporation progressed, bath temperature 60° C., vacuum set point 50 mbar) and the residue treated with heptane (13.2 L) and evaporated (bath temperature 60° C., vacuum set point 100 mbar). The heptane treatment (13.2 L) was repeated to give a thick slurry that was diluted by the portion wise addition of further heptane (53 L) and the heptane slurry transferred portion wise to a clean vessel. The second half of the toluene mixture was worked up in the same way and combined with the first half to give a slurry of the crude product in heptane (approximately 106 L). The heptane slurry was heated to 91° C. over 2 h 20 min. by which time the crude product had dissolved; the mixture was then transferred to a clean, pre-heated (jacket set point 90° C.) vessel via an inline filter to remove particulates. A line wash of heptane (5 L) was then applied via the source vessel. Vacuum (450 mbar) was applied to the destination vessel and heptane (46 L) removed by distillation (batch temperature 77-78° C., head temperature 72-73° C.). The vacuum was released with nitrogen and the vessel contents cooled to 49° C. over 45 min, resulting in crystallisation of the product. The slurry was held 48-49° C. for 30 min. then cooled to 20° C. over 1 h and held at 20° C. overnight. The slurry was filtered, and the source vessel rinsed with heptane (14 L) for 5 mins, then the rinse was applied as a wash to the product cake. A further rinse and wash of heptane (14 L) was then applied and the cake sucked dry over 1 h. The collected solid was transferred to a vacuum oven and dried in vacuo at 50° C. to afford the desired material as an off-white solid (8.915 kg, 26.75 mol, 99.8 mass %, 87.9% Yield).

Intermediate A7: Ethyl 6-bromo-7-fluoro-1-[(4-methoxyphenyl)methyl]-4-oxo-quinoline-3-carboxylate

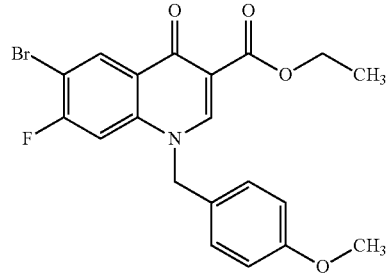 [SMILES: CCOC(=O)c1cn(Cc2ccc(OC)cc2)c2cc(F)c(Br)cc2c1=O]

DBU (76 mL, 506.32 mmol) was added slowly to ethyl-2-(5-bromo-2,4-difluoro-benzoyl)-3-[(4-methoxyphenyl)methylamino]prop-2-enoate (230 g, 506.32 mmol) in acetone (800 mL) at 10° C. over a period of 5 minutes under an inert atmosphere and the resulting mixture stirred at ambient temperature for 16 h. The precipitate was collected by filtration, washed with Et$_2$O (3×500 mL) and dried under vacuum to afford the desired material as a white solid (166 g, 75%). NMR Spectrum: $^1$H NMR (400 MHz, DMSO-d6) δ 1.29 (3H, t), 3.72 (3H, s), 4.22-4.27 (21H, m), 5.57 (2H, s), 6.92-6.95 (2H, m), 7.24 (2H, d), 7.79 (1H, d), 8.40 (1H, d), 8.89 (1H, s). Mass Spectrum: m/z (ES+)[M+H]+=434.

Intermediate A8: Ethyl-2-(5-bromo-2,4-difluoro-benzoyl)-3-[(4-methoxyphenyl)methylamino]prop-2-enoate

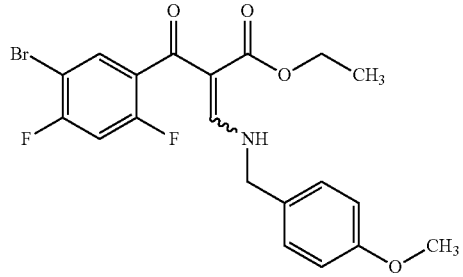 [SMILES: CCOC(=O)C(=CNCc1ccc(OC)cc1)C(=O)c1cc(Br)c(F)cc1F]

(E)-Ethyl 3-(dimethylamino)acrylate (80 mL, 555.50 mmol) was added dropwise to a mixture of DIPEA (132 mL, 757.50 mmol) and 5-bromo-2,4-difluoro-benzoyl chloride (129 g, 505.00 mmol) in toluene (600 mL) at ambient temperature under an inert atmosphere. The resulting solution was stirred at 70° C. for 17 h then allowed to cool. (4-Methoxyphenyl)methanamine (66.0 mL, 505.29 mmol) was added portionwise to the mixture and the reaction stirred for 3 h at ambient temperature. The reaction mixture was diluted with DCM (2 L), washed sequentially with water (4×200 mL), saturated brine (300 mL), the organic layer dried over Na$_2$SO$_4$, filtered and evaporated to afford the desired material as a light brown solid (230 g, 100%) which was used in the next step without further purification. NMR Spectrum: $^1$H NMR (400 MHz, CDCl$_3$) δ 1.09 (3H, t), 3.82 (3H, s), 4.00-4.10 (2H, m), 4.55 (2H, t), 6.84-6.96 (3H, m), 7.20-7.29 (2H, m), 7.55 (1H, d), 8.18 (1H, t). Mass Spectrum: m/z (ES+)[M+H]+=454.

Intermediate A9: 5-Bromo-2,4-difluoro-benzoyl chloride

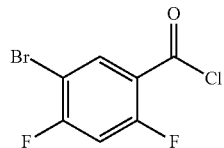 [SMILES: O=C(Cl)c1cc(Br)c(F)cc1F]

Thionyl chloride (55.4 mL, 759.50 mmol) was added portionwise to a mixture of DMF (7.84 mL, 101.27 mmol) and 5-bromo-2,4-difluorobenzoic acid (120 g, 506.33 mmol) in toluene (600 mL) at 15° C. over a period of 5 minutes under an inert atmosphere. The resulting mixture was stirred at 70° C. for 4 h then evaporated to dryness and the residue was azeotroped with toluene to afford the desired material as a brown oil (129 g, 100%) which was used directly in the next step without purification. NMR Spectrum: $^1$H NMR (400 MHz, CDCl$_3$) δ 7.04-7.09 (1H, m), 8.34-8.42 (1H, m).

Intermediate A10: 6-Bromo-7-fluoro-4-(isopropylamino)quinoline-3-carboxamide

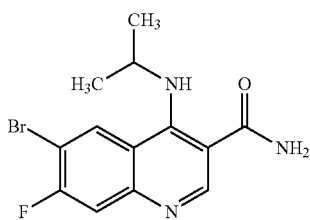 [SMILES: CC(C)Nc1c(C(N)=O)cnc2cc(F)c(Br)cc12]

Propan-2-amine (2.80 ml, 32.62 mmol) was added to a suspension of 6-bromo-4-chloro-7-fluoro-quinoline-3-carboxamide (10 g, 29.65 mmol) and potassium carbonate (8.20 g, 59.31 mmol) in acetonitrile (250 mL) and the mixture stirred at 95° C. for 4 h. Further propan-2-amine (2 mL) was added and the mixture stirred at 95° C. for another 4 h then at ambient temperature overnight. Water was added to the mixture and the solid collected by filtration and dried under vacuum to afford the desired material (8.25 g, 85%). NMR Spectrum: $^1$H NMR (500 MHz, DMSO-d6) δ 1.25 (6H, d), 4.17 (1H, d), 7.51 (1H, s), 7.69 (1H, d), 8.11 (2H, s), 8.61 (1H, s), 8.67 (1H, d). Mass Spectrum: m/z (ES+)[M+H]+=236.

Intermediate A11: 6-Bromo-4-chloro-7-fluoro-quinoline-3-carboxamide

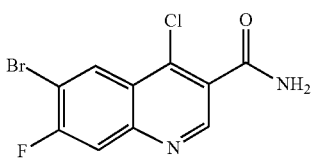 [SMILES: NC(=O)c1cnc2cc(F)c(Br)cc2c1Cl]

DMF (0.5 mL) was added to a stirred suspension of 6-bromo-7-fluoro-4-oxo-1H-quinoline-3-carboxylic acid (22.5 g, 78.66 mmol) in thionyl chloride (140 g, 1179.85 mmol) and the mixture heated to reflux for 2 h. The reaction was allowed to cool, concentrated in vacuo and the residue azeotroped twice with toluene to afford a yellow solid. This solid was added portionwise to a solution of ammonium hydroxide (147 mL, 1179.85 mmol) at 0° C. The white suspension was stirred for 15 minutes then the solid filtered, washed with water and dried under vacuum to afford the desired material (23.80 g, 100%) as a white powder. NMR Spectrum: $^1$H NMR (400 MHz, DMSO-d6) δ 8.92 (1H, s), 8.59 (1H, d), 8.21 (1H, s), 8.09 (1H, d), 7.98 (1H, s). Mass Spectrum: m/z (ES+)[M+H]+=304.8.

Intermediate A12: 6-Bromo-7-fluoro-4-oxo-1H-quinoline-3-carboxylic acid

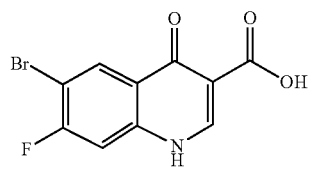 [SMILES: O=C(O)c1c[nH]c2cc(F)c(Br)cc2c1=O]

A solution of sodium hydroxide (18.34 g, 458.44 mmol) in water (100 mL) was added to a stirred suspension of ethyl 6-bromo-7-fluoro-4-oxo-1H-quinoline-3-carboxylate (28.8 g, 91.69 mmol) in EtOH (500 mL) at ambient temperature. The reaction mixture was then stirred at 75° C. for 2 h, allowed to cool and the pH adjusted to 4 using 2N hydrochloric acid. The precipitate was collected by filtration, washed with water and dried under vacuum to afford the desired material (23.30 g, 89%) as a white powder. NMR Spectrum: $^1$H NMR (400 MHz, DMSO-d6) δ 14.78 (1H, s), 13.45 (1H, s), 8.93 (1H, s), 8.46 (1H, d), 7.70 (1H, d). Mass Spectrum: m/z (ES+)[M+H]+=287.8.

Intermediate A13: Ethyl 6-bromo-7-fluoro-4-oxo-H-quinoline-3-carboxylate

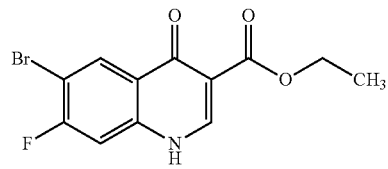 [SMILES: CCOC(=O)c1c[nH]c2cc(F)c(Br)cc2c1=O]

A solution of diethyl 2-[(4-bromo-3-fluoro-anilino)methylene]propanedioate (90 g, 249.88 mmol) in diphenyl ether (600 mL, 3.79 mol) was stirred at 240° C. for 2.5 h. The mixture was allowed to cool to 70° C., the solids collected by filtration and dried in a vacuum oven to afford the desired material (50 g, 64%) as a white solid which was used without further purification. NMR Spectrum: $^1$H NMR (500 MHz, DMSO-d6, (100° C.)) δ 1.26-1.33 (3H, m), 4.25 (2H, q), 7.52 (1H, d), 8.37 (1H, d), 8.48 (1H, s), 12.05 (1H, s). Mass Spectrum: m/z (ES+)[M+H]+=314.

Intermediate A14: Diethyl 2-[(4-bromo-3-fluoroanilino)methylene]propanedioate

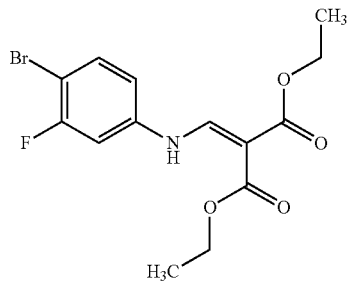 [SMILES: CCOC(=O)C(=CNc1ccc(Br)c(F)c1)C(=O)OCC]

A solution of 4-bromo-3-fluoroaniline (56.6 g, 297.87 mmol) and 1,3-diethyl 2-(ethoxymethylidene)propanedioate (72.45 g, 335.06 mmol) in EtOH (560 mL) was stirred at 80° C. for 4 h. The reaction mixture was allowed to cool, the solids collected by filtration and dried in an oven to afford the desired material (90 g, 84%) as an off-white solid which was used without further purification. NMR Spectrum: $^1$H NMR (400 MHz, DMSO-d6) δ 1.26 (6H, q), 4.14 (2H, q), 4.22 (2H, q), 7.18-7.25 (1H, m), 7.57 (1H, dd), 7.64-7.7 (H, in), 8.33 (1H, d), 10.62 (1H, d). Mass Spectrum: m/z (ES+)[M+H]+=360.

8-[6-[3-(Dimethylamino)propoxy]-3-pyridyl]-7-fluoro-1-isopropyl-3-methyl-imidazo[4,5-c]quinolin-2-one can also be prepared directly from 8-bromo-7-fluoro-1-isopropyl-3-methyl-imidazo[4,5-c]quinolin-2-one using the method described below.

3-(Di-tert-butylphosphino)propane-1-sulfonic acid (0.467 mg, 1.77 mmol) was added to monopalladium(IV) disodium tetrachloride (0.261 g, 0.89 mmol) in water (50 mL) under an inert atmosphere. The resulting mixture was stirred at ambient temperature for 20 minutes, then the reaction mixture was added in one portion to 8-bromo-7-fluoro-1-isopropyl-3-methyl-imidazo[4,5-c]quinolin-2-one, N,N-dimethyl-3-[5-(4,4,5,5-tetramethyl-1,3,2-dioxaborolan-2-yl)pyridin-2-yl]oxypropan-1-amine (42.4 g, 110.89 mmol) and potassium carbonate (36.8 g, 266.13 mmol) in dioxane (500 mL) and water (100 mL) at ambient temperature under an inert atmosphere. The resulting solution was stirred at 80° C. for 2 h. The reaction solution was concentrated under vacuum and diluted with DCM. The organic phase was dried over Na$_2$SO$_4$, filtered and evaporated to afford to crude product. The crude was purified by silica, elution gradient 0 to 2% MeOH (7M ammonia in MeOH) in DCM, to afford a solid which was triturated with MeCN to afford the desired material as a yellow solid (25.00 g, 64.4%). The pure material was combined with additional material prepared in an analogous fashion (38.6 g total) and was heated in MeCN (100 mL) for 10 min then allowed to cool to 0° C. and stirred for 2 h. The solid was filtered under vacuum and dried in a vacuum oven for 16 h to afford the desired material as a pale yellow crystalline solid (35.5 g). The analytical data was consistent with that from material prepared previously.

Intermediate B1: N,N-Dimethyl-3-[5-(4,4,5,5-tetramethyl-1,3,2-dioxaborolan-2-yl)pyridin-2-yl]oxypropan-1-amine

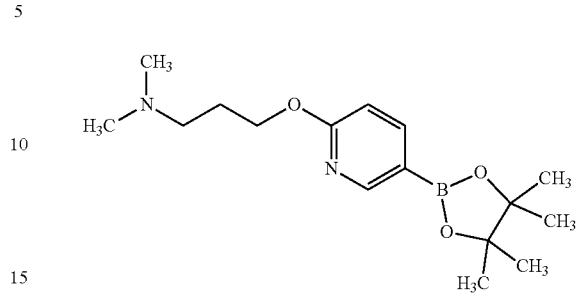

n-Butyllithium (2.5 M, 0.147 L, 368.21 mmol) was added dropwise to 3-(5-bromopyridin-2-yl)oxy-N,N-dimethylpropan-1-amine (73.4 g, 283.24 mmol) and 2-isopropoxy-4,4,5,5-tetramethyl-1,3,2-dioxaborolane (68.5 g, 368.21 mmol) in THF (1 L) cooled to −78° C. over a period of 10 minutes under an inert atmosphere. The resulting mixture was allowed to warm to ambient temperature and stirred for 2 h. The reaction mixture was quenched with a saturated aqueous solution of ammonium chloride (50 mL). The solvent was removed under reduced pressure and diluted with EtOAc (2 L), the organic layer was dried over Na$_2$SO$_4$, filtered and evaporated to afford the desired material as a yellow oil (98 g, 113%). The product was used in the next step directly without further purification. NMR Spectrum: $^1$H NMR (300 MHz, CDCl$_3$) δ 1.30 (12H, s), 1.93-2.09 (2H, m), 2.33 (6H, s), 2.49-2.61 (2H, m), 4.37 (2H, t), 6.69 (1H, dd), 7.91 (1H, dd), 8.51 (1H, d).

Intermediate B2: 3-(5-Bromopyridin-2-yl)oxy-N,N-dimethylpropan-1-amine

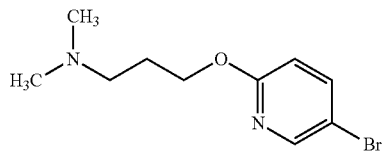

Sodium hydride (17.05 g, 426.17 mmol) was added portionwise to 3-(dimethylamino)propan-1-ol (35.2 g, 340.94 mmol) in THF (500 mL) at 5° C. and the mixture allowed to warm to ambient temperature. 5-Bromo-2-fluoropyridine (50 g, 284.11 mmol) was added and the solution stirred at 50° C. for 2 h. The reaction solution was added carefully to ice-water and the aqueous phase was extracted with DCM (3×700 mL). The organic phase was dried over Na$_2$SO$_4$, filtered and evaporated to afford the desired material as a yellow oil (73.6 g, 100%). The material was used without further purification. NMR Spectrum: $^1$H NMR (300 MHz, CDCl$_3$) δ 1.92-2.01 (2H, m), 2.28 (6H, s), 2.45 (2H, t), 4.33 (2H, t), 6.67 (1H, dd), 7.65 (1H, dd), 8.20 (1H, d). Mass Spectrum: m/z (ES+)[M+H]+=259.

Example 2

7-Fluoro-1-isopropyl-3-methyl-8-[6-[3-(1-piperidyl)propoxy]-3-pyridyl]imidazo[4,5-c]quinolin-2-one

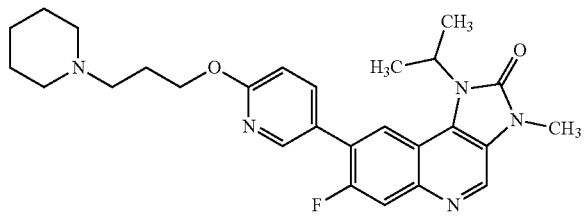 [SMILES: CC(C)n1c(=O)n(C)c2cnc3cc(F)c(-c4ccc(OCCCN5CCCCC5)nc4)cc3c21]

3-(Piperidin-1-yl)propan-1-ol (1.051 g, 7.34 mmol) in THF (15 mL) was added slowly to a slurry of sodium hydride (0.587 g, 14.67 mmol) in THF (15 mL) and the solution stirred at 50° C. for 40 minutes. A mixture of 7-fluoro-8-(6-fluoro-3-pyridyl)-1-isopropyl-3-methyl-imidazo[4,5-c]quinolin-2-one (2.0 g, 5.64 mmol) in THF (15 mL) was added and the reaction stirred for 6 h at 50° C. then allowed to cool to r.t. and quenched with water. Solid precipitation was observed upon standing and was collected by filtration. The material was purified by flash silica chromatography, elution gradient 0 to 10% MeOH in DCM, then by preparative HPLC (redisep gold C18 column, 80 g), using decreasingly polar mixtures of water (containing 0.1% ammonia) and MeCN as eluents, to afford the desired material. The product was recrystallized from boiling EtOH to afford desired material as a white solid (1.512 g, 56.1%). NMR Spectrum: $^1$H NMR (500 MHz, DMSO-d6) δ 1.34-1.44 (2H, m), 1.50 (4H, p), 1.65 (6H, d), 1.91 (2H, p), 2.29-2.37 (4H, m), 2.39 (2H, q), 3.51 (3H, s), 4.37 (2H, t), 5.29 (1H, p), 6.99 (1H, dd), 7.92 (1H, d), 8.05 (1H, dt), 8.33 (1H, d), 8.50 (1H, s), 8.91 (1H, s). Mass Spectrum: m/z (ES+)[M+H]+=478.

The desired material can also be isolated as the methane sulfonic acid salt as follows. Methanesulfonic acid (0.026 g, 0.27 mmol) in DCM (0.5 mL) was added to the isolated free base (127 mg, 0.27 mmol) at ambient temperature. The resulting solution was stirred at ambient temperature for 15 minutes then concentrated in vacuo and the residue dried under vacuum to afford the desired methanesulfonic acid salt as a white solid (336 mg, 100%). NMR Spectrum: $^1$H NMR (500 MHz, CDCl$_3$) δ 1.78 (6H, d), 1.86-1.99 (4H, m), 2.11-2.25 (2H, m), 2.37-2.48 (2H, m), 2.6-2.74 (2H, m), 2.84 (3H, s), 3.22-3.31 (2H, m), 3.59 (3H, s), 3.69 (2H, d), 4.48-4.56 (2H, m), 5.17-5.27 (1H, m), 6.90 (1H, dd), 7.90 (1H, dt), 7.96 (1H, d), 8.23 (1H, d), 8.39 (1H, d), 8.76 (1H, s), 10.75 (1H, s).
Mass Spectrum: m/z (ES+)[M+H]+=478.

7-Fluoro-1-isopropyl-3-methyl-8-[6-[3-(1-piperidyl)propoxy]-3-pyridyl]imidazo[4,5-c]quinolin-2-one can also be prepared directly from 8-bromo-7-fluoro-1-isopropyl-3-methyl-imidazo[4,5-c]quinolin-2-one using the method described below.

3-(Di-tert-butylphosphino)propane-1-sulfonic acid (0.555 mg, 2.07 mmol) was added to monopalladium(IV) disodium tetrachloride (0.304 g, 1.03 mmol) in water (12 mL) under an inert atmosphere. The resulting mixture was stirred at ambient temperature for 10 minutes, then the reaction mixture was added in one portion to 8-bromo-7-fluoro-1-isopropyl-3-methyl-imidazo[4,5-c]quinolin-2-one (35.0 g, 103.50 mmol), 2-[3-(1-piperidyl)propoxy]-5-(4,4,5,5-tetramethyl-1,3,2-dioxaborolan-2-yl)pyridine (62.2 g, 129.37 mmol) and potassium carbonate (42.9 g, 310.49 mmol) in dioxane (450 mL) and water (90 mL) at ambient temperature under an inert atmosphere. The resulting solution was stirred at 80° C. for 16 h and the reaction evaporated. The crude material was dissolved in DCM (500 mL), was washed with brine (2×100 mL), the organic phase dried over Na$_2$SO$_4$, filtered and evaporated. The crude product was purified by flash silica chromatography, elution gradient 0 to 10% (0.1% ammonia in MeOH) in DCM, to afford the desired material as a brown solid (40.5 g, 82%). The material was combined with material obtained from analogous preparations (total 51.3 g) and slurried in MeCN (100 mL). The precipitate was collected by filtration, washed with MeCN (100 mL) and dried under vacuum to the desired material as a white solid (32.0 g, 62.4%). The analytical data was consistent with that from previously prepared samples.

The material obtained from the MeCN slurry was found to be crystalline form A of Example 2. Example 2 Form A is characterised in providing an X-ray powder diffraction pattern substantially as shown in FIG. 1. Ten X-Ray powder diffraction peaks are shown in Table 1.

TABLE 1

Characteristic X-Ray powder diffraction peaks for Form A of Example 2, 7-Fluoro-1-isopropyl-3-methyl-8-[6-[3-(1-piperidyl)propoxy]-3-pyridyl]imidazo[4,5-c]quinolin-2-one

| Angle 2-Theta (2θ) | Intensity % |
|---|---|
| 3.7 | 100 |
| 14.8 | 77 |
| 18.4 | 57 |
| 21.0 | 56 |
| 11.3 | 44 |
| 19.4 | 34 |
| 22.3 | 34 |
| 18.0 | 33 |
| 23.2 | 30 |
| 13.1 | 30 |

Example 2 Form A displays a melting endotherm with an onset of 141.5° C. and a peak at 144.2° C. when analysed by differential scanning calorimetry (DSC) at a scanning rate of 10° C./mins (FIG. 2).

A further method of preparing 7-Fluoro-1-isopropyl-3-methyl-8-[6-[3-(1-piperidyl)propoxy]-3-pyridyl]imidazo[4,5-c]quinolin-2-one is as follows. A 250 mL flask was purged with nitrogen three times. Sodium tetra-chloropalladate (2.51 g, 8.5 mmol.), 3-(di-tert-butylphosphino)propane-1-sulfonic acid (4.36 g, 16.2 mmol.) and water (95 mL) were charged. The phosphine ligand mixture was left to stir under nitrogen at room temperature for 10 minutes. A 10 L flange flask was purged with nitrogen three times. 8-Bromo-7-fluoro-1-isopropyl-3-methyl-imidazo[4,5-c]quinolin-2-one (281.3 g, 0.83 mol.), 2-[3-(1-piperidyl)propoxy]-5-(4,4,5,5-tetramethyl-1,3,2-dioxaborolan-2-yl)pyridine (360.0 g, 1.04 mol.), potassium carbonate (347.2 g. 2.51 mol.), dioxane (3.6 L, 12.9 vol.) and water (720 mL, 2.6 vol.) were charged to the flange flask. The pre-mixed phosphine ligand catalyst mixture was quickly charged into the reaction mixture (10 L flange flask) under nitrogen. The reaction mixture was then heated at 80° C. under nitrogen atmosphere and monitored by HPLC. After 2 h, analysis showed the reaction was complete with low level (0.30%) of starting material remaining. The reaction mixture was cooled to room temperature (20° C.) under nitrogen then concentrated under reduced pressure. The resultant residue was taken up in DCM (4 L, 14.3 vol.) forming a dark brown/green solution. The solution was washed with saturated brine solution (2×780 mL), and the organic layer was separated off. The aqueous layer was back extracted with dichloromethane (1250 mL, 4.5 vol.), and the combined organic layer was filtered to remove a green solid precipitate (assumed to be catalyst related impurities), before it was dried over sodium sulphate (782.7 g) and concentrated under vacuum to give a dichloromethane wet yellow solid. The crude material was dried under vacuum in an oven at 40° C. overnight, to give a 492.7 g (335.0 g active) of crude product. Analysis indicated the material was 95.0% pure by HPLC and 68% active by NMR Assay. The second batch was completed on the same scale to obtain a further 494.2 g (326.2 g active) of crude product. Analysis indicated the material was 88.0% pure by HPLC and 66% active by NMR Assay. The two batches were combined to give a total crude mass of 968.4 g (661 g active) which was passed through silica (12 kg) using an eluent gradient mixture of DCM with methanol (0-40%) and ammonia (0-0.2%), (total solvent usage: 285 litres). The product containing fractions (>97% by liquid chromatography) were combined and concentrated under vacuum, slurried in methanol (2 volumes) overnight and dried under vacuum at 50° C. to give a white solid, 392.9 g, 49.5% yield. The product containing fractions (<97% by liquid chromatography) were combined and concentrated under vacuum and slurried in ethyl acetate for 2 h. The resulting solid was then slurried in methanol (2 vol) to give an additional 111.3 g of product. Both batches were combined and slurried in heptane (5 vol.) for 1 h 30 min, before filtering and drying under vacuum in an oven at 50° C. overnight. This gave a total yield of 487.2 g (61%) with a purity of 96% by $^1$H NMR assay.

The material obtained from the preparation above was found to be crystalline form B of Example 2. Example 2 Form B is characterised in providing an X-ray powder diffraction pattern substantially as shown in FIG. 3. Ten X-Ray powder diffraction peaks are shown in Table 2.

TABLE 2

Characteristic X-Ray powder diffraction peaks for Form B of Example 2, 7-Fluoro-1-isopropyl-3-methyl-8-[6-[3-(1-piperidyl)propoxyl-3-pyridyl] imidazo[4,5-c]quinolin-2-one

| Angle 2-Theta (2θ) | Intensity % |
|---|---|
| 3.4 | 42 |
| 11.7 | 67 |
| 22.7 | 100 |
| 13.5 | 64 |
| 13.1 | 45 |
| 19.0 | 42 |
| 23.4 | 30 |
| 24.0 | 21 |
| 17.5 | 18 |
| 18.1 | 15 |

Example 2 Form B displays a melting endotherm with an onset of 144.7° C. and a peak at 145.8° C. when analysed by differential scanning calorimetry (DSC) at a scanning rate of 10° C./mins (FIG. 4).

7-Fluoro-1-isopropyl-3-methyl-8-[6-[3-(1-piperidyl) propoxy]-3-pyridyl]imidazo[4,5-c]quinolin-2-one can be prepared on a large scale using the following procedure. Under an atmosphere of nitrogen, 8-bromo-7-fluoro-1-isopropyl-3H-imidazo[4,5-c]quinolin-2-one (0.800 kg, 2.31 mol, 97.6 mass %) was charged to a vessel followed by 2-[3-(1-piperidyl)propoxy]-5-(4,4,5,5-tetramethyl-1,3,2-dioxaborolan-2-yl)pyridine (0.879 kg, 2.54 mol) and potassium carbonate (0.960 kg, 6.95 mol). THF (8 L) and water (3.9 L) were then added and stirring of the mixture initiated. Vacuum was gradually applied until the THF just started to boil (135 mbar) and then released with nitrogen. The vacuum purge procedure was repeated twice more (approx. 0.5 L THF lost to receiver) and a slow trickle of nitrogen applied to the vessel. Dichloro[1,1'-bis(di-tertbutylphosphino)ferrocene]palladium(II) (Pd-118, 15 g, 0.023 mol) was added via a glove bag and the mixture heated to 63-64° C. and held at this temperature for 2 h then analysed by HPLC which indicated acceptable conversion to the desired product. The mixture was cooled to 20° C., stirring was stopped and the mixture allowed to separate and the lower aqueous phase run off to waste. A solution of brine made up from water (3.45 L) and sodium chloride (0.586 kg) was charged to the organic phase in the vessel and the mixture stirred for 10 mins then allowed to separate. The aqueous phase was run off to waste and the organic phase filtered through a bed of celite (150 g). The vessel was rinsed with THF (800 mL) and the rinse put through the celite cake and added to the organic filtrate. The combined THF filtrate (ca. 9.5 L) was charged to a clean vessel and metal scavenging aid Phosphonics SPM 32 (780 g) added. The mixture was stirred at 21° C. for 16 h then filtered to remove the insoluble scavenging aid. A rinse of THF (1.6 L) was applied to the reactor vessel and passed through the filter. The combined filtrate and rinse were then transferred to a clean vessel and solvent (6.9 L) distilled off at reduced pressure (23-24° C., 150 mbar). Isopropanol (11 L) was added to the residue in the reactor, and a further amount of solvent (9.2 L) removed by distillation at reduced pressure (40-43° C. batch temperature, 150 mbar). The concentrated mixture in the vessel was heated to 80° C. and stirring rate increased to wash down and dissolve product that had been observed to crystallise on the vessel walls. The hot solution was transferred via an in-line filter to a clean dry, pre-heated (jacket temperature 80° C.) receiving vessel, equipped with a Lasentec FBRM probe. The transferred solution was cooled to 60° C. and seeded with the desired product (Form B, 0.44 g) and stirred at 58-60° C. for 5 h, then cooled to 20° C. over 14 h to crystallise the product. The slurry was sampled and analysed by XRPD that indicated it to be a mixture of polymorphs (Form B and Form A—major component). The mixture was heated to 48-50° C. and re-sampled and adjudged to be still a mixture of polymorphs. The slurry was then diluted with isopropanol (1.5 L) and stirred and heated at 50° C. for approx. 67 h by which time the amount of the desired Form B had increased to approx. 50%. 2 L of the mixture was removed to perform laboratory studies and the remaining bulk of the slurry then heated at 56° C. for a further approx. 21 h by which time it had converted to Form B. The slurry was then cooled to 10° C. over 20 h and held at 10-11° C. for approx. 5 h then filtered. A wash of isopropanol (2.2 L) was applied to the product cake via the crystallisation vessel. The cake was sucked dry for 20 mins on the filter and then dried in vacuo at 50° C. for approximately 22 h to afford the desired product as its Form B polymorph, (824 g, 1.729 mol, 100 mass %, 74.9% Yield).

Intermediate C1: 2-[3-(1-piperidyl)propoxy]-5-(4,4,5,5-tetramethyl-1,3,2-dioxaborolan-2-yl)pyridine

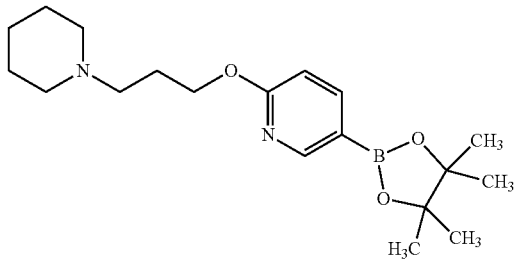 [SMILES: CC1(C)OB(c2ccc(OCCCN3CCCCC3)nc2)OC1(C)C]

n-Butyllithium (139 mL, 347.59 mmol) was added dropwise to 5-bromo-2-[3-(1-piperidyl)propoxy]pyridine (80 g, 267.37 mmol) and 2-isopropoxy-4,4,5,5-tetramethyl-1,3,2-dioxaborolane (64.7 g, 347.59 mmol) in THF (400 mL) cooled to −78° C. over a period of 10 minutes under an inert atmosphere. The resulting mixture was allowed to warm to ambient temperature and stirred for 12 h. The reaction mixture was quenched with a saturated aqueous solution of ammonium chloride (100 mL) and the mixture concentrated under reduced pressure. The mixture was extracted with EtOAc (2×500 mL), the organic layer washed with saturated brine (2×100 mL), dried over $Na_2SO_4$, filtered and evaporated to afford the desired material as a yellow oil (92 g, 99%). The product was used in the next step directly without further purification. NMR Spectrum: $^1$H NMR (400 MHz, $CDCl_3$) δ 1.34 (12H, s), 1.60 (5H, p), 1.93-2.08 (3H, m), 2.39-2.53 (6H, m), 4.34 (2H, dt), 6.67-6.77 (1H, m), 7.92 (1H, dd), 8.50-8.56 (1H, m).

Intermediate C2: 5-Bromo-2-[3-(1-piperidyl)propoxy]pyridine

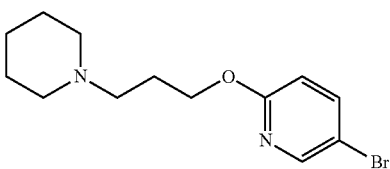 [SMILES: Brc1ccc(OCCCN2CCCCC2)nc1]

Sodium hydride (20.91 g, 522.77 mmol) was added portionwise to 3-(piperidin-1-yl)propan-1-ol (35.8 g, 250.02 mmol) in THF (400 mL) at ambient temperature under an inert atmosphere. The resulting suspension was stirred at 50° C. for 30 minutes then allowed to cool and 5-bromo-2-fluoropyridine (40.0 g, 227.29 mmol) added. The solution was stirred at 50° C. for 2 h then allowed to cool. The reaction was repeated in analogues fashion using sodium hydride (5.23 g, 130.69 mmol), 3-(piperidin-1-yl)propan-1-ol (8.95 g, 62.50 mmol), THF (100 mL) and 5-bromo-2-fluoropyridine (10 g, 56.82 mmol). The two reaction mixtures were combined and poured into ice/water (1000 mL). The solvent was concentrated under reduced pressure and extracted with DCM (3×150 mL), the organic layer was washed with saturated brine (3×150 mL), dried over $Na_2SO_4$, filtered and evaporated to afford the desired material as a brown oil (96 g, 113%). The material was used without further purification. NMR Spectrum: $^1$H NMR (400 MHz, $CDCl_3$) δ 1.43-1.49 (2H, m), 1.61 (5H, p), 1.99 (2H, dq), 2.46 (6H, dd), 4.31 (2H, t), 6.65 (1H, d), 7.64 (1H, dd), 8.19 (1H, d). Mass Spectrum: m/z (ES+)[M+H]+=299.

Example 3

7-Fluor-1-isopropyl-3-methyl-8-[6-(3-pyrrolidin-1-ylpropoxy)-3-pyridyl]imidazo[4,5-c]quinolin-2-one

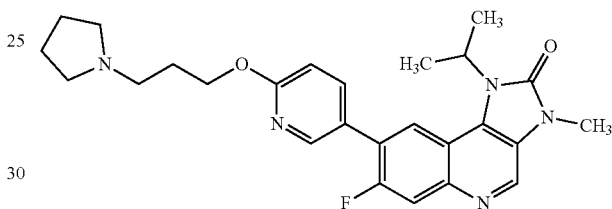

3-(Pyrrolidin-1-yl)propan-1-ol (62.0 mg, 0.48 mmol) was added to sodium hydride (13.54 mg, 0.56 mmol) in THF (5 mL) at r.t. under an inert atmosphere and the reaction stirred for 20 minutes. 7-Fluoro-8-(6-fluoro-3-pyridyl)-1-isopropyl-3-methyl-imidazo[4,5-c]quinolin-2-one (100 mg, 0.28 mmol) was added and the reaction stirred for 16 h. The reaction mixture was quenched with saturated $NH_4Cl$ (15 mL), extracted with DCM (3×15 mL), the organic layer dried over $Na_2SO_4$, filtered and evaporated to afford crude product. The crude product was purified by preparative HPLC (XSelect CSH Prep C18 OBD column, 5μ silica, 19 mm diameter, 150 mm length), using decreasingly polar mixtures of water (containing 0.1% Formic acid) and MeCN as eluents, to afford the desired material as a white solid (85 mg, 61.9%). NMR Spectrum: $^1$H NMR (300 MHz, $CDCl_3$) δ 1.78 (6H, d), 1.99-2.10 (4H, m), 2.31 (2H, dt), 3.03-3.15 (6H, m), 3.59 (3H, s), 4.47 (2H, t), 5.23 (1H, s), 6.85-6.94 (1H, m), 7.85-7.97 (2H, m), 8.21 (1H, d), 8.41 (1H, s), 8.71 (1H, s). Mass Spectrum: m/z (ES+)[M+H]+=464.

The following compound was prepared in an analogous fashion.

| Example | Structure | Name |
|---|---|---|
| 4 | 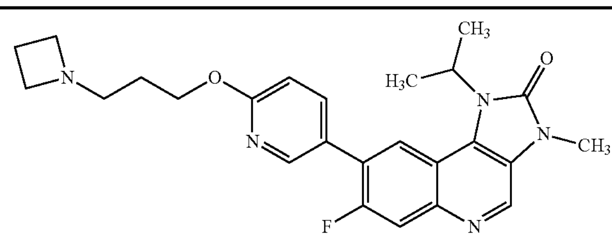 | 8-[6-[3-(azetidin-1-yl)propoxy]-3-pyridyl]-7-fluoro-1-isopropyl-3-methyl-imidazo[4,5-c]quinolin-2-one |

Example 4

NMR Spectrum: ¹H NMR (300 MHz, CDCl₃) δ 1.75-1.78 (6H, s), 2.08-2.15 (2H, q), 2.40-2.50 (2H, m), 3.08-3.14 (2H, m), 3.59 (3H, s), 3.87-3.92 (4H, t), 4.42-4.46 (2H, t), 5.18-5.26 (1H, m), 6.88-6.91 (1H, m), 7.87-7.93 (2H, m), 8.21 (1H, d), 8.41 (1H, s), 8.71 (1H, s). Mass Spectrum: m/z (ES+)[M+H]+=450.

Intermediate D1: 3-(Azetidin-1-yl)propan-1-ol

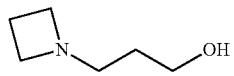

A solution of lithium aluminium hydride (2.0 M in THF) (8.38 mL, 16.76 mmol) diluted in further THF (20 mL) was added to a mixture of methyl 3-(azetidin-1-yl)propanoate (2 g, 13.97 mmol) in THF (5 mL) dropwise at 0° C. under an inert atmosphere. The resulting solution was stirred at 0° C. for 1 h then the reaction mixture treated with sodium sulphate decahydrate and stirred for 30 minutes. The solid was removed by filtration and discarded and the filtrate evaporated to afford the desired material (1.240 g, 77%) as a colourless oil. NMR Spectrum: ¹H NMR (400 MHz, CDCl₃) δ 1.51-1.57 (2H, m), 2-2.07 (2H, m), 2.6-2.66 (2H, m), 3.20 (4H, t), 3.7-3.76 (2H, m).

Intermediate D2: Methyl 3-(azetidin-1-yl)propanoate

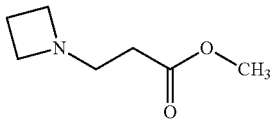

Methyl acrylate (2.082 ml, 23.12 mmol) was added to a solution of azetidine (1.2 g, 21.02 mmol) in DCM and the resulting solution stirred at ambient temperature, under an inert atmosphere for 16 h. The reaction mixture was evaporated and the crude product purified by FCC, eluted with 25% EtOAc in DCM, to afford the desired material (2.0 g, 66.5%) as a colourless oil. NMR Spectrum: ¹H NMR (400 MHz, CDCl₃) δ 1.97-2.1 (2H, m), 2.33 (2H, d), 2.67 (2H, d), 3.18 (4H, t), 3.67 (3H, s).

Example 5

1-Isopropyl-3-methyl-8-[6-[3-(1-piperidyl)propoxy]-3-pyridyl]imidazo[4,5-c]quinolin-2-one

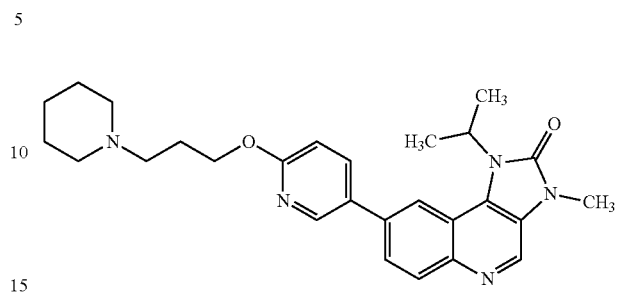

3-(Piperidin-1-yl)propan-1-ol (0.135 mL, 0.89 mmol) was added dropwise to a stirred suspension of sodium hydride (0.071 g, 1.78 mmol) in THF (0.5 mL) at r.t. and the resulting suspension stirred at r.t. for 10 minutes under an inert atmosphere. 8-(6-Fluoro-3-pyridyl)-1-isopropyl-3-methyl-imidazo[4,5-c]quinolin-2-one (0.15 g, 0.45 mmol) in DMF (1.5 mL) was added and the reaction mixture stirred at r.t. for one h. The reaction mixture was diluted with ethyl acetate (40 mL), washed twice with water (20 mL) then the organic layer dried over MgSO₄, filtered and evaporated to afford crude product. The crude product was purified by flash silica chromatography, elution gradient 0 to 3% 2N methanolic ammonia in DCM, to afford the desired material as a white solid (0.154 g, 75%). NMR Spectrum: ¹H NMR (500 MHz, CDCl₃) δ 1.39-1.51 (2H, m), 1.60 (4H, p), 1.79 (6H, d), 2.03 (2H, dt), 2.42 (4H, s), 2.47-2.58 (2H, m), 3.59 (3H, s), 4.42 (2H, t), 5.19-5.41 (1H, m), 6.89 (1H, d), 7.78 (H, dd), 7.90 (1H, dd), 8.22 (1H, d), 8.32 (1H, s), 8.50 (1H, d), 8.70 (1H, s). Mass Spectrum: m/z (ES+)[M+H]+=460.

The above material can also be isolated as the methane sulfonic acid salt by taking the material as prepared above and subjecting to the following reaction conditions.

1-Isopropyl-3-methyl-8-[6-[3-(1-piperidyl)propoxy]-3-pyridyl]imidazo[4,5-c]quinolin-2-one (133 mg, 0.29 mmol) was dissolved in DCM (2 mL) and treated with 1M methanesulfonic acid (0.3 mL, 0.30 mmol) in DCM then the mixture evaporated to dryness. The residue was triturated with diethyl ether to afford the methane sulfonic acid salt as a pale yellow solid (162 mg). NMR Spectrum: ¹H NMR (500 MHz, CDCl₃) δ 1.31-1.5 (1H, m), 1.68 (9H, d), 1.83 (2H, d), 2.13-2.26 (2H, m), 2.32 (3H, s), 2.84-3.01 (2H, m), 3.24 (2H, dt), 3.52 (5H, s), 4.43 (2H, t), 5.38 (1H, p), 7.00 (1H, d), 7.99 (1H, d), 8.17 (1H, d), 8.24 (1H, dd), 8.43 (1H, s), 8.69 (1H, d), 8.95 (1H, s), 9.04 (1H, s). Mass Spectrum: m/z (ES+)[M+H]+=460.

The following compounds were prepared in an analogous fashion from either 8-(6-fluoro-3-pyridyl)-1-isopropyl-3-methyl-imidazo[4,5-c]quinolin-2-one or 7-fluoro-8-(6-fluoro-3-pyridyl)-1-isopropyl-3-methyl-imidazo[4,5-c]quinolin-2-one and the appropriate alcohol.

| Example | Structure | Name |
| --- | --- | --- |
| 6 | 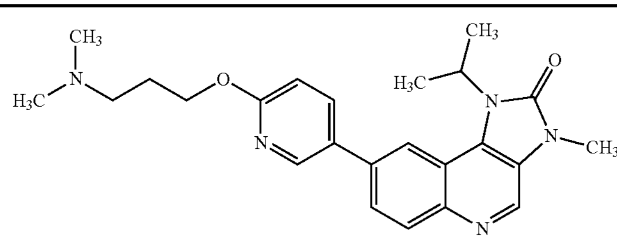 | 8-[6-[3-(dimethylamino)propoxy]-3-pyridyL]-1-isopropy]-3-methyl-imidazo[4,5-c]quinolin-2-one |

| Example | Structure | Name |
|---|---|---|
| 7* | 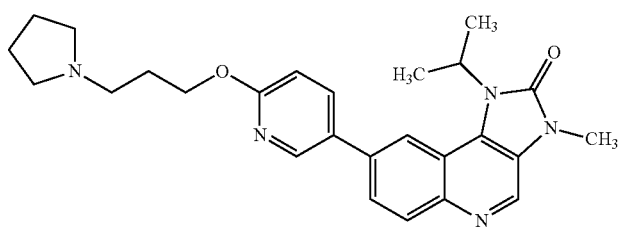 [SMILES: CC(C)n1c(=O)n(C)c2cnc3ccc(-c4ccc(OCCCN5CCCC5)nc4)cc3c21] | 1-isopropyl-3-methyl-8-[6-(3-pyrrolidin-1-ylpropoxy)-3-pyridyl]imidazo[4,5-c]quinolin-2-one |

*Reaction stirred for 2 h at r.t.

Example 6

(Free base) NMR Spectrum: $^1$H NMR (500 MHz, DMSO-d6) δ 1.68 (6H, d), 1.89 (2H, p), 2.16 (6H, s), 2.37 (2H, t), 3.51 (3H, s), 4.37 (2H, t), 5.36 (1H, p), 6.98 (1H, dd), 7.93 (1H, dd), 8.14 (1H, d), 8.18 (1H, dd), 8.40 (1H, d), 8.66 (1H, dd), 8.88 (1H, s). (Methane sulfonic acid salt) NMR Spectrum: $^1$H NMR (500 MHz, DMSO-d6) δ 1.68 (6H, d), 2.07-2.25 (2H, m), 2.33 (3H, s), 2.80 (6H, s), 3.15-3.24 (2H, m), 3.51 (3H, s), 4.42 (2H, t), 5.35 (1H, p), 7.00 (1H, dd), 7.94 (1H, dd), 8.15 (1H, d), 8.23 (1H, dd), 8.40 (1H, d), 8.68 (1H, dd), 8.89 (1H, s). Mass Spectrum: m/z (ES+)[M+H]+=420.

Example 7

(Free base) NMR Spectrum: $^1$H NMR (500 MHz, DMSO-d6) δ 1.61-1.77 (10H, m), 1.93 (2H, p), 2.43-2.49 (4H, m), 2.53-2.59 (2H, m), 3.51 (3H, s), 4.38 (2H, t), 5.29-5.43 (1H, m), 6.97 (1H, dd), 7.93 (1H, dd), 8.13 (1H, d), 8.18 (1H, dd), 8.40 (1H, d), 8.65 (1H, dd), 8.88 (1H, s). (Methane sulfonic acid salt) NMR Spectrum: $^1$H NMR (500 MHz, DMSO-d6) δ 1.68 (6H, d), 1.88 (4H, s), 2.11-2.23 (2H, m), 2.32 (3H, s), 3.08 (2H, s), 3.32 (2H, s), 3.51 (3H, s), 3.60 (2H, s), 4.44 (2H, t), 5.36 (1H, p), 7.01 (1H, d), 7.94 (1H, dd), 8.15 (1H, d), 8.23 (1H, dd), 8.40 (1H, d), 8.68 (1H, d), 8.89 (1H, s), 9.50 (1H, s). Mass Spectrum: m/z (ES+)[M+H]+=446.

Intermediate E1: 8-(6-Fluoro-3-pyridyl)-1-isopropyl-3-methyl-imidazo[4,5-c]quinolin-2-one

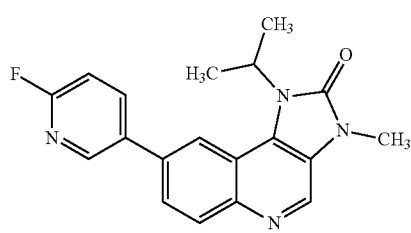 [SMILES: CC(C)n1c(=O)n(C)c2cnc3ccc(-c4ccc(F)nc4)cc3c21]

8-Bromo-1-isopropyl-3-methyl-imidazo[4,5-c]quinolin-2-one (4.57 g, 14.27 mmol), (6-fluoropyridin-3-yl)boronic acid (2.61 g, 18.55 mmol) and 2M potassium carbonate (22 mL, 44.00 mmol) were suspended in 1,4-dioxane (90 mL). The mixture was degassed then dichloro [1,1'-bis(di-tert-butylphosphino)ferrocene] palladium(II) (0.465 g, 0.71 mmol) added and the reaction to 80° C. for 2 h under an inert atmosphere. The mixture was allowed to cool, diluted with EtOAc (200 mL) then washed with water (50 mL), brine, and the organic phase dried over MgSO$_4$, filtered and concentrated in vacuo. The crude product was purified by flash silica chromatography, elution gradient 0 to 5% MeOH in DCM, to afford material which was subsequently triturated with diethyl ether to afford the desired material as an off-white solid (4.46 g, 93%). NMR Spectrum: $^1$H NMR (500 MHz, DMSO-d6) δ 1.66 (6H, d), 3.50 (3H, s), 5.36 (1H, p), 7.36 (1H, dd), 7.95 (1H, dd), 8.15 (1H, d), 8.39-8.52 (2H, m), 8.72 (1H, d), 8.90 (1H, s). Mass Spectrum: m/z (ES+)[M+H]+=337.

Intermediate E2: 8-Bromo-1-isopropyl-3-methyl-imidazo[4,5-c]quinolin-2-one

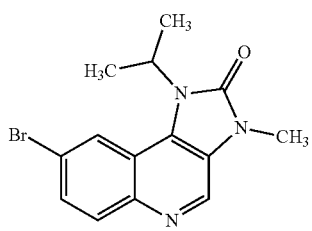 [SMILES: CC(C)n1c(=O)n(C)c2cnc3ccc(Br)cc3c21]

N,N-Dimethylformamide dimethyl acetal (54.2 mL, 408.29 mmol) was added to a solution of 8-bromo-1-isopropyl-3H-imidazo[4,5-c]quinolin-2-one (25.00 g, 81.66 mmol) in DMF (375 mL). The mixture was heated to 80° C. for 3 h then allowed to cool to ambient temperature and stirred for 16 h. The precipitate was collected by filtration, washed with water (4×300 mL) and dried under vacuum at 50° C. to afford the desired material as a white solid (23.82 g, 91%). NMR Spectrum: $^1$H NMR (500 MHz, DMSO-d6) δ 1.63 (6H, d), 3.49 (3H, s), 5.15-5.23 (1H, m) 7.75 (1H, dd), 7.99 (1H, d), 8.44 (1H, d), 8.91 (1H, s). Mass Spectrum: m/z (ES+)[M+H]+=320.

Intermediate E3: 8-Bromo-1-isopropyl-3H-imidazo[4,5-c]quinolin-2-one

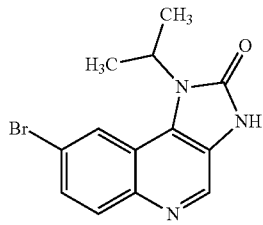 [SMILES: CC(C)n1c(=O)[nH]c2cnc3ccc(Br)cc3c21]

Triethylamine (45.3 mL, 332.06 mmol) was added to 6-bromo-4-(isopropylamino)quinoline-3-carboxylic acid (34.22 g, 110.69 mmol) in DMF (342 mL) at ambient temperature. After stirring at ambient temperature for 30 minutes, diphenyl phosphorazidate (26.2 mL, 121.76 mmol) was added and the resulting mixture stirred at 60° C. for 2 h. The reaction mixture was poured into water (1500 mL); the precipitate collected by filtration, washed with water (2×700 mL) and dried under vacuum at 50° C. to afford the desired material as a beige solid (29.6 g, 87%), which was used without further purification. NMR Spectrum: $^1$H NMR (500 MHz, CDCl$_3$) δ 1.64 (6H, d), 5.06-5.21 (1H, m), 7.75 (1H, d), 7.98 (1H, d), 8.43 (1H, s), 8.69 (1H, s), 11.57 (1H, s).
Mass Spectrum: m/z (ES+)[M+H]+=306.

Intermediate E4: 6-Bromo-4-(isopropylamino)quinoline-3-carboxylic acid

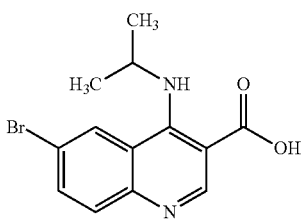 [SMILES: CC(C)Nc1c(C(=O)O)cnc2ccc(Br)cc12]

Ethyl 6-bromo-4-(isopropylamino)quinoline-3-carboxylate (38.0 g, 112.69 mmol) was suspended in methanol (800 mL) and water (200 mL). 10M sodium hydroxide solution (33.8 mL, 338.07 mmol) was added and the mixture stirred at ambient temperature for 1 h. THF (200 mL) was added and the resultant mixture stirred for 16 h. Water (400 mL) was added and the organics removed under reduced pressure. The resulting aqueous solution was acidified to pH 4-5 with 2M HCl and the precipitate collected by filtration, washed with water and dried under vacuum to afford the desired material as a white solid (34.7 g, 100%). NMR Spectrum: $^1$H NMR (500 MHz, DMSO-d6) δ 1.33 (6H, d), 4.39 (1H, s), 7.78 (1H, d), 7.92 (1H, dd), 8.38 (1H, d), 8.88 (1H, s). Mass Spectrum: m/z (ES+)[M+H]+=309.

Intermediate E5: Ethyl 6-bromo-4-(isopropylamino)quinoline-3-carboxylate

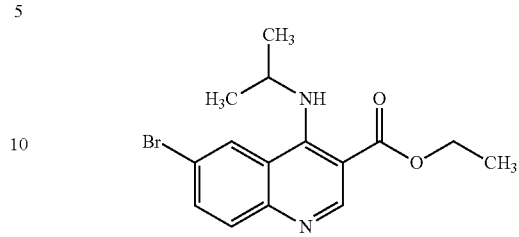

Propan-2-amine (11.00 ml, 128.02 mmol) was added to a suspension of ethyl 6-bromo-4-chloroquinoline-3-carboxylate (36.61 g, 116.38 mmol) and potassium carbonate (32.2 g, 232.77 mmol) in acetonitrile (250 mL) at 0° C. The mixture was stirred at 54° C. under reflux for 3 h. Further potassium carbonate (10.7 g, 77.6 mmol) and propan-2-amine (3.6 ml, 42.7 mmol) were added and stirring continued at 48° C. for a further 16 h. The solvents were removed in vacuo and the resulting residue partitioned between DCM (400 mL) and water (500 mL). The aqueous layer was re-extracted with DCM (2×200 mL); the combined organic layers were passed through a phase separating paper and concentrated under reduced pressure to afford the desired material as a beige solid (38.6 g, 98%). NMR Spectrum: $^1$H NMR (500 MHz, CDCl$_3$) δ 1.40 (6H, d), 1.43 (3H, t), 4.32-4.37 (1H, m), 4.40 (2H, q), 7.72 (1H, dd), 7.81 (1H, d), 8.29 (1H, d), 8.95 (1H, d), 9.10 (1H, s). Mass Spectrum: m/z (ES+)[M+H]+=337.

Intermediate E6: Ethyl 6-bromo-4-chloroquinoline-3-carboxylate

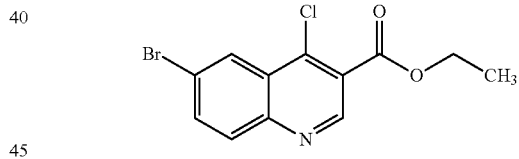

DMF (0.119 mL, 1.54 mmol) was added to ethyl 6-bromo-1-[(4-methoxyphenyl)methyl]-4-oxoquinoline-3-carboxylate (160 g, 384.37 mmol) in thionyl chloride (800 mL) at ambient temperature under air. The resulting mixture was stirred at 75° C. for 16 h then the solvent removed under reduced pressure. The resulting mixture was azeotroped twice with toluene then n-hexane (500 mL) added. The precipitate was collected by filtration, washed with n-hexane (200 mL) and dried under vacuum to afford the desired material (100 g, 83%) as a brown solid. NMR Spectrum: $^1$H NMR (400 MHz, CDCl$_3$) δ 1.47 (3H, t), 4.51 (2H, q), 7.95 (1H, dd), 8.11 (1H, d), 8.60 (1H, d), 9.24 (1H, s). Mass Spectrum: m/z (ES+)[M+H]+=314, 316.

On a larger scale, ethyl 6-bromo-1-[(4-methoxyphenyl)methyl]-4-oxoquinoline-3-carboxylate (5765 g, 13.85 mol) was charged to the vessel with thionyl chloride (28.8 L). An exotherm from 20-26° C. was observed. DMF (4.4 mL) was added with no observed exotherm and the batch heated to 75° C. and stirred for 17 h. HPLC showed 1.3% starting material remained with 98.0% product. The reaction was concentrated in vacuo and the residue azeotroped with toluene (25 L). The resulting solid was then slurried in heptane (18.5 L) for 2.5 h, filtered and washed with heptane (3×4 L). The solid was dried under vacuum at 35° C. to give 4077 g of the desired material (93% crude yield) which contained ~5% of ethyl 6-bromo-1-[(4-methoxyphenyl) methyl]-4-oxoquinoline-3-carboxylate in addition to ~4% hydrolysis product by HPLC (90% pure). The crude material (4077 g) was returned to the vessel and reprocessed with thionyl chloride (14.5 L) and DMF (2.2 mL). The mixture was heated to 75° C. for 40 h. The thionyl chloride was removed in vacuo and the residue azeotroped with toluene (10 L). The residue was slurried in heptane (18 L) for ~16 h at 20° C. The solid was collected by filtration, one portion being filtered under nitrogen and washed with heptane (3 L) to yield 2196 g of desired material (90% NMR assay, 99% by HPLC). The remainder of the batch was filtered under air and washed with heptane (3 L) to yield 1905 g of the desired material (88% NMR assay, 99% by HPLC). The yellow solids were combined for further processing (4101 g, 3653 g active, 83% yield, 99% by HPLC).

Intermediate E7: Ethyl 6-bromo-1-[(4-methoxyphenyl)methyl]-4-oxoquinoline-3-carboxylate

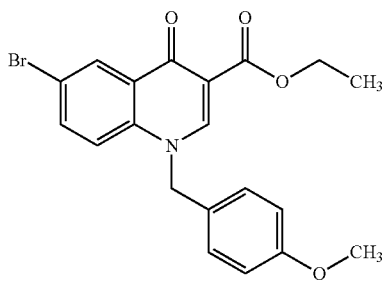 [SMILES: CCOC(=O)c1cn(Cc2ccc(OC)cc2)c2ccc(Br)cc2c1=O]

DBU (102 mL, 679.62 mmol) was added drop-wise to ethyl 2-(5-bromo-2-fluorobenzoyl)-3-[(4-methoxyphenyl) methylamino]prop-2-enoate (296.5 g 679.62 mmol), in acetone (1.2 L) at ambient temperature over a period of 2 minutes. The resulting solution was stirred for 16 h then the solid removed by filtration and washed with MTBE to afford the desired material (180 g, 64%) as light yellow solid. NMR Spectrum: $^1$H NMR (400 MHz, DMSO-d6) δ 1.30 (3H, t), 3.71 (3H, s), 4.25 (2H, q), 5.60 (2H, s), 6.90-6.95 (2H, m), 7.12-7.25 (2H, m), 7.67 (1H, d), 7.80-7.90 (1H, m), 8.30 (1H, d), 8.92 (1H, s). Mass Spectrum: m/z (ES+) [M+H]+=418.

On a larger scale, ethyl 2-(5-bromo-2-fluorobenzoyl)-3-[(4-methoxyphenyl)methylamino]prop-2-enoate (8434 g, (7730 g assumed active), 17.71 mol) was charged to the vessel with acetone (23.2 L) at 15° C. DBU (2.8 L, 18.72 mol) was added over 25 minutes with an observed exotherm from 18-23° C. over the addition. A precipitate formed after ~25 minutes and the batch continued to exotherm reaching a maximum of 37° C. after 1 h. The reaction was stirred at 20° C. for 16.5 h at which point HPLC indicated consumption of starting material and 96.5% product. The resulting precipitate was collected by filtration washing with TBME (4×3.4 L). The solid was then dried under vacuum at 40° C. to give 6033 g of the desired material as a white solid (81.6% yield over 3 steps, 99.8% purity by HPLC). Analytical data was consistent with that obtained on previous batches.

Intermediate E8: Ethyl 2-(5-bromo-2-fluorobenzoyl)-3-[(4-methoxyphenyl)methylamino]prop-2-enoate

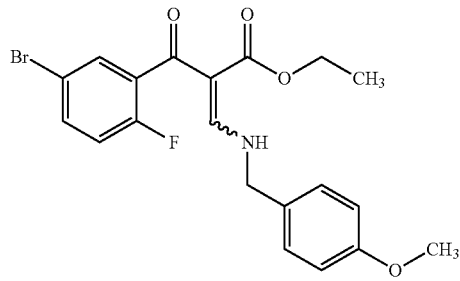 [SMILES: CCOC(=O)C(=CNCc1ccc(OC)cc1)C(=O)c1cc(Br)ccc1F]

(E)-Ethyl 3-(dimethylamino)acrylate (98 g, 685.00 mmol) was added portion-wise to 5-bromo-2-fluorobenzoyl chloride (163 g, 685 mmol) and DIPEA (120 mL, 685.00 mmol) in toluene (800 mL) at 10° C. over a period of 10 minutes. The resulting solution was stirred at 70° C. for 16 h then allowed to cool. (4-Methoxyphenyl)methanamine (94 g, 685 mmol) was added to the mixture over a period of 20 minutes at ambient temperature. The resulting solution was stirred for 3 h then the reaction mixture diluted with DCM (4 L), and washed with water (3×1 L). The organic phase was dried over Na$_2$SO$_4$, filtered and evaporated to give the desired material (300 g, 100%) as brown oil, which was used immediately in the subsequent reaction without further purification. Mass Spectrum: m/z (ES+)[M+H]+=436.

On a larger scale, 5-bromo-2-fluorobenzoyl chloride (4318 g, 4205 g active, 17.71 mol) was charged to the vessel as a solution in toluene (7.5 L). DIPEA (3150 mL, 18.08 mol) was added with no observed exotherm. Ethyl-3-(dimethylamino)acrylate (2532 g, 17.71 mol) was added portion-wise over 30 minutes maintaining a batch temperature <40° C. An exotherm from 21-24° C. was noted over the 30 minute addition with a further slow rise to 38° C. over 1 h. The reaction was stirred at 20-30° C. for 16.5 h. 4-Methoxybenzylamine (2439 g, 17.78 mol) was added portionwise over 30 mins maintaining a batch temperature <40° C. An exotherm of 25-30° C. was observed over the addition with cooling provided by a reduced jacket temperature of 15° C. The reaction was stirred for 4 h at 20-30° C. after which HPLC indicated 93.2% of desired material. The batch was split for workup with each half of the mixture diluted with DCM (28.6 L) and washed with water (3×7.8 L). The organics were dried over MgSO4 (~550 g) and filtered, washing with DCM (4 L). The combined organics were then concentrated to give 8444 g of the desired material as an oil (8434 g, 106% yield, 94.7% purity by HPLC). Analytical data was consistent with that obtained from previous batches.

Intermediate E9: 5-Bromo-2-fluorobenzoyl chloride

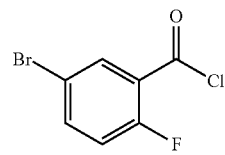 [SMILES: O=C(Cl)c1cc(Br)ccc1F]

Thionyl chloride (75.0 mL, 1027.36 mmol) was added drop-wise to 5-bromo-2-fluorobenzoic acid (150 g, 684.91 mmol), in toluene (1.2 L) and DMF (12 mL) at ambient temperature over a period of 1 h. The resulting mixture was stirred at 70° C. for 16 h then the mixture allowed to cool and concentrated in vacuo to afford the desired material (160 g, 98%) as light yellow oil, which was used without further purification. NMR Spectrum: $^1$H NMR (400 MHz, DMSO-d6) δ 7.26-7.31 (1H, m), 7.83 (1H, dd), 8.02 (1H, d).

On a larger scale, 3-bromo-6-fluorobenzoic acid (3888 g, 17.75 mol) was charged to the vessel at 20° C. followed by toluene (29.2 L). Thionyl chloride (1950 ml, 26.88 mol) was added, followed by DMF (310 mL) with no observed exotherm. The mixture was heated to 65-75° C. (solution obtained above ~45° C.) with no observed exotherm and slight gas evolution. The reaction was stirred for 40 h at this temperature at which point HPLC analysis showed 87.6% product, 3.4% starting material. The reaction was concentrated in vacuo and azeotroped with toluene (18 L) to give 4328 g of the desired material (103% yield, 87.3% by HPLC).

Example 8

8-[6-[3-(Azetidin-1-yl)propoxy]-3-pyridyl]-1-isopropyl-3-methyl-imidazo[4,5-c]quinolin-2-one

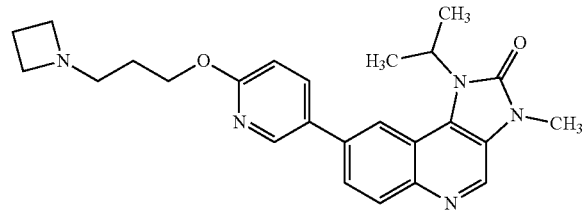 [SMILES: CC(C)n1c(=O)n(C)c2cnc3ccc(-c4ccc(OCCCN5CCC5)nc4)cc3c21]

Chloro(2-dicyclohexylphosphino-2',4',6'-triisopropyl-1,1'-biphenyl)[2-(2'-amino-1,1'-biphenyl)]palladium(II) (24.55 mg, 0.03 mmol) was added to 8-bromo-1-isopropyl-3-methyl-imidazo[4,5-c]quinolin-2-one (100 mg, 0.31 mmol), 2-(3-(azetidin-1-yl)propoxy)-5-(4,4,5,5-tetramethyl-1,3,2-dioxaborolan-2-yl)pyridine (149 mg, 0.47 mmol) and cesium carbonate (204 mg, 0.62 mmol) in 1,4-dioxane (4 mL), water (1 mL) at r.t. under an inert atmosphere. The resulting mixture was stirred at 100° C. for 2 h then allowed to cool and the solvent removed under reduced pressure. The crude product was purified by preparative HPLC (XSelect CSH Prep C18 OBD column, 5μ silica, 19 mm diameter, 150 mm length), using decreasingly polar mixtures of water (containing 0.1% Formic acid) and MeCN as eluents, to afford the desired material as a white solid (30.0 mg, 21%). NMR Spectrum: $^1$H NMR (400 MHz, DMSO-d6) δ 1.72 (8H, dd), 1.97 (2H, p), 2.50 (2H, s), 3.14 (4H, dd), 3.51 (3H, s), 4.34 (2H, t), 5.36 (1H, p), 6.97 (1H, d), 7.94 (1H, dd), 8.10-8.23 (2H, m), 8.40 (1H, d), 8.66 (1H, d), 8.89 (1H, s). Mass Spectrum: m/z (ES+)[M+H]+=432.

Intermediate F1: 2-[3-(Azetidin-1-yl)propoxy]-5-(4,4,5,5-tetramethyl-1,3,2-dioxaborolan-2-yl)pyridine

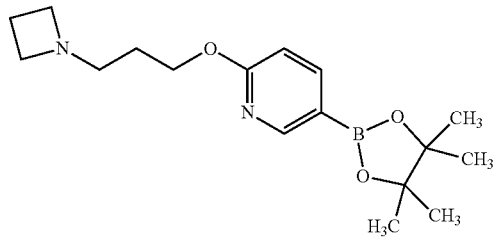 [SMILES: CC1(C)OB(c2ccc(OCCCN3CCC3)nc2)OC1(C)C]

n-Butyl lithium (4.65 mL, 11.62 mmol) was added to 2-[3-(azetidin-1-yl)propoxy]-5-bromopyridine (2.1 g, 7.74 mmol) and 2-isopropoxy-4,4,5,5-tetramethyl-1,3,2-dioxaborolane (2.161 g, 11.62 mmol) in THF (50 mL) at −78° C. over a period of 10 minutes and the resulting solution stirred at −78° C. for 1 h. The reaction was quenched with sat. aqueous solution of sodium hydrogen carbonate (10 mL) and the solvent removed in vacuo. The residue was dissolved in DCM (100 mL), dried over Na$_2$SO$_4$, filtered and evaporated to afford the desired material (2.00 g, 81%) as a white solid.
Mass Spectrum: m/z (ES+)[M+H]+=319

Intermediate F2: 2-[3-(Azetidin-1-yl)propoxy]-5-bromopyridine

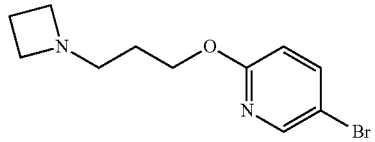 [SMILES: Brc1ccc(OCCCN2CCC2)nc1]

Sodium hydride (1.364 g, 56.82 mmol) was added to 3-(azetidin-1-yl)propan-1-ol (2.62 g, 22.73 mmol) in THF (20 mL) at ambient temperature under an inert atmosphere and the reaction stirred for 10 minutes. 5-Bromo-2-fluoropyridine (2.0 g, 11.36 mmol) was added and the resulting solution stirred for 1 h before being quenched with water (20 mL) and extracted with EtOAc (5×50 mL). The organics were combined, dried over Na$_2$SO$_4$, filtered and concentrated in vacuo to afford the desired material (3.75 g, 122%) as a white solid. NMR Spectrum: $^1$H NMR (300 MHz, CDCl$_3$) δ 1.80 (2H, m), 2.11 (2H, m), 2.55 (2H, t), 3.18 (4H, t), 4.328 (2H, t), 6.64 (1H, d), 7.62 (H, dd), 8.16 (1H, d).
Mass Spectrum: m/z (ES+)[M+H]+=271.

Example 9

8-[2-Fluoro-6-[3-(1-piperidyl)propoxy]-3-pyridyl]-1-isopropyl-3-methyl-imidazo[4,5-c]quinolin-2-one

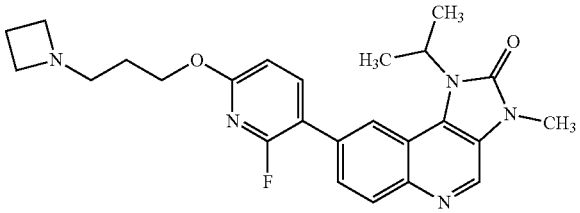 [SMILES: CC(C)n1c(=O)n(C)c2cnc3ccc(-c4ccc(OCCCN5CCC5)nc4F)cc3c21]

Chloro(2-dicyclohexylphosphino-2',4',6'-triisopropyl-1,1'-biphenyl)[2-(2'-amino-1,1'-biphenyl)]palladium(II) (45.6 mg, 0.06 mmol) was added to 2-fluoro-6-[3-(1-piperidyl)propoxy]-3-(4,4,5,5-tetramethyl-1,3,2-dioxaborolan-2-yl)pyridine (crude reaction mixture assumed to contain 232 mg, 0.64 mmol), 8-bromo-1-isopropyl-3-methyl-imidazo[4,5-c]quinolin-2-one (186 mg, 0.58 mmol) and cesium carbonate (567 mg, 1.74 mmol) in 1,4-dioxane (5 mL) and water (2.5 mL). The resulting mixture was stirred at 80° C. for three h then allowed to cool. The reaction mixture was diluted with ethyl acetate (50 mL), washed twice with water (25 mL), the organic layer dried over MgSO$_4$, filtered and evaporated to afford crude product. The crude product was purified by flash silica chromatography, elution gradient 0 to 4% 2N methanolic ammonia in DCM, to afford the desired material as an off-white solid (168 mg, 61%). NMR Spectrum: $^1$H NMR (500 MHz, DMSO-d6) δ 1.37 (2H, d), 1.48 (4H, p), 1.64 (6H, d), 1.88 (2H, p), 2.22-2.44 (6H, m), 3.49 (3H, s), 4.30 (2H, t), 5.26 (1H, h), 6.93 (1H, dd), 7.80 (1H, dd), 8.12 (1H, d), 8.21 (1H, dd), 8.42 (1H, s), 8.89 (1H, s). Mass Spectrum: m/z (ES+)[M+H]+=478.

The above material can also be isolated as the methane sulfonic acid salt by taking the material as prepared above and subjecting to the following reaction conditions. 8-[2-Fluoro-6-[3-(1-piperidyl)propoxy]-3-pyridyl]-1-isopropyl-3-methyl-imidazo[4,5-c]quinolin-2-one (162 mg, 0.34 mmol) was dissolved in DCM (4 mL) and treated with 1M methanesulfonic acid (0.35 mL, 0.36 mmol) in DCM then the mixture evaporated to dryness. The residue was triturated with diethyl ether to afford the methane sulfonic acid salt as a white solid (184 mg). NMR Spectrum: $^1$H NMR (500 MHz, DMSO-d6) δ 1.22-1.98 (12H, m), 2.06-2.24 (2H, m), 2.31 (3H, s), 2.90 (2H, s), 3.19 (2H, s), 3.50 (5H, s), 4.37 (2H, t), 5.25 (1H, p), 6.96 (1H, d), 7.80 (1H, d), 8.13 (1H, d), 8.26 (H, dd), 8.42 (1H, s), 8.90 (1H, s). Mass Spectrum: m/z (ES+)[M+H]+=478.

The following compounds were prepared in an analogous fashion from either 8-bromo-1-isopropyl-3-methyl-imidazo[4,5-c]quinolin-2-one or 8-bromo-7-fluoro-1-isopropyl-3-methyl-imidazo[4,5-c]quinolin-2-one and the appropriate boronic ester.

| Example | Structure | Name |
| --- | --- | --- |
| 10* | 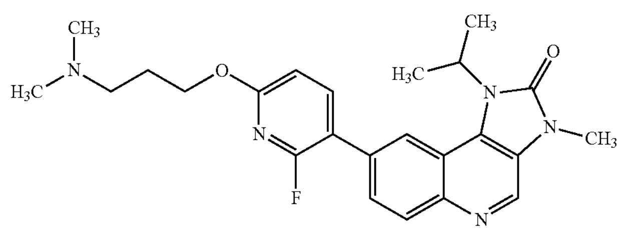 | 8-[6-[3-(dimethylamino)propoxy]-2-fluoro-3-pyridyl]-1-isopropyl-3-methyl-imidazo[4,5-c]quinolin-2-one |
| 11* | 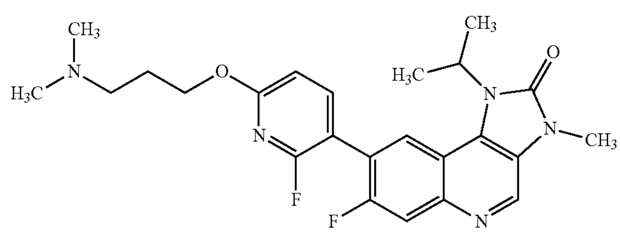 | 8-[6-[3-(dimethylamino)propoxy]-2-fluoro-3-pyridyl]-7-fluoro-1-isopropyl-3-methyl-imidazo[4,5-c]quinolin-2-one |
| 12** | 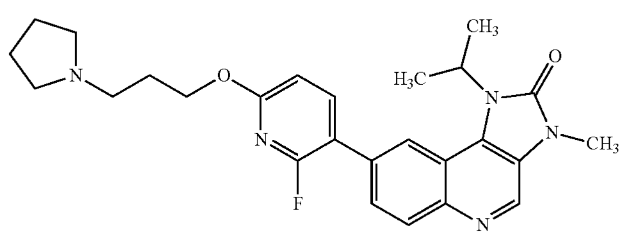 [SMILES: CC(C)n1c(=O)n(C)c2cnc3ccc(-c4ccc(OCCCN5CCCC5)nc4F)cc3c21] | 8-[2-fluoro-6-(3-pyrrolidin-1-ylpropoxy)-3-pyridyl]-1-isopropyl-3-methyl-imidazo[4,5-c]quinolin-2-one |
| 13** | 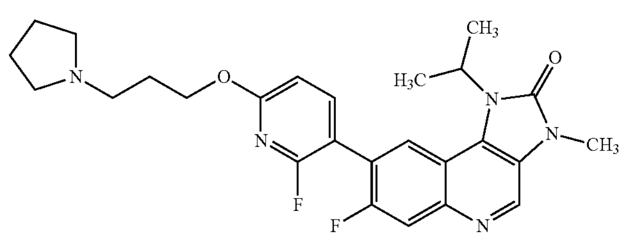 [SMILES: CC(C)n1c(=O)n(C)c2cnc3cc(F)c(-c4ccc(OCCCN5CCCC5)nc4F)cc3c21] | 7-fluoro-8-[2-fluoro-6-(3-pyrrolidin-1-ylpropoxy)-3-pyridyl]-1-isopropyl-3-methyl-imidazo[4,5-c]quinolin-2-one |

| Example | Structure | Name |
|---|---|---|
| 14*** | 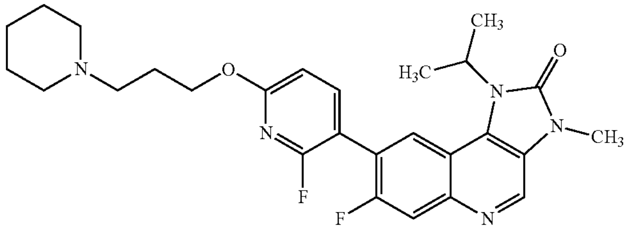 [SMILES: CC(C)n1c(=O)n(C)c2cnc3cc(F)c(-c4ccc(OCCCN5CCCCC5)nc4F)cc3c21] | 7-fluoro-8-[2-fluoro-6-[3-(1-piperidyl)propoxy]-3-pyridyl]-1-isopropyl-3-methyl-imidazo[4,5-c]quinolin-2-one |
| 15*** | 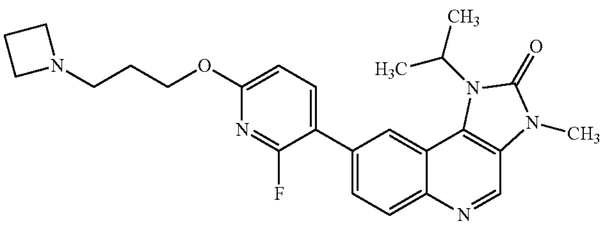 [SMILES: CC(C)n1c(=O)n(C)c2cnc3ccc(-c4ccc(OCCCN5CCC5)nc4F)cc3c21] | 8-[6-[3-(azetidin-1-yl)propoxy]-2-fluoro-3-pyridyl]-1-isopropyl-3-methyl-imidazo[4,5-c]quinolin-2-one |
| 16**** | 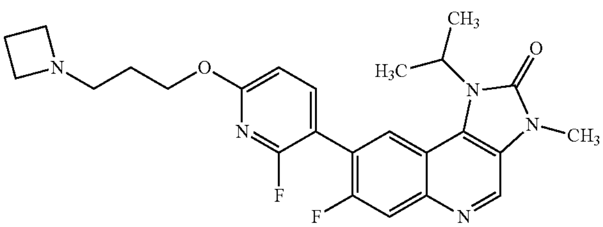 [SMILES: CC(C)n1c(=O)n(C)c2cnc3cc(F)c(-c4ccc(OCCCN5CCC5)nc4F)cc3c21] | 8-[6-[3-(azetidin-1-yl)propoxy]-2-fluoro-3-pyridyl]-7-fluoro-1-isopropyl-3-methyl-imidazo[4,5-c]quinolin-2-one |

*The reaction was stirred at 80° C. for 5 h and purified by flash column chromatography and/or preparative HPLC.
**The reaction was stirred at 80° C. for 5 h in a 5:1 mixture of dioxane/water, and purified by flash column chromatography followed by preparative HPLC.
***The reaction was stirred at 80° C. for 2 h in a 4:1 mixture of dioxane/water,
****The reaction was stirred at 80° C. for 4 h Example 10

NMR Spectrum: $^1$H NMR (400 MHz, MeOH-d4) δ 1.77 (6H, d), 1.98-2.10 (2H, m), 2.34 (6H, s), 2.54-2.63 (2H, m), 3.61 (3H, s), 4.41 (2H, t), 5.36 (1H, p), 6.88 (1H, dd), 7.87 (1H, dt), 8.08-8.21 (2H, m), 8.53 (1H, s), 8.83 (1H, s). Mass Spectrum: m/z (ES+)[M+H]+=438.

Example 11

NMR Spectrum: $^1$H NMR (400 MHz, MeOH-d4) δ 1.74 (6H, d), 2.04 (2H, ddt), 2.34 (6H, s), 2.54-2.63 (2H, m), 3.60 (3H, s), 4.42 (2H, t), 5.30 (1H, p), 6.88 (1H, dd), 7.84 (1H, d), 8.03 (1H, ddd), 8.42 (1H, d), 8.85 (1H, s). Mass Spectrum: m/z (ES+)[M+H]+=456.

Example 12

NMR Spectrum: $^1$H NMR (300 MHz, MeOH-d4) δ 1.76 (6H, d), 2.12-2.30 (4H, m), 2.31-2.35 (2H, m), 2.38-3.47 (6H, m), 3.62 (3H, s), 4.50 (2H, t), 5.32-5.41 (1H, m), 6.92-6.95 (1H, m), 7.89 (1H, d), 8.15-8.20 (2H, m), 8.41 (1H, s), 8.85 (1H, s). Mass Spectrum: m/z (ES+)[M+H]+=464.

Example 13

NMR Spectrum: $^1$H NMR (400 MHz, MeOH-d4) δ 1.74 (6H, d), 2.08-2.20 (4H, m), 2.24-2.36 (2H, m), 3.39-3.48 (6H, m), 3.61 (3H, s), 4.51 (2H, t), 5.30 (1H, t), 6.93 (1H, d), 7.86 (1H, d), 8.08 (1H, t), 8.42 (0H, d), 8.87 (1H, s). Mass Spectrum: m/z (ES+)[M+H]+=482.

Example 14

NMR Spectrum: $^1$H NMR (300 MHz, DMSO-d6) δ 1.39 (2H, d), 1.51 (5H, p), 1.60 (6H, d), 1.93 (2H, q), 2.43 (6H, d), 3.49 (3H, s), 4.32 (2H, t), 5.24 (1H, q), 6.96 (1H, dd), 7.92 (1H, d), 8.07-8.22 (2H, m), 8.38 (1H, d), 8.93 (1H, s). Mass Spectrum: m/z (ES+)[M+H]+=496.

Example 15

NMR Spectrum: $^1$H NMR (400 MHz, MeOH-d4) δ 1.64 (6H, d), 1.73 (2H, t), 1.96 (2H, p), 2.46-2.51 (2H, t), 3.12 (4H, t), 3.50 (3H, s), 4.28 (2H, t), 5.28 (1H, q), 6.94 (1H, dd), 7.76-7.86 (1H, m), 8.08-8.29 (2H, m), 8.43 (1H, s), 8.90 (1H, s). Mass Spectrum: m/z (ES+)[M+H]+=450

Example 16

NMR Spectrum: $^1$H NMR (300 MHz, DMSO-d6) δ 1.60 (6H, d), 1.70-1.81 (2H, m), 1.96-2.04 (2H, m), 2.55 (2H, s), 3.19 (4H, dt), 3.49 (3H, s), 4.30 (2H, t), 5.22 (1H, q), 6.95 (1H, dd), 7.92 (1H, d), 8.08-8.17 (1H, m), 8.38 (1H, d), 8.93 (1H, s). Mass Spectrum: m/z (ES+)[M+H]+=468.

Intermediate G1: 3-[[6-Fluoro-5-(4,4,5,5-tetramethyl-1,3,2-dioxaborolan-2-yl)-2-pyridyl]oxy]-N,N-dimethyl-propan-1-amine

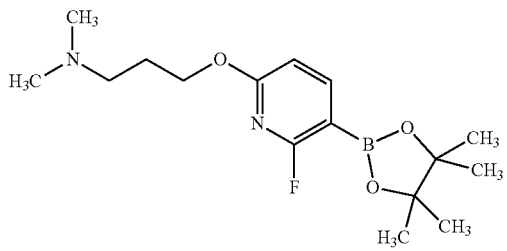

A solution of n-butyllithium (0.693 g, 10.83 mmol) in n-hexane (4.33 mL) was added to a stirred mixture of 3-(5-bromo-6-fluoropyridin-2-yl)oxy-N,N-dimethylpropan-1-amine (2 g, 7.22 mmol) and 2-isopropoxy-4,4,5,5-tetramethyl-1,3,2-dioxaborolane (2.014 g, 10.83 mmol) in THF (20 mL) at −78° C. over a period of 20 minutes under an inert atmosphere. The resulting mixture was allowed to warm to ambient temperature and stirred for 2 h. The reaction mixture was quenched with sat. NaHCO3 solution and concentrated in vacuo. The crude product was purified by FCC, elution gradient 0 to 10% MeOH in DCM, to afford the desired material (2.50 g, 107%). Mass Spectrum: m/z (ES+)[M+H]+=325.

Intermediate G2: 3-(5-Bromo-6-fluoropyridin-2-yl)oxy-N,N-dimethylpropan-1-amine

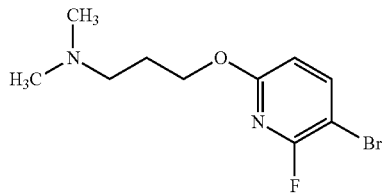

(E)-Diisopropyl diazene-1,2-dicarboxylate (15.80 g, 78.13 mmol) was added dropwise to 3-(dimethylamino)propan-1-ol (8.06 g, 78.13 mmol), 5-bromo-6-fluoropyridin-2-ol (10 g, 52.09 mmol) and triphenylphosphine (20.49 g, 78.13 mmol) in DCM (150 mL) cooled to 0-5° C. under an inert atmosphere. The resulting solution was stirred at ambient temperature for 16 h then the solvent removed under reduced pressure. The residue was diluted with EtOAc (50 mL) and the solid removed by filtration and discarded. The filtrate was acidified with hydrogen chloride in dioxane. The solid was collected by filtration then dissolved in a sat. aqueous solution of Na2CO3 (200 mL) and extracted with EtOAc (3×100 mL). The combined organic layers were washed with water, brine, dried over Na2SO4 and concentrated in vacuo to afford the desired material (9.00 g, 62.3%). NMR Spectrum: $^1$H NMR (300 MHz, CDCl$_3$) δ 1.89-1.98 (2H, m), 2.26 (6H, s), 2.34 (2H, t), 4.30 (2H, t), 6.53 (1H, d), 7.74 (1H, t). Mass Spectrum: m/z (ES+)[M+H]+=277.

Intermediate G3: 5-Bromo-6-fluoropyridin-2-ol

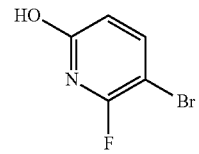

A solution of sodium nitrite (21.67 g, 314.13 mmol) in water (150 mL) was added dropwise to a stirred mixture of 5-bromo-6-fluoropyridin-2-amine (50 g, 261.78 mmol) and sulphuric acid (1.2 mL, 22.51 mmol) in water (750 mL) at 0-5° C. The resulting suspension was stirred for 48 h at ambient temperature then the precipitate collected by filtration, washed with water (200 mL) and dried under vacuum to afford the desired material (40.0 g, 80%) as a pale yellow solid, which was used without further purification. NMR Spectrum: $^1$H NMR (300 MHz, DMSO-d6) δ 6.55 (1H, d), 8.00 (1H, t), 11.71 (1H, bs). Mass Spectrum: m/z (ES+)[M+H]+=192.

Intermediate G4: 5-Bromo-6-fluoropyridin-2-amine

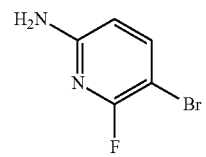

NBS (50.0 g, 280.99 mmol) was added slowly to 6-fluoropyridin-2-amine (30 g, 267.61 mmol) in MeCN (300 mL) cooled to 10-20° C. over a period of 30 minutes. The resulting solution was stirred at ambient temperature for 60 minutes then the solvent removed under reduced pressure. The residue was diluted with water, the precipitate collected by filtration, washed with water (200 mL) and dried under vacuum to afford the desired material (50.0 g, 98%) as a white solid, which was used without further purification. NMR Spectrum: $^1$H NMR (300 MHz, DMSO-d6) δ 6.29 (1H, d), 6.57 (2H, bs), 7.65 (1H, t). Mass Spectrum: m/z (ES+)[M+H]+=191.

Intermediate H1: 2-Fluoro-6-[3-(1-piperidyl)propoxy]-3-(4,4,5,5-tetramethyl-1,3,2-dioxaborolan-2-yl)pyridine

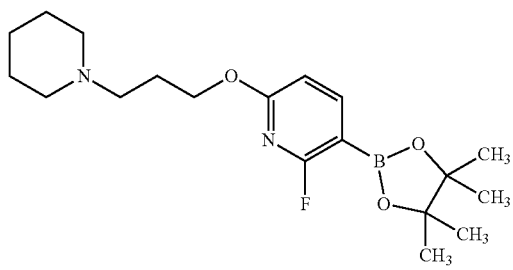 [SMILES: CC1(C)OB(c2ccc(OCCCN3CCCCC3)nc2F)OC1(C)C]

PdCl$_2$(dppf) (0.692 g, 0.95 mmol) was added to 3-bromo-2-fluoro-6-(3-(piperidin-1-yl)propoxy)pyridine (3 g, 9.46 mmol), 4,4,4',4',5,5,5',5'-octamethyl-2,2'-bi(1,3,2-dioxaborolane) (3.60 g, 14.19 mmol) and potassium acetate (1.856 g, 18.92 mmol) in 1,4-dioxane (60 mL) at ambient temperature under an inert atmosphere. The resulting mixture was stirred at 80° C. for 16 h then cooled and the solvent removed under reduced pressure. The crude product was purified by flash silica chromatography, elution gradient 0 to 100% EtOAc in petroleum ether, to afford the desired material as a red liquid (0.90 g, 26%) which was used without further purification. Mass Spectrum: m/z (ES+)[M+H]+=365.

The following boronic ester intermediates were prepared in an analogous fashion from the appropriate bromides.

| Intermediate | Structure | Name |
|---|---|---|
| I1* | 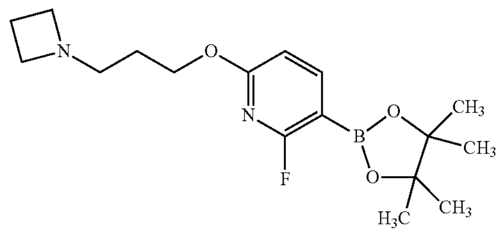 [SMILES: CC1(C)OB(c2ccc(OCCCN3CCC3)nc2F)OC1(C)C] | 6-[3-(azetidin-1-yl)propoxy]-2-fluoro-3-(4,4,5,5-tetramethyl-1,3,2-dioxaborolan-2-yl)pyridine |
| J1** | 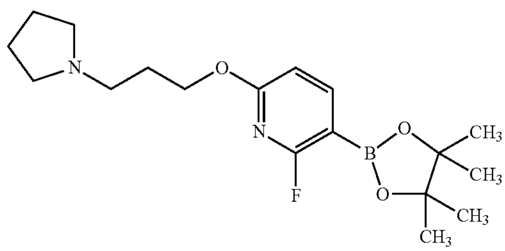 [SMILES: CC1(C)OB(c2ccc(OCCCN3CCCC3)nc2F)OC1(C)C] | 2-fluoro-6-(3-pyrrolidin-1-ylpropoxy)-3-(4,4,5,5-tetramethyl-1,3,2-dioxaborolan-2-yl)pyridine |

*The material was used without purification
**The reaction was stirred at 100° C. for 16 h and the material used without purification.

Intermediate I1: Mass Spectrum: m/z (ES+)[M+H]+=337.
Intermediate J1: Mass Spectrum: m/z (ES+)[M+H]+=351.

Intermediate H2: 3-Bromo-2-fluoro-6-[3-(1-piperidyl)propoxy]pyridine

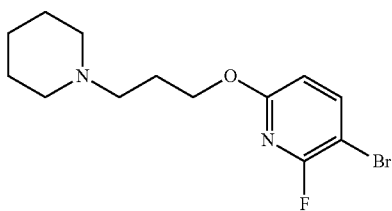 [SMILES: Fc1nc(OCCCN2CCCCC2)ccc1Br]

(E)-Di-tert-butyl diazene-1,2-dicarboxylate (7.20 g, 31.25 mmol) was added to 3-(piperidin-1-yl)propan-1-ol (4.48 g, 31.25 mmol), triphenylphosphine (8.20 g, 31.25 mmol) and 5-bromo6-fluoropyridin-2-ol (4.0 g, 20.83 mmol) in DCM (50 mL). The resulting mixture was stirred at ambient temperature for 18 h then the solvent removed under reduced pressure. The residue was triturated with EtOAc (100 mL) and filtered to remove solid. To the filtrate was added 20 mL HCl(gas) solution in dioxane. The solid was collected by filtration. The solid was dissolved in water (100 mL), basified with a saturated aqueous solution of $Na_2CO_3$ and extracted with EtOAc (200 mL). The organic layer was separated and washed with saturated brine (50 mL), dried over $Na_2SO_4$, filtered and evaporated to afford the desired material as a yellow oil (1.50 g, 22.70%) which was used without further purification. NMR Spectrum: $^1$H NMR (300 MHz, DMSO-d6) δ 1.46-1.51 (6H, m), 1.82-1.89 (2H, m), 2.30-2.51 (6H, m), 4.21 (2H, t), 6.74 (1H, d), 8.07 (1H, t). Mass Spectrum: m/z (ES+)[M+H]+=317.

The following bromides were made in an analogous fashion from 5-bromo-6-fluoropyridin-2-ol and the appropriate alcohol.

| Intermediate | Structure | Name |
|---|---|---|
| I2* | 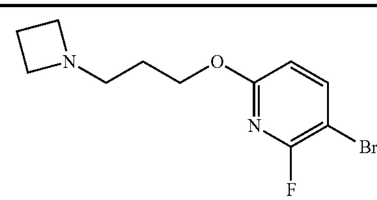 | 6-[3-(azetidin-1-yl)propoxy]-3-bromo-2-fluoro-pyridine |
| J2** | 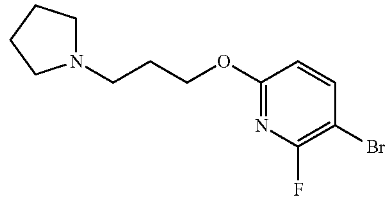 [SMILES: Fc1nc(OCCCN2CCCC2)ccc1Br] | 3-bromo-2-fluoro-6-(3-pyrrolidin-1-ylpropoxy)pyridine |

Intermediate I2: NMR Spectrum: ¹H NMR (300 MHz, CDCl₃) δ 1.63-1.92 (2H, m), 2.08 (2H, p), 2.53 (2H, t), 3.20 (4H, t), 4.27 (2H, t), 6.53 (1H, dd), 7.61-7.81 (1H, m); Mass Spectrum: m/z (ES+)[M+H]+=291

Intermediate J2: Mass Spectrum: m/z (ES+) [M+H]+=303.

Example 17

8-[6-[3-(Dimethylamino)propoxy]-3-pyidyl]-7-fluoro-1-isopropyl-3H-imidazo[4,5-c]quinolin-2-one

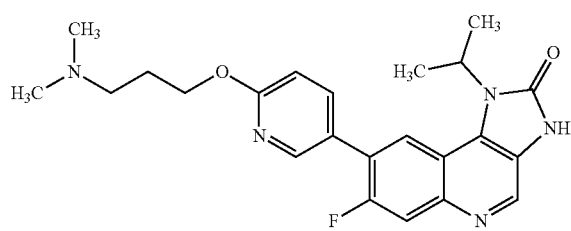 [SMILES: CC(C)n1c(=O)[nH]c2cnc3cc(F)c(-c4ccc(OCCCN(C)C)nc4)cc3c21]

Chloro(2-dicyclohexylphosphino-2',4',6'-triisopropyl-1,1'-biphenyl)[2-(2'-amino-1,1'-biphenyl)]palladium(II) (149 mg, 0.19 mmol) was added to N,N-dimethyl-3-[5-(4,4,5,5-tetramethyl-1,3,2-dioxaborolan-2-yl)pyridin-2-yl]oxypropan-1-amine (680 mg, 2.22 mmol), 8-bromo-7-fluoro-1-isopropyl-3H-imidazo[4,5-c]quinolin-2-one (600 mg, 1.85 mmol) and Cs₂CO₃ (1508 mg, 4.63 mmol) in 1,4-dioxane (5 mL) and water (0.5 mL). The resulting mixture was stirred at 80° C. for 5 h. The crude product was purified by flash silica chromatography, elution gradient 10 to 20% MeOH in DCM, the pure fractions combined and evaporated to dryness. The product was further purified by flash C18-flash chromatography, elution gradient 5 to 40% MeCN in water, to afford the desired material as a yellow solid (260 mg, 33.2%). NMR Spectrum: ¹H NMR (300 MHz, CDCl₃) δ 0.72 (6H, d), 2.00-2.15 (2H, m), 2.37 (6H, s), 2.61-2.66 (2H, m), 4.42 (2H, t), 5.27-5.31 (1H, m), 6.94 (1H, d), 7.79 (1H, d), 8.02 (1H, d), 8.32 (1H, d), 8.43 (1H, s), 8.65 (1H, s). Mass Spectrum: m/z (ES+)[M+H]+=424.

The following compound was prepared in an analogous fashion from 8-bromo-7-fluoro-1-isopropyl-3H-imidazo[4,5-c]quinolin-2-one and 2-[3-(1-piperidyl)propoxy]-5-(4,4,5,5-tetramethyl-1,3,2-dioxaborolan-2-yl)pyridine.

Metabolite A

7-Fluoro-1-isopropyl-3-methyl-8-[6-[3-(1-oxidopiperidin-1-ium-1-yl)propoxy]-3-pyridyl]imidazo[4,5-c]quinolin-2-one

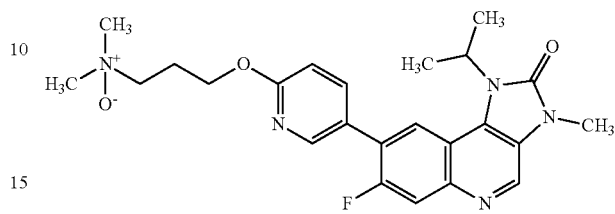

The pH of a solution of potassium phosphate, dibasic (1.74 g, 9.99 mmol) in water (100 mL) was adjusted to pH9 by the addition of 2M hydrochloric acid. A portion of this prepared solution (23 mL) was then added to a vessel containing 7-fluoro-1-isopropyl-3-methyl-8-[6-[3-(1-piperidyl)propoxy]-3-pyridyl]imidazo[4,5-c]quinolin-2-one (0.27 g, 0.565 mmol). Propan-2-ol (3.9 mL) was added to the reaction vessel followed by the addition of BVMPO-P1-D08 (0.27 g, 0.000540 mmol), KRED-P1-H10 (54 mg, 0.0011 mmol) and beta-nicotinamide adenine dinucleotide phosphate disodium salt (27 mg, 0.034291 mmol). The reaction was heated to 32° C. overnight with vigorous stirring (300 rpm) and compressed air blown continuously into the vessel headspace. Further propan-2-ol (3.9 mL) and water (~10 mL) was added. The reaction mixture was stirred at 30° C. with stirring (300 rpm) for a further 3 days then diluted with acetonitrile (40.5 mL), filtered and the filtrate evaporated under reduced pressure until the remaining volume was ~25 mL. Sodium chloride (~2 g) was added and the mixture extracted with butan-1-ol (2×24.3 mL). The extracts were combined, dried over Na₂SO₄, and concentrated to give a brown solid. The crude material was purified by silica chromatography, eluting with a mixture of DCM/MeOH/cNH₃ (125:10:1), to afford the desired material as an off white solid (0.040 g, 14%). NMR Spectrum: ¹H NMR (500 MHz, DMSO-d6) δ 1.2-1.31 (1H, m), 1.44 (2H, d), 1.56 (1H, d), 1.63 (6H, d), 2.04-2.17 (2H, m), 2.25-2.33 (2H, m), 2.91 (2H, d), 3.10 (2H, td), 3.19-3.26 (2H m), 3.49 (3H, s), 4.44 (2H, t), 5.27 (1H, p), 6.98 (1H, dd), 7.91 (1H, d), 8.05

| Example | Structure | Name |
|---|---|---|
| 18 | ![structure] | 7-Fluoro-1-isopropyl-8-[6-[3-(1-piperidyl)propoxy]-3-pyridyl]-3H-imidazo[4,5-c]quinolin-2-one |

The preparation of 8-bromo-7-fluoro-1-isopropyl-3H-imidazo[4,5-c]quinolin-2-one, N,N-dimethyl-3-[5-(4,4,5,5-tetramethyl-1,3,2-dioxaborolan-2-yl)pyridin-2-yl]oxypropan-1-amine and 2-[3-(1-piperidyl)propoxy]-5-(4,4,5,5-tetramethyl-1,3,2-dioxaborolan-2-yl)pyridine have been described previously.

(1H, dt), 8.31 (1H, d), 8.50 (1H, s), 8.90 (1H, s). Mass Spectrum: m/z (ES+)[M+H]+=494.

BIOLOGICAL ASSAYS

The following assays were used to measure the effects of the compounds of the present invention: a) ATM cellular potency assay; b) PI3K cellular potency assay; c) mTOR cellular potency assay; d) ATR cellular potency assay. During the description of the assays, generally:

i. The following abbreviations have been used: 4NQO=4-Nitroquinoline N-oxide; Ab=Antibody; BSA=Bovine Serum Albumin; $CO_2$=Carbon Dioxide; DMEM=Dulbecco's Modified Eagle Medium; DMSO=Dimethyl Sulphoxide; EDTA=Ethylenediaminetetraacetic Acid; EGTA=Ethylene Glycol Tetraacetic Acid; ELISA=Enzyme-linked Immunosorbent Assay; EMEM=Eagle's Minimal Essential Medium; FBS=Foetal Bovine Serum; h=Hour(s); HRP=Horseradish Peroxidase; i.p.=intraperitoneal; PBS=Phosphate buffered saline; PBST=Phosphate buffered saline/Tween; TRIS=Tris(Hydroxymethyl) aminomethane; MTS reagent: [3-(4,5-dimethylthiazol-2-yl)-5-(3-carboxymethoxyphenyl)-2-(4-sulfophenyl)-2H-tetrazolium, inner salt, and an electron coupling reagent (phenazine methosulfate) PMS; s.c.=sub-cutaneously.

ii. $IC_{50}$ values were calculated using a smart fitting model in Genedata. The $IC_{50}$ value was the concentration of test compound that inhibited 50% of biological activity.

Assay a): ATM Cellular Potency
Rationale:

Cellular irradiation induces DNA double strand breaks and rapid intermolecular autophosphorylation of serine 1981 that causes dimer dissociation and initiates cellular ATM kinase activity. Most ATM molecules in the cell are rapidly phosphorylated on this site after doses of radiation as low as 0.5 Gy, and binding of a phosphospecific antibody is detectable after the introduction of only a few DNA double-strand breaks in the cell.

The rationale of the pATM assay is to identify inhibitors of ATM in cells. HT29 cells are incubated with test compounds for 1 hr prior to X-ray-irradiation. 1 h later the cells are fixed and stained for pATM (Ser1981). The fluorescence is read on the arrayscan imaging platform.

Method Details:

HT29 cells (ECACC #85061109) were seeded into 384 well assay plates (Costar #3712) at a density of 3500 cells/well in 40 µl EMEM medium containing 1% L glutamine and 10% FBS and allowed to adhere overnight. The following morning compounds of Formula (I) in 100% DMSO were added to assay plates by acoustic dispensing. After 1 h incubation at 37° C. and 5% $CO_2$, plates (up to 6 at a time) were irradiated using the X-RAD 320 instrument (PXi) with equivalent to ~600 cGy. Plates were returned to the incubator for a further 1 h. Then cells were fixed by adding 20 µl of 3.7% formaldehyde in PBS solution and incubating for 20 minutes at r.t. before being washed with 50 µl/well PBS, using a Biotek EL405 plate washer. Then 20 µl of 0.1% Triton X100 in PBS was added and incubated for 20 minutes at r.t., to permeabalise cells. Then the plates were washed once with 50 µl/well PBS, using a Biotek EL405 plate washer.

Phospho-ATM Ser1981 antibody (Millipore #MAB3806) was diluted 10000 fold in PBS containing 0.05% polysorbate/Tween and 3% BSA and 20 µl was added to each well and incubated over night at r.t. The next morning plates were washed three times with 50 µl/well PBS, using a Biotek EL405 plate washer, and then 20 µl of secondary Ab solution, containing 500 fold diluted Alexa Fluor® 488 Goat anti-rabbit IgG (Life Technologies, A11001) and 0.002 mg/ml Hoeschst dye (Life technologies #H-3570), in PBS containing 0.05% polysorbate/Tween and 3% BSA, was added. After 1 h incubation at r.t., the plates were washed three times with 50 µl/well PBS, using a Biotek EL405 plate washer, and plates were sealed and kept in PBS at 4° C. until read. Plates were read using an ArrayScan VTI instrument, using an XF53 filter with 10× objective. A two laser set up was used to analyse nuclear staining with Hoeschst (405 nm) and secondary antibody staining of pSer1981 (488 nm).

Assay b): ATR Cellular Potency
Rationale:

ATR is a PI 3-kinase-related kinase which phosphorylates multiple substrates on serine or threonine residues in response to DNA damage during or replication blocks. Chk1, a downstream protein kinase of ATR, plays a key role in DNA damage checkpoint control. Activation of Chk1 involves phosphorylation of Ser317 and Ser345 (the latter regarded as the preferential target for phosphorylation/activation by ATR). This was a cell based assay to measure inhibition of ATR kinase, by measuring a decrease in phosphorylation of Chk1 (Ser 345) in HT29 cells, following treatment with compound of Formula (I) and the UV mimetic 4NQO (Sigma #N8141).

Method Details:

HT29 cells (ECACC #85061109) were seeded into 384 well assay plates (Costar #3712) at a density of 6000 cells/well in 40 µl EMEM medium containing 1% L glutamine and 10% FBS and allowed to adhere overnight. The following morning compound of Formula (I) in 100% DMSO were added to assay plates by acoustic dispensing. After 1 h incubation at 37° C. and 5% $CO_2$, 40 nl of 3 mM 4NQO in 100% DMSO was added to all wells by acoustic dispensing, except minimum control wells which were left untreated with 4NQO to generate a null response control. Plates were returned to the incubator for a further 1 h. Then cells were fixed by adding 20 µl of 3.7% formaldehyde in PBS solution and incubating for 20 mins at r.t. Then 20 µl of 0.1% Triton X100 in PBS was added and incubated for 10 minutes at r.t., to permeabalise cells. Then the plates were washed once with 50 µl/well PBS, using a Biotek EL405 plate washer.

Phospho-Chk1 Ser 345 antibody (Cell Signalling Technology #2348) was diluted 150 fold in PBS containing 0.05% polysorbate/Tween and 15 µl was added to each well and incubated over night at r.t. The next morning plates were washed three times with 50 µl/well PBS, using a Biotek EL405 plate washer, and then 20 µl of secondary Ab solution, containing 500 fold diluted Alexa Fluor 488 Goat anti-rabbit IgG (Molecular Probes #A-11008) and 0.002 mg/ml Hoeschst dye (Molecular Probes #H-3570), in PBST, was added. After 2 h incubation at r.t., the plates were washed three times with 50 µl/well PBS, using a Biotek EL405 plate washer, and plates were then sealed with black plate seals until read. Plates were read using an ArrayScan VTI instrument, using an XF53 filter with 10× objective. A two laser set up was used to analyse nuclear staining with Hoeschst (405 nm) and secondary antibody staining of pChk1 (488 nm).

Assay c): PI3K Cellular Potency
Rationale:

This assay was used to measure PI3K-α inhibition in cells. PDK1 was identified as the upstream activation loop kinase of protein kinase B (Akt1), which is essential for the activation of PKB. Activation of the lipid kinase phosphoinositide 3 kinase (PI3K) is critical for the activation of PKB by PDK1.

Following ligand stimulation of receptor tyrosine kinases, PI3K is activated, which converts PIP2 to PIP3, which is bound by the PH domain of PDK1 resulting in recruitment of PDK1 to the plasma membrane where it phosphorylates AKT at Thr308 in the activation loop.

The aim of this cell-based mode of action assay is to identify compounds that inhibit PDK activity or recruitment of PDK1 to membrane by inhibiting PI3K activity. Phosphorylation of phospho-Akt (T308) in BT474c cells following treatment with compounds for 2 h is a direct measure of PDK1 and indirect measure of PI3K activity.

Method Details:

BT474 cells (human breast ductal carcinoma, ATCC HTB-20) were seeded into black 384 well plates (Costar, #3712) at a density of 5600 cells/well in DMEM containing 10% FBS and 1% glutamine and allowed to adhere overnight.

The following morning compounds in 100% DMSO were added to assay plates by acoustic dispensing. After a 2 h incubation at 37° C. and 5% $CO_2$, the medium was aspirated and the cells were lysed with a buffer containing 25 mM Tris, 3 mM EDTA, 3 mM EGTA, 50 mM sodium fluoride, 2 mM Sodium orthovanadate, 0.27M sucrose, 10 mM β-glycerophosphate, 5 mM sodium pyrophosphate, 0.5% Triton X-100 and complete protease inhibitor cocktail tablets (Roche #04 693 116 001, used 1 tab per 50 ml lysis buffer).

After 20 minutes, the cell lysates were transferred into ELISA plates (Greiner #781077) which had been pre-coated with an anti total-AKT antibody in PBS buffer and non-specific binding was blocked with 1% BSA in PBS containing 0.05% Tween 20. Plates were incubated over night at 4° C. The next day the plates were washed with PBS buffer containing 0.05% Tween 20 and further incubated with a mouse monoclonal anti-phospho AKT T308 for 2 h. Plates were washed again as above before addition of a horse anti-mouse-HRP conjugated secondary antibody. Following a 2 h incubation at r.t., plates were washed and QuantaBlu substrate working solution (Thermo Scientific #15169, prepared according to provider's instructions) was added to each well. The developed fluorescent product was stopped after 60 minutes by addition of Stop solution to the wells. Plates were read using a Tecan Safire plate reader using 325 nm excitation and 420 nm emission wavelengths respectively. Except where specified, reagents contained in the Path Scan Phospho AKT (Thr308) sandwich ELISA kit from Cell Signalling (#7144) were used in this ELISA assay.

Assay d): mTOR Cellular Potency

Rationale:

This assay was used to measure mTOR inhibition in cells. The aim of the phospho-AKT cell based mechanism of action assay using the Acumen Explorer is to identify inhibitors of either PI3Kα or mTOR-Rictor (Rapamycin insensitive companion of mTOR). This is measured by any decrease in the phosphorylation of the Akt protein at Ser473 (AKT lies downstream of PI3Kα in the signal transduction pathway) in the MDA-MB-468 cells following treatment with compound.

Method Details:

MDA-MB-468 cells (human breast adenocarcinoma #ATCC HTB 132) were seeded at 1500 cells/well in 40 µl of DMEM containing 10% FBS and 1% glutamine into Greiner 384 well black flat-bottomed plates. Cell plates were incubated for 18 h in a 37° C. incubator before dosing with compounds of Formula (I) in 100% DMSO using acoustic dispensing. Compounds were dosed in a 12 point concentration range into a randomised plate map. Control wells were generated either by dosing of 100% DMSO (max signal) or addition of a reference compound (a PI3K-β inhibitor) that completely eliminated the pAKT signal (min control). Compounds were then tested by one of two assay protocols A or B:

Protocol A:

Plates were incubated at 37° C. for 2 h; cells were then fixed by the addition of 10 µl of a 3.7% formaldehyde solution. After 30 minutes the plates were washed with PBS using a Tecan PW384 plate washer. Wells were blocked and cells permeabilised with the addition of 40 µl of PBS containing 0.5% Tween20 and 1% Marvel™ (dried milk powder) and incubated for 60 minutes at r.t. The plates were washed with PBS containing 0.5% (v/v) Tween20 and 20 µl rabbit anti-phospho AKT Ser473 (Cell Signalling Technologies, #3787) in same PBS-Tween+1% Marvel™ was added and incubated overnight at 4° C.

Plates were washed 3 times with PBS+0.05% Tween 20 using a Tecan PW384. 20 µl of secondary antibody Alexa Fluor 488 anti-Rabbit (Molecular Probes, #A11008) diluted in PBS+0.05% Tween20 containing 1% Marvel™ was added to each well and incubated for 1 h at r.t. Plates were washed three times as before then 20 µl PBS added to each well and plates sealed with a black plate sealer.

The plates were read on an Acumen plate reader as soon as possible, measuring green fluorescence after excitation with 488 nm laser. Using this system $IC_{50}$ values were generated and quality of plates was determined by control wells. Reference compounds were run each time to monitor assay performance.

Protocol B:

The cell plates were then incubated for 2 h at 37° C. before being fixed by the addition of 20 µl 3.7% formaldehyde in PBS/A (1.2% final concentration), followed by a 30 minute room temperature incubation, and then a 2× wash with 150 µl PBS/A using a BioTek ELx406 platewasher. Cells were permeabilised and blocked with 20 µl of assay buffer (0.1% Triton X-100 in PBS/A+1% BSA) for 1 h at room temperature, and then washed 1× with 50 µl PBS/A. Primary phospho-AKT (Ser473) D9E XP® rabbit monoclonal antibody (#4060, Cell Signaling Technology) was diluted 1:200 in assay buffer, 20 µl added per well, and plates were incubated at 4° C. overnight. Cell plates were washed 3× with 200 µl PBS/T, then 20 µl 1:750 dilution in assay buffer of Alexa Fluor®488 goat anti-rabbit IgG secondary antibody (#A11008, Molecular Probes, Life Technologies), with a 1:5000 dilution of Hoechst 33342, was added per well. Following a 1 h incubation at room temperature, plates were washed 3× with 200 µl PBS/T, and 40 µl PBS w/o Ca, Mg and Na Bicarb (Gibco #14190-094) was added per well.

Stained cell plates were covered with black seals, and then read on the Cell Insight imaging platform (Thermo Scientific), with a 10× objective. The primary channel (Hoechst blue fluorescence 405 nM, BGRFR_386_23) was used to Autofocus and to count number of events (this provided information about cytotoxicity of the compounds tested). The secondary channel (Green 488 nM, BGRFR_485_20) measured pAKT staining. Data was analysed and $IC_{50S}$ were calculated using Genedata Screener software.

Table 2 shows the results of testing the Examples in tests a) b) c) and d). Results may be the geometric mean of several tests.

TABLE 2

Potency Data for Examples 1-18 in Assays a)-d)

| Example | Assay a) ATM Cell IC$_{50}$ (µM) | Assay b) ATR Cell IC$_{50}$ (µM) | Assay c) PI3Kα Cell IC$_{50}$ (µM) | Assay d) mTOR Cell IC$_{50}$ (µM) |
|---|---|---|---|---|
| 1 | 0.000879 | >30 | 13.4 | >30* |
| 2 | 0.000787 | >30 | >12 | >30* |
| 3 | 0.000824 | >30 | 11.4 | >20§ |
| 4 | 0.00159 | >30 | 4.52 | >30§ |
| 5 | 0.000253 | 17.9 | 1.24 | 6.76* |
| 6 | 0.000398 | >20.7 | 0.184 | >3.12§ |
| 7 | 0.000256 | >30 | 0.222 | 3.19* |
| 8 | 0.000698 | | 0.661 | 0.405* |
| 9 | <0.000453 | >30 | 5.75 | >5.19§ |
| 10 | 0.000686 | >30 | 6.18 | 3.49* |
| 11 | 0.00228 | >30 | | 23.6§ |
| 12 | 0.000799 | >30 | 2.89 | >10* |
| 13 | 0.00132 | >30 | 22.9 | >30* |
| 14 | 0.00351 | >30 | >30 | >30* |
| 15 | 0.00214 | >30 | | >0.300* |
| 16 | 0.00229 | >30 | 9.08 | >29.9§ |
| 17 | 0.00461 | >30 | | >10* |
| 18 | 0.00314 | >30 | >30 | >30§ |

§Result obtained using assay d) Protocol A
*Result obtained using assay d) Protocol B Table 3 shows comparative data for certain Compounds of CN102399218A and CN102372711A in tests a) b) c) and d). Results may be the geometric mean of several tests.

TABLE 3

Potency Data for Certain Compounds of CN102399218A and CN102372711A in Assays a)-d)

| Reference Compound | Assay a) ATM Cell IC$_{50}$ (µM) | Assay b) ATR Cell IC$_{50}$ (µM) | Assay c) PI3Ka Cell IC$_{50}$ (µM) | Assay d) mTOR Cell IC$_{50}$ (µM) |
|---|---|---|---|---|
| CN102372711A Compound 1 | 0.125 | 0.281 | 0.188 | 0.237 |
| CN102372711A Compound 4 | 0.0112 | 0.0686 | 0.102 | 0.0729 |
| CN102372711A Compound 5 | 0.0265 | 0.0644 | 0.153 | 0.113 |
| CN102399218A Compound 60 | 1.76 | 0.419 | 4.67 | 2.31 |
| CN102399218A Compound 61 | 3.46 | 1.48 | 1.73 | 0.177 |
| CN102399218A Compound 62 | 0.135 | 0.0553 | 0.149 | 0.0155 |
| CN102399218A Compound 64 | 0.216 | 0.162 | 0.247 | 0.287 |
| CN102399218A Compound 94 | 0.494 | 0.0129 | 0.0804 | 0.0414 |
| CN102399218A Compound 114 | 0.0741 | 0.0686 | 0.0131 | 0.0469 |

Table 4 shows the results of testing Metabolite A in tests a) b) c) and d). Results may be the geometric mean of several tests.

TABLE 4

Potency Data for Metabolite A in Assays a)-d)

| Compound | Assay a) ATM Cell IC$_{50}$ (µM) | Assay b) ATR Cell IC$_{50}$ (µM) | Assay c) PI3Kα Cell IC$_{50}$ (µM) | Assay d) mTOR Cell IC$_{50}$ (µM) |
|---|---|---|---|---|
| Metabolite A | 0.035 | 9.41 | 27.8 | >30* |

*Result obtained using assay d) Protocol B

The invention claimed is:

1. A method for treating symptoms of Huntington's disease in a warm-blooded animal in need of such treatment, which comprises administering to said warm-blooded animal a therapeutically effective amount of a compound of Formula (I):

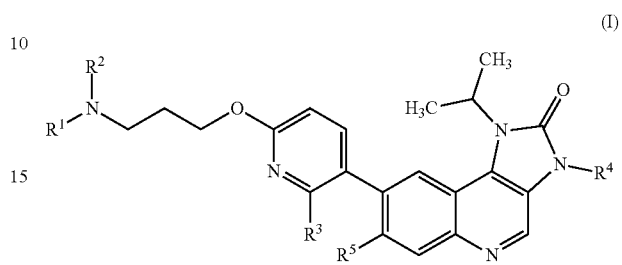

or a pharmaceutically acceptable salt thereof, where:
 $R^1$ is methyl;
 $R^2$ is hydro or methyl; or $R^1$ and $R^2$ together with the nitrogen atom to which they are bonded form an azetidinyl, pyrrolidinyl or piperidinyl ring;
 $R^3$ is hydro or fluoro;
 $R^4$ is hydro or methyl; and
 $R^5$ is hydro or fluoro.

2. The method, as claimed in claim 1, where $R^1$ and $R^2$ are both methyl; or $R^1$ and $R^2$ together with the nitrogen atom to which they are bonded form an azetidinyl, pyrrolidinyl or piperidinyl ring.

3. The method, as claimed in claim 1, where $R^1$ and $R^2$ together with the nitrogen atom to which they are bonded form an azetidinyl, pyrrolidinyl or piperidinyl ring.

4. The method, as claimed in claim 1, where $R^3$ is hydro.

5. The method, as claimed in claim 1, where $R^4$ is methyl.

6. The method, as claimed in claim 1, where $R^5$ is fluoro.

7. The method, as claimed in claim 1, where:
 $R^1$ is methyl;
 $R^2$ is methyl; or $R^1$ and $R^2$ together with the nitrogen atom to which they are bonded form an azetidinyl, pyrrolidinyl or piperidinyl ring;
 $R^3$ is hydro or fluoro;
 $R^4$ is methyl; and
 $R^5$ is hydro or fluoro.

8. The method, as claimed in claim 1, where the compound is selected from the group consisting of:
 8-[6-[3-(Dimethylamino)propoxy]-3-pyridyl]-7-fluoro-1-isopropyl-3-methyl-imidazo[4,5-c]quinolin-2-one;
 7-Fluoro-1-isopropyl-3-methyl-8-[6-[3-(1-piperidyl)propoxy]-3-pyridyl]imidazo[4,5-c]quinolin-2-one;
 7-Fluoro-1-isopropyl-3-methyl-8-[6-(3-pyrrolidin-1-yl-propoxy)-3-pyridyl]imidazo[4,5-c]quinolin-2-one;
 8-[6-[3-(azetidin-1-yl)propoxy]-3-pyridyl]-7-fluoro-1-isopropyl-3-methyl-imidazo[4,5-c]quinolin-2-one;
 1-Isopropyl-3-methyl-8-[6-[3-(1-piperidyl)propoxy]-3-pyridyl]imidazo[4,5-c]quinolin-2-one;
 8-[6-[3-(dimethylamino)propoxy]-3-pyridyl]-1-isopropyl-3-methyl-imidazo[4,5-c]quinolin-2-one;
 1-isopropyl-3-methyl-8-[6-(3-pyrrolidin-1-ylpropoxy)-3-pyridyl]imidazo[4,5-c]quinolin-2-one;
 8-[6-[3-(Azetidin-1-yl)propoxy]-3-pyridyl]-1-isopropyl-3-methyl-imidazo[4,5-c]quinolin-2-one;
 8-[2-Fluoro-6-[3-(1-piperidyl)propoxy]-3-pyridyl]-1-isopropyl-3-methyl-imidazo[4,5-c]quinolin-2-one;

8-[6-[3-(dimethylamino)propoxy]-2-fluoro-3-pyridyl]-1-isopropyl-3-methyl-imidazo[4,5-c]quinolin-2-one;

8-[6-[3-(dimethylamino)propoxy]-2-fluoro-3-pyridyl]-7-fluoro-1-isopropyl-3-methyl-imidazo[4,5-c]quinolin-2-one;

8-[2-fluoro-6-(3-pyrrolidin-1-ylpropoxy)-3-pyridyl]-1-isopropyl-3-methyl-imidazo[4,5-c]quinolin-2-one;

7-fluoro-8-[2-fluoro-6-(3-pyrrolidin-1-ylpropoxy)-3-pyridyl]-1-isopropyl-3-methyl-imidazo[4,5-c]quinolin-2-one;

7-fluoro-8-[2-fluoro-6-[3-(1-piperidyl)propoxy]-3-pyridyl]-1-isopropyl-3-methyl-imidazo[4,5-c]quinolin-2-one;

8-[6-[3-(azetidin-1-yl)propoxy]-2-fluoro-3-pyridyl]-1-isopropyl-3-methyl-imidazo[4,5-c]quinolin-2-one;

8-[6-[3-(azetidin-1-yl)propoxy]-2-fluoro-3-pyridyl]-7-fluoro-1-isopropyl-3-methyl-imidazo[4,5-c]quinolin-2-one;

8-[6-[3-(Dimethylamino)propoxy]-3-pyridyl]-7-fluoro-1-isopropyl-3H-imidazo[4,5-c]quinolin-2-one; and 7-Fluoro-1-isopropyl-8-[6-[3-(1-piperidyl)propoxy]-3-pyridyl]-3H-imidazo[4,5-c]quinolin-2-one.

9. A method for treating symptoms of Huntington's disease in a warm-blooded animal in need of such treatment, which comprises administering to said warm-blooded animal a therapeutically effective amount of 7-fluoro-1-isopropyl-3-methyl-8-[6-[3-(1-piperidyl)propoxy]-3-pyridyl]imidazo[4,5-c]quinolin-2-one, or a pharmaceutically acceptable salt thereof.

* * * * *